United States Patent [19]
Ikenaka et al.

[11] Patent Number: 6,083,752
[45] Date of Patent: *Jul. 4, 2000

[54] DNA CODING FOR DECARBAMYLASE IMPROVED IN THERMOSTABILITY AND USE THEREOF

[75] Inventors: Yasuhiro Ikenaka, Akashi; Hirokazu Nanba, Takasago; Masayuki Takano, Akashi; Kazuyoshi Yajima, Kobe; Yukio Yamada, Kakogawa; Satomi Takahashi, Kobe, all of Japan

[73] Assignee: Kanegafuchi Kagaku Kogyo Kabushiki Kaisha, Osaka, Japan

[*] Notice: This patent is subject to a terminal disclaimer.

[21] Appl. No.: 08/876,398

[22] Filed: Jun. 16, 1997

Related U.S. Application Data

[63] Continuation of application No. 08/211,641, filed as application No. PCT/JP93/01101, Aug. 5, 1993.

[30] Foreign Application Priority Data

Aug. 10, 1992 [JP] Japan ................................. 4-212692
Dec. 21, 1992 [JP] Japan ................................. 4-340078

[51] Int. Cl.[7] ............................. C12N 15/00; C12N 9/14; C12N 15/55; C12N 5/10
[52] U.S. Cl. .......................... 435/440; 435/441; 435/445; 435/447; 435/325; 435/195; 435/106; 435/320.1; 435/252.3; 435/252.33; 435/254.11; 536/23.2
[58] Field of Search ............................. 435/195, 172.1, 435/106, 320.1, 252.3, 252.33, 254.11, 325, 440, 441, 410, 447, 445; 536/23.2

[56] References Cited

U.S. PATENT DOCUMENTS

5,565,344 10/1996 Nanba et al. .......................... 435/106
5,824,522 10/1998 Ikenaka et al. ....................... 435/106

FOREIGN PATENT DOCUMENTS

0 375 889   7/1990   European Pat. Off. .
1-320991   12/1989   Japan .
9210579    6/1992   Japan .
WO 92/10579  6/1992   Japan .

OTHER PUBLICATIONS

David W. Leung et al., "A method for random mutagenesis of a defined DNA segment using a modified polymerase chain reaction", A Journal of Methods in Cell and Molecular Biology, vol. 1, No. 1 (Aug. 1989), pp. 11–15.

H.J. Liaw et al., "Molecular cloning and expression of an Erwinia—SP gene encoding diphenylether cleavage in Escherichia—Coli", Applied and Environmental Microbiology, vol. 55, No. 9 (1989), pp. 2221–2225.

(List continued on next page.)

Primary Examiner—Ponnathapu Achutamurthy
Assistant Examiner—Bradley S. Mayhew
Attorney, Agent, or Firm—Foley & Lardner

[57] ABSTRACT

A DNA fragment coding for a decarbamylase protein improved in thermostability as the result of replacement of at least one base of a DNA fragment coding for a decarbamylase protein derived from a microorganism with another base and the resultant replacement of at least one of the corresponding amino acids, and its production process; a vector containing the DNA fragment; a transformant obtained by transformation with the vector; as well as a decarbamylase improved in thermostability and its production process. Also disclosed is a process for producing a D-α-amino acid, which comprises converting an N-carbamoyl-D-α-amino acid into the corresponding D-α-amino acid in an aqueous medium by the action of a decarbamylase having a thermostable temperature of 65° C. or higher; and collecting the D-α-amino acid produced.

46 Claims, 10 Drawing Sheets

OTHER PUBLICATIONS

Battilotti et al., "Preparation of D Valine From D L-5 Isopropylhydantoin by Stereoselective Biocatalysis", J Mol Catal 43 (3). 1988. 343–352.

Bryan et al., "Proteases of Enhanced Stability Characterization of a Thermostable Variant of Subtilisin", Proteins Struct Funct Genet 1 (4). 1986. 326–334.

Matsumura et al., "Role of Tyrosine–80 in the Stability of Kanamycin Nucleotidyltransferase Analyzed by Site–Directed Mutagenesis", Eur J Biochem 171 (3). 1988. 715–720.

Makino et al., "Stability–Increasing Mutants of Glucose Dehydrogenase From Bacillus–Megaterium IWG3", J Biol Chem 264 (11). 1989. 6381–6385.

Pongor, S. Methods in Enzymology, 154:450–473, 1987.

Matthews, B. Genetics an Structural Analysis of the Protein Stability Problem, *Biochemistry*, vol. 26, No. 22, Nov. 3, 1987.

Ausubel et al. Mutagenesis of Cloned DNA, *Current Protocols in Molecular Biology*, vol. 1, John Wiley & Sons, Inc., 1991.

Makino et al. "Stability–increasing mutants of glucose dehydrogenase from bacillus megaterium IWG3" The Journal of Biological Chemistry vol. 264 No. 11 pp. 6381–6385 Apr. 15, 1989.

Myers et al. "A general method for saturation mutagenesis of cloned fragments" Science vol. 229 pp. 242–247 Jul. 7, 1985.

Leung et al. "A method for random mutagenesis of a defined DNA segment using a modified polymerase chain reaction" Technique—A journal of Methods in Cell and Molecular Biology vol. 1, No. 1 pp. 11–15 Aug. 1, 1989.

Matthews "Genetic and structural analysis of the protein stability problem" Biochemistry vol. 26 No. 22 pp. 6865–6888 Nov. 3, 1987.

Bryan et al. "Proteases of enhanced stability: Characterization of a thermostable varient of subtilisin" Proteins: Structure, Function, and Genetics vol. 1 No. 4 pp. 326–334 Dec. 1, 1986.

Rice GC, et al. "Random PCR mutagenesis screening of secreted proteins by direct expression in mammalian cells." Proc Natl Acad Sci U S A. vol. 89 No. 12 pp. 5467–5471.

FIG. 3
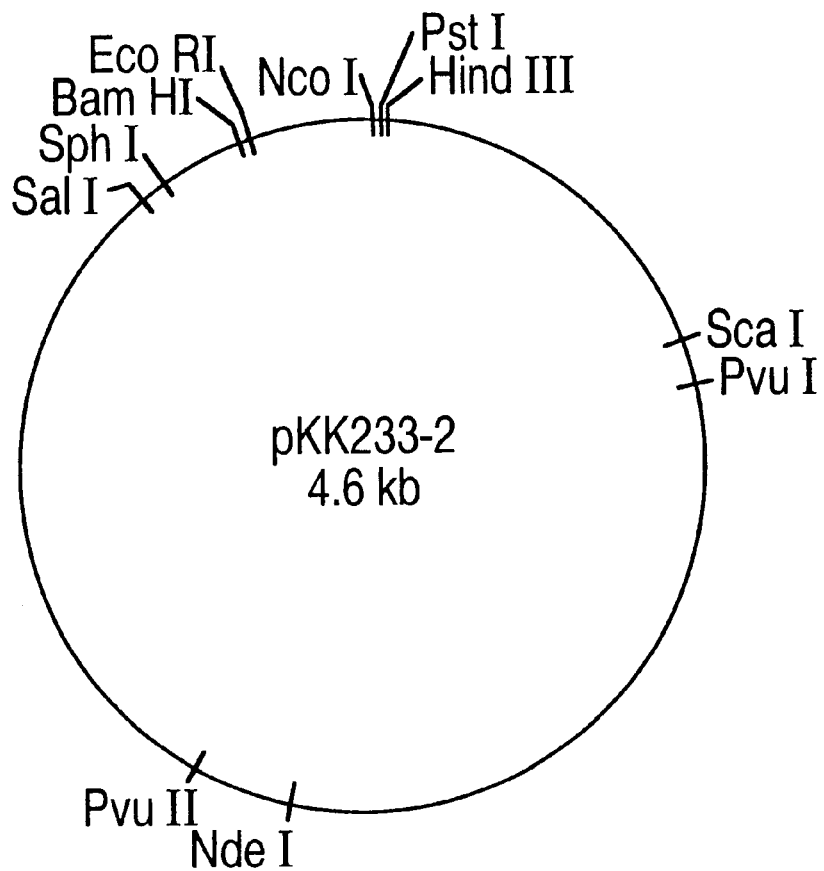
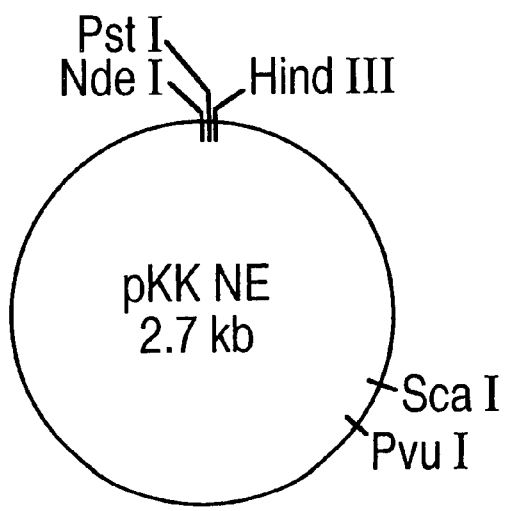

FIG. 4
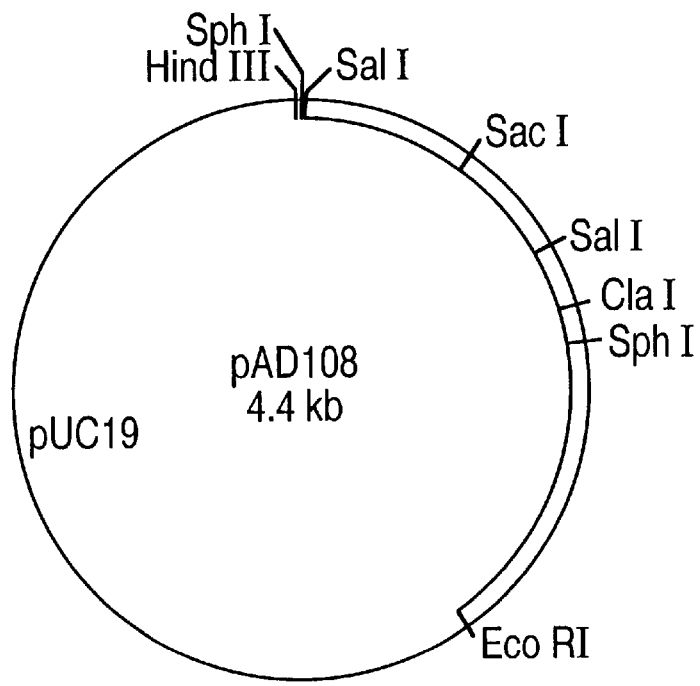
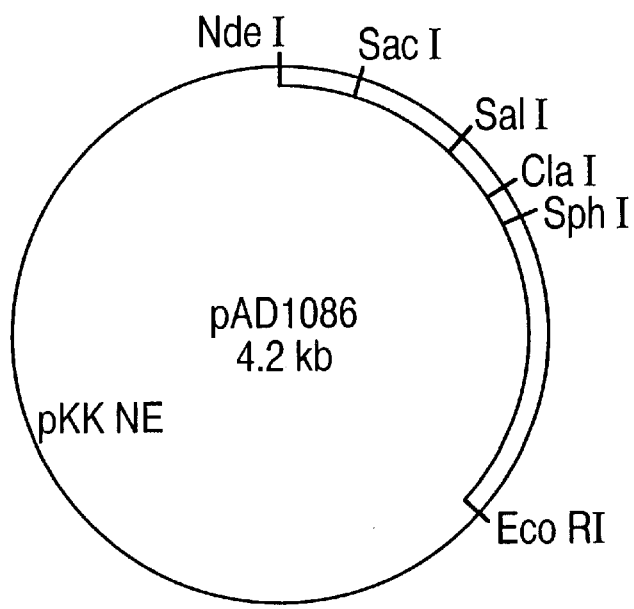

FIG. 5
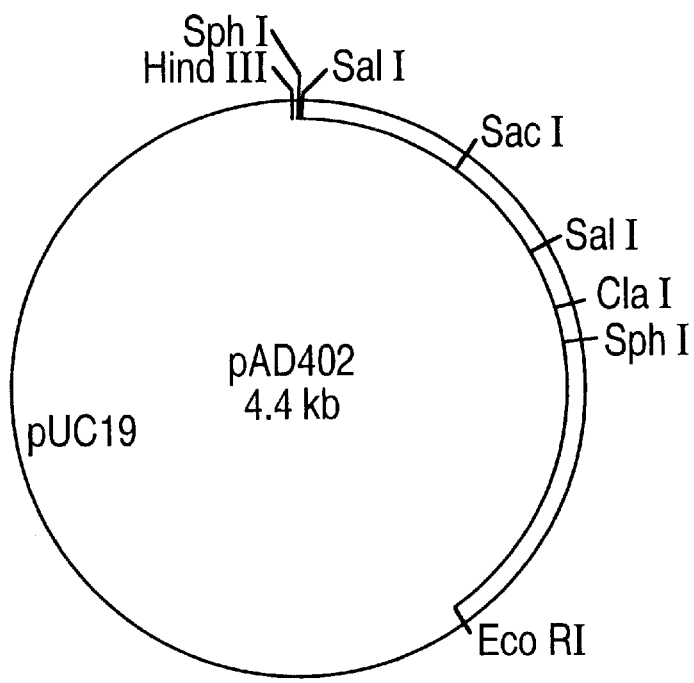
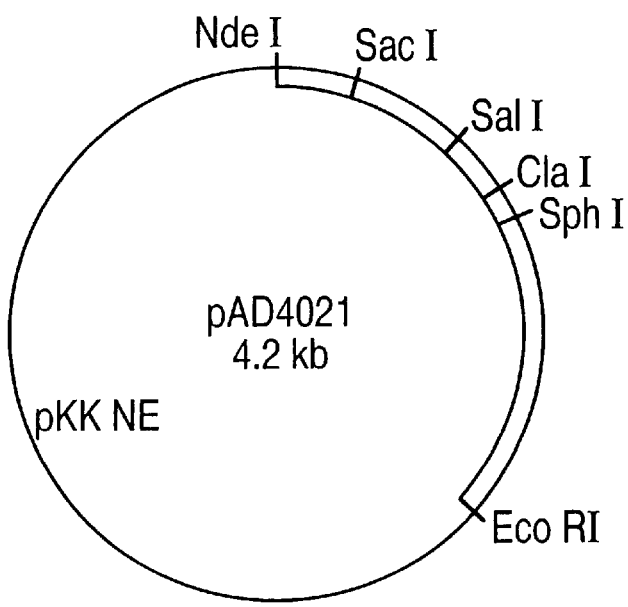

FIG. 6
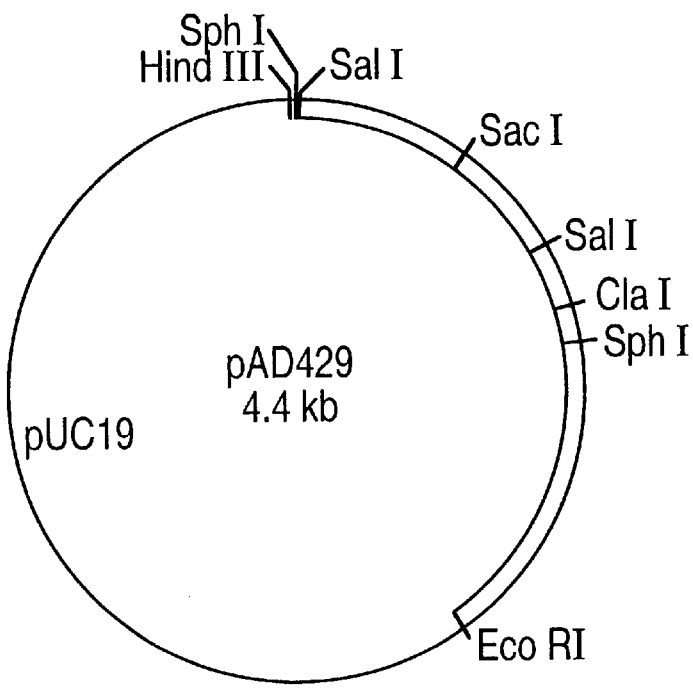
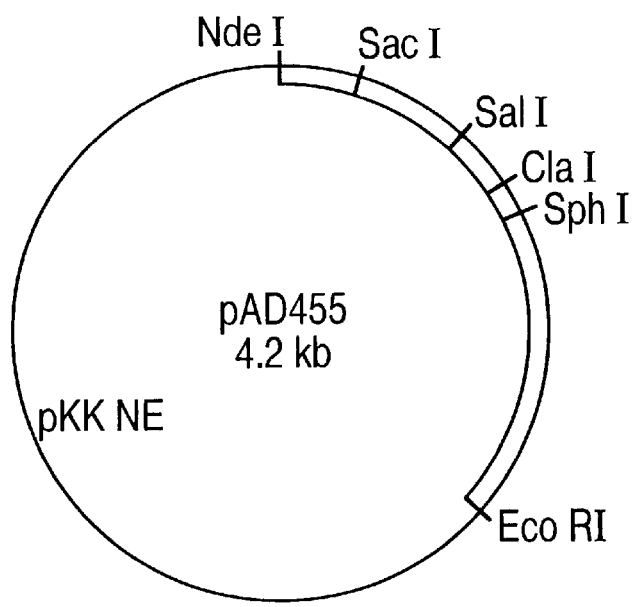

FIG. 10
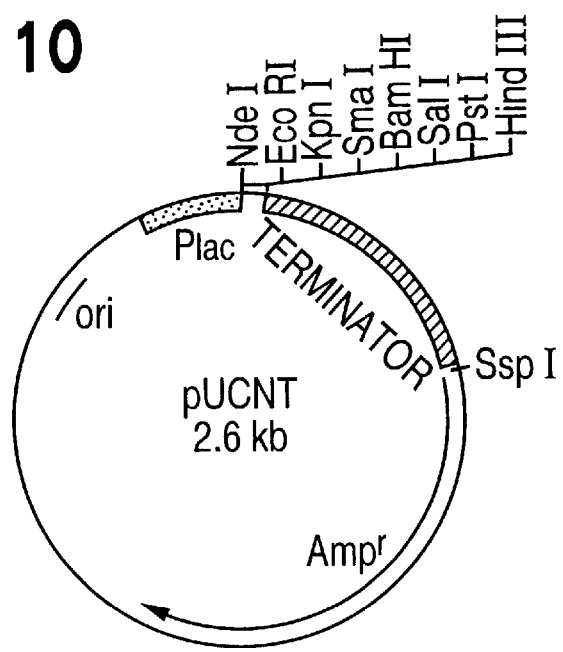
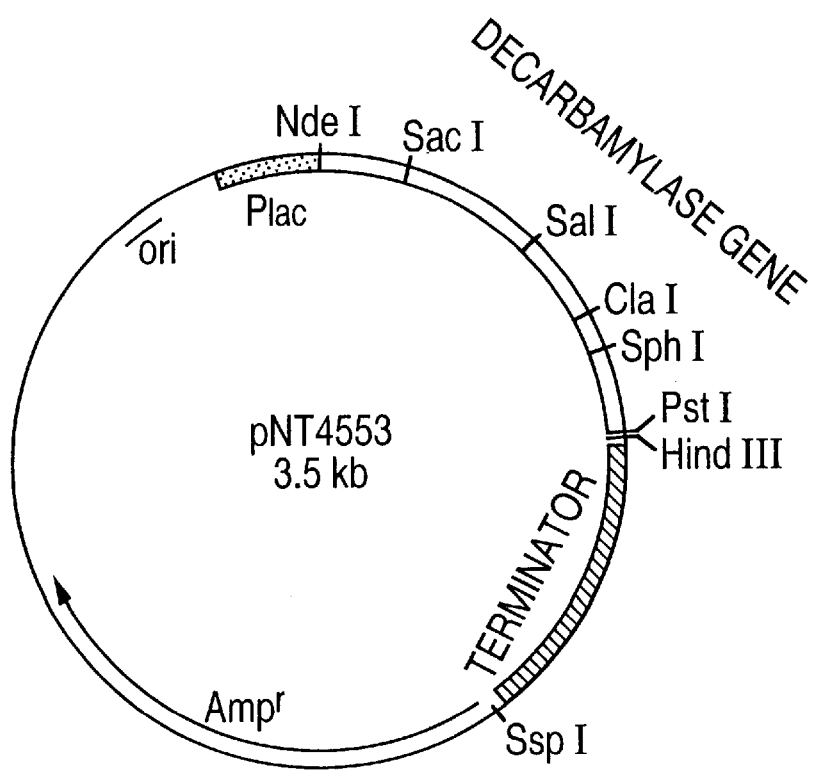

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
      (A) LENGTH: 1785 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Agrobacterium sp.
      (B) STRAIN: KNK712 (FERM BP-1900)

(ix) FEATURE:
      (A) NAME/KEY: CDS
      (B) LOCATION: join(233..1141)

(xi) SEQUENCE DESCRIPTION: SEQ ID NO:1:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                       Thr
                                                        1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
          5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
     20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
50                  55                  60                  65
```

```
AGC TTC TAT GAG ACC GAA ATG CCC GGC CCG GTG GTC CGT CCA CTC TTT        475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA        523
Glu Lys Ala Ala Glu Leu Gly Ile Gly Phe Asn Leu Gly Tyr Ala Glu
                 85                  90                  95

CTC GTC GTC GAA GGC GGC GTC AAG CGT CGC TTC AAC ACG TCC ATT TTG        571
Leu Val Val Glu Gly Gly Val Lys Arg Arg Phe Asn Thr Ser Ile Leu
                100                 105                 110

GTG GAT AAG TCA GGC AAG ATC GTC GGC AAG TAT CGT AAG ATC CAT TTG        619
Val Asp Lys Ser Gly Lys Ile Val Gly Lys Tyr Arg Lys Ile His Leu
        115                 120                 125

CCG GGT CAC AAG GAG TAC GAG GCC TAC CGG CCG TTC CAG CAT CTT GAA        667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC        715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT        763
Asp Ala Ala Lys Met Gly Met Phe Ile Cys Asn Asp Arg Arg Trp Pro
                165                 170                 175

GAA GCC TGG CGG GTG ATG GGC CTC AGG GGC GCC GAG ATC ATC TGC GGC        811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC        859
Gly Tyr Asn Thr Pro Thr His Asn Pro Pro Val Pro Gln His Asp His
195                 200                 205

CTG ACG TCC TTC CAC CAT CTC CTA TCG ATG CAG GCC GGG TCT TAT CAG        907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC        955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
                245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
275                 280                 285

CAG CAT CGT CAG CCC CAG CAC TAT GGT CTG ATC GCG GAA CTC               1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTC GTTTCGCACC GACGGCCGTC GTGAACTCGA     1321

CAGTCCGCGA GAAGGGCGTA TTGCGCGGCC TGGACCTGTA CGTGGAACTG TAGCCCATAT     1381

ATAGATTTCC AAAGAGTTTC GGCGAGGCGC GGCGCGCCTA GCCCCATGTG AGCGAGAACC     1441

GTGCCCAGAT CAAAGAATGA GACCGACGCG CCGGCCGCGG CAAAGGATGA TCCTCAGGGT     1501

CGGATCTATC GCTCCGCCCT GAAGCAGGAG GGCGCACGCT GGCTGCTGAC GGCGGAGGAA     1561

GGGTTGCTGG CAAAGCCCAA GCCGCCCGGC CTTGTTCCGG CACTTGAGAA TGCGATCGCC     1621

ATCGTCGATT ACATCAACGG TACACCGCCC CATATCGCGT CCCTGGCGGA GCTTTCAACG     1681

ACGCTCGGGA TATCCAAGAG CCACTGTCAC TCCATCCTCA AGACGCTGAC GCATTTCGGC     1741
```

TGGCTGAAAT TCGACAATCG CTCAAAGAGC TACGAGCTGA ATTC           1785

(2) INFORMATION FOR SEQ ID NO:2:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:2:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
             35                  40                  45

Leu Thr Thr Phe Phe Pro Arg Trp His Phe Thr Asp Glu Ala Glu Leu
         50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
                115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Pro Val Pro Gln His Asp
            195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
    290                 295                 300
```

(2) INFORMATION FOR SEQ ID NO:3:

(i) SEQUENCE CHARACTERISTICS:
        (A) LENGTH: 1785 base pairs
        (B) TYPE: nucleic acid
        (C) STRANDEDNESS: double

```
        (D) TOPOLOGY: linear (ii) MOLECULE TYPE: DNA (genomic)

(vi) ORIGINAL SOURCE:
         (A) ORGANISM: Escherichia coli
         (B) STRAIN: JM109 pAD402 (FERM BP-3912)

(ix) FEATURE:
         (A) NAME/KEY: CDS
         (B) LOCATION: join(233..1141)

(xi) SEQUENCE DESCRIPTION: SEQ ID NO:3:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                        Thr
                                                        1

CGT CAG ATG ATA CTT GCA GTG GGA CAA CAA GGT CCG ATC GCG CGC GCG       283
Arg Gln Met Ile Leu Ala Val Gly Gln Gln Gly Pro Ile Ala Arg Ala
            5                  10                  15

GAG ACA CGC GAA CAG GTC GTC GTT CGT CTT CTC GAC ATG CTG ACG AAA       331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT       379
Ala Ala Ser Arg Gly Ala Asn Phe Ile Val Phe Pro Glu Leu Ala Leu
     35                  40                  45

ACG ACC TTC TTC CCG CGC TGG TAT TTC ACC GAC GAG GCC GAG CTC GAT       427
Thr Thr Phe Phe Pro Arg Trp Tyr Phe Thr Asp Glu Ala Glu Leu Asp
 50                  55                  60                  65

AGC TTC TAT GAG ACC GAA ATG CCC GGC CCG GTG GTC CGT CCA CTC TTT       475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA       523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG       571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG       619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA       667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTT       715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT       763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC       811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC       859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG       907
Leu Thr Ser Phe His His Leu Leu Ser Met Gln Ala Gly Ser Tyr Gln
210                 215                 220                 225
```

```
AAC GGG GCC TGG TCC GCG GCC GCG GGC AAG GTG GGC ATG GAG GAG AAC      955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
                245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
                260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
        275                 280                 285

CAG CAT CGT CAG CCC CAG CAC TAT GGT CTG ATC GCG GAA CTC             1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG   1201

CCAGGGTGAC GCTGGTGGAA TAGTACCACG ACCGCTTCAG GGCGATCCGC AAGGAGATGC   1261

GGGTCGCCGG AGCGGCAAAG CCCGACATTC GTTTCGCACC GACGGCCGTC GTGAACTCGA   1321

CAGTCCGCGA GAAGGGCGTA TTGCGCGGCC TGGACCTGTA CGTGGAACTG TAGCCCATAT   1381

ATAGATTTCC AAAGAGTTTC GGCGAGGCGC GGCGCGCCTA GCCCCATGTG AGCGAGAACC   1441

GTGCCCAGAT CAAAGAATGA GACCGACGCG CCGGCCGCGG CAAAGGATGA TCCTCAGGGT   1501

CGGATCTATC GCTCCGCCCT GAAGCAGGAG GGCGCACGCT GGCTGCTGAC GGCGGAGGAA   1561

GGGTTGCTGG CAAAGCCCAA GCCGCCCGGC CTTGTTCCGG CACTTGAGAA TGCGATCGCC   1621

ATCGTCGATT ACATCAACGG TACACCGCCC CATATCGCGT CCCTGGCGGA GCTTTCAACG   1681

ACGCTCGGGA TATCCAAGAG CCACTGTCAC TCCATCCTCA AGACGCTGAC GCATTTCGGC   1741

TGGCTGAAAT TCGACAATCG CTCAAAGAGC TACGAGCTGA ATTC                    1785

(2) INFORMATION FOR SEQ ID NO:4:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:4:

Thr Arg Gln Met Ile Leu Ala Val Gly Gln Gly Pro Ile Ala Arg
  1               5                  10                  15

Ala Glu Thr Arg Glu Gln Val Val Arg Leu Leu Asp Met Leu Thr
                 20                  25                  30

Lys Ala Ala Ser Arg Gly Ala Asn Phe Ile Val Phe Pro Glu Leu Ala
                35                  40                  45

Leu Thr Thr Phe Phe Pro Arg Trp Tyr Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
         115                 120                 125
```

```
Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300

(2) INFORMATION FOR SEQ ID NO:5:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD404 (FERM BP-3913)

(ix) FEATURE:
        (A) NAME/KEY: CDS
        (B) LOCATION: join(233..1141)

(xi) SEQUENCE DESCRIPTION: SEQ ID NO:5:

GTCGACGGCG  GGCTCGCGCG  AGAGCTTGTC  AAGCAGCGCA  AATTCCGGTT  CCGCTCCGGT        60

TGACAGATCA  AAAATTTTAC  GCCTGTTATT  GTCGTGCTGC  ATGTAATATT  TCGTACTTTA       120

TGTAGAATTT  GCATTGCGCC  GCGAGTCACA  AAGCCGGTTT  TCGGCGATGT  GTTTCACAAC       180

GTTTTCCCGG  CCGCTGGGCC  GGACATCACC  TAGGAAGGAG  CAGAGGTTCA  TG ACA           235
                                                            Thr
                                                             1

CGT CAG ATG ATA CTT GCA GTG GGA CAA CAA GGT CCG ATC GCG CGC GCG            283
Arg Gln Met Ile Leu Ala Val Gly Gln Gln Gly Pro Ile Ala Arg Ala
          5                  10                  15

GAG ACA CGC GAA CAG GTC GTC GTT CGT CTT CTC GAC ATG CTG ACG AAA            331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT            379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT            427
Thr Thr Phe Phe Pro Arg Trp His Phe Thr Asp Glu Ala Glu Leu Asp
 50                  55                  60                  65
```

```
AGC TTC TAT GAG ACC GAA ATG CCC GGC CCG GTG GTC CGT CCA CTC TTT    475
Ser Phe Tyr Glu Thr Glu Met Pro Gly Pro Val Val Arg Pro Leu Phe
            70                  75                  80

GAG AAG GCC GCG GAA CTC GGG ATC GGC TTC AAT CTG GGC TAC GCT GAA    523
Glu Lys Ala Ala Glu Leu Gly Ile Gly Phe Asn Leu Gly Tyr Ala Glu
                85                  90                  95

CTC GTC GTC GAA GGC GGC GTC AAG CGT CGC TTC AAC ACG TCC ATT TTG    571
Leu Val Val Glu Gly Gly Val Lys Arg Arg Phe Asn Thr Ser Ile Leu
            100                 105                 110

GTG GAT AAG TCA GGC AAG ATC GTC GGC AAG TAT CGT AAG ATC CAT TTG    619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA    667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC    715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT    763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
        180                 185                 190

GGC TAC AAC ACG CCG ACC CAC AAT CCC CTT GTT CCC CAG CAC GAC CAC    859
Gly Tyr Asn Thr Pro Thr His Asn Pro Leu Val Pro Gln His Asp His
    195                 200                 205

CTG ACG TCC TTC CAC CAT CTC CTA TCG ATG CAG GCC GGG TCT TAT CAG    907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC    955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC    1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC    1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG    1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC                1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG    1201

CCAGGGTGAC GCTGGTGGAA TAGTACCACG ACCGCTTCAG GGCGATCCGC AAGGAGATGC    1261

GGGTCGCCGG AGCGGCAAAG CCCGACATTC GTTTCGCACC GACGGCCGTC GTGAACTCGA    1321

CAGTCCGCGA GAAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681
```

ACGCTCGGGA TATCCAAGAG CCACTGTCAC TCCATCCTCA AGACGCTGAC GCATTTCGGC      1741

TGGCTGAAAT TCGACAATCG CTCAAAGAGC TACGAGCTGA ATTC      1785

(2) INFORMATION FOR SEQ ID NO:6:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:6:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
         35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Leu Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300
```

(2) INFORMATION FOR SEQ ID NO:7:

(i) SEQUENCE CHARACTERISTICS:
        (A) LENGTH: 1785 base pairs
        (B) TYPE: nucleic acid (C) STRANDEDNESS: double
    (D) TOPOLOGY: linear (ii) MOLECULE TYPE: DNA (genomic)

(vi) ORIGINAL SOURCE:
    (A) ORGANISM: Escherichia coli
    (B) STRAIN: JM109 pAD406 (FERM BP-3914)

(ix) FEATURE:
    (A) NAME/KEY: CDS
    (B) LOCATION: join(233..1141)

(xi) SEQUENCE DESCRIPTION: SEQ ID NO:7:

```
GTCGACGGCG GGCTCGCGCG AGAGCTTGTC AAGCAGCGCA AATTCCGGTT CCGCTCCGGT    60

TGACAGATCA AAAATTTTAC GCCTGTTATT GTCGTGCTGC ATGTAATATT TCGTACTTTA   120

TGTAGAATTT GCATTGCGCC GCGAGTCACA AAGCCGGTTT TCGGCGATGT GTTTCACAAC   180

GTTTTCCCGG CCGCTGGGCC GGACATCACC TAGGAAGGAG CAGAGGTTCA TG ACA       235
                                                       Thr
                                                        1

CGT CAG ATG ATA CTT GCA GTG GGA CAA CAA GGT CCG ATC GCG CGC GCG    283
Arg Gln Met Ile Leu Ala Val Gly Gln Gln Gly Pro Ile Ala Arg Ala
          5                  10                  15

GAG ACA CGC GAA CAG GTC GTC GTT CGT CTT CTC GAC ATG CTG ACG AAA    331
Glu Thr Arg Glu Gln Val Val Val Arg Leu Leu Asp Met Leu Thr Lys
        20                  25                  30

GCC GCG AGC CGG GGC GCG AAT TTC ATT GTC TTC CCC GAA CTC GCG CTT    379
Ala Ala Ser Arg Gly Ala Asn Phe Ile Val Phe Pro Glu Leu Ala Leu
    35                  40                  45

ACG ACC TTC TTC CCG CGC TGG CAT TTC ACC GAC GAG GCC GAG CTC GAT    427
Thr Thr Phe Phe Pro Arg Trp His Phe Thr Asp Glu Ala Glu Leu Asp
50                  55                  60                  65

AGC TTC TAT GAG ACC GAA ATG CCC GGC CCG GTG GTC CGT CCA CTC TTT    475
Ser Phe Tyr Glu Thr Glu Met Pro Gly Pro Val Val Arg Pro Leu Phe
                70                  75                  80

GAG AAG GCC GCG GAA CTC GGG ATC GGC TTC AAT CTG GGC TAC GCT GAA    523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG    571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG    619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA    667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC    715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT    763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
        180                 185                 190

GGC TAC AAC ACG CCG ACC CAC AAT CCC TCT GTT CCC CAG CAC GAC CAC    859
Gly Tyr Asn Thr Pro Thr His Asn Pro Ser Val Pro Gln His Asp His
    195                 200                 205

CTG ACG TCC TTC CAC CAT CTC CTA TCG ATG CAG GCC GGG TCT TAT CAG    907
Leu Thr Ser Phe His His Leu Leu Ser Met Gln Ala Gly Ser Tyr Gln
```

```
                    210                215                220                225
AAC GGG GCC TGG TCC GCG GCC GCG GGC AAG GTG GGC ATG GAG GAG AAC          955
Asn Gly Ala Trp Ser Ala Ala Ala Gly Lys Val Gly Met Glu Glu Asn
                        230                235                240

TGC ATG CTG CTC GGC CAC TCC TGC ATC GTG GCG CCG ACC GGG GAA ATC         1003
Cys Met Leu Leu Gly His Ser Cys Ile Val Ala Pro Thr Gly Glu Ile
            245                250                255

GTC GCT CTC ACT ACG ACG CTG GAA GAC GAG GTG ATC ACC GCC GCC GTC         1051
Val Ala Leu Thr Thr Thr Leu Glu Asp Glu Val Ile Thr Ala Ala Val
        260                265                270

GAT CTC GAT CGC TGC CGG GAA CTG CGT GAA CAC ATC TTC AAC TTC AAG         1099
Asp Leu Asp Arg Cys Arg Glu Leu Arg Glu His Ile Phe Asn Phe Lys
    275                280                285

CAG CAT CGT CAG CCC CAG CAC TAT GGT CTG ATC GCG GAA CTC                 1141
Gln His Arg Gln Pro Gln His Tyr Gly Leu Ile Ala Glu Leu
290                295                300

TGAGGTTGCC GAAAAGCATG TGTGTCGTTG TTCTCGGCGC CTGGGTCACA TCCAGGCGCG       1201

CCAGGGTGAC GCTGGTGGAA TAGTACCACG ACCGCTTCAG GGCGATCCGC AAGGAGATGC       1261

GGGTCGCCGG AGCGGCAAAG CCCGACATTC GTTTCGCACC GACGGCCGTC GTGAACTCGA       1321

CAGTCCGCGA AAGGGCGTA TTGCGCGGCC TGGACCTGTA CGTGGAACTG TAGCCCATAT        1381

ATAGATTTCC AAAGAGTTTC GGCGAGGCGC GGCGCGCCTA GCCCCATGTG AGCGAGAACC       1441

GTGCCCAGAT CAAAGAATGA GACCGACGCG CCGGCCGCGG CAAAGGATGA TCCTCAGGGT       1501

CGGATCTATC GCTCCGCCCT GAAGCAGGAG GGCGCACGCT GGCTGCTGAC GGCGGAGGAA      1561

GGGTTGCTGG CAAAGCCCAA GCCGCCCGGC CTTGTTCCGG CACTTGAGAA TGCGATCGCC       1621

ATCGTCGATT ACATCAACGG TACACCGCCC CATATCGCGT CCCTGGCGGA GCTTTCAACG       1681

ACGCTCGGGA TATCCAAGAG CCACTGTCAC TCCATCCTCA AGACGCTGAC GCATTTCGGC       1741

TGGCTGAAAT TCGACAATCG CTCAAAGAGC TACGAGCTGA ATTC                        1785

(2) INFORMATION FOR SEQ ID NO:8:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:8:

Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
         35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125
```

```
Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Ser Val Pro Gln His Asp
            195                 200                 205

His Leu Thr Ser Phe His His Leu Leu Ser Met Gln Ala Gly Ser Tyr
        210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
        290                 295                 300

(2) INFORMATION FOR SEQ ID NO:9:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD416 (FERM BP-3915)

(ix) FEATURE:
        (A) NAME/KEY: CDS
        (B) LOCATION: join(233..1141)

(xi) SEQUENCE DESCRIPTION: SEQ ID NO:9:

GTCGACGGCG GGCTCGCGCG AGAGCTTGTC AAGCAGCGCA AATTCCGGTT CCGCTCCGGT       60

TGACAGATCA AAAATTTTAC GCCTGTTATT GTCGTGCTGC ATGTAATATT TCGTACTTTA      120

TGTAGAATTT GCATTGCGCC GCGAGTCACA AAGCCGGTTT TCGGCGATGT GTTTCACAAC      180

GTTTTCCCGG CCGCTGGGCC GGACATCACC TAGGAAGGAG CAGAGGTTCA TG ACA          235
                                                        Thr
                                                        1

CGT CAG ATG ATA CTT GCA GTG GGA CAA CAA GGT CCG ATC GCG CGC GCG        283
Arg Gln Met Ile Leu Ala Val Gly Gln Gln Gly Pro Ile Ala Arg Ala
        5                   10                  15

GAG ACA CGC GAA CAG GTC GTC GTT CGT CTT CTC GAC ATG CTG ACG AAA        331
Glu Thr Arg Glu Gln Val Val Val Arg Leu Leu Asp Met Leu Thr Lys
    20                  25                  30

GCC GCG AGC CGG GGC GCG AAT TTC ATT GTC TTC CCC GAA CTC GCG CTT        379
Ala Ala Ser Arg Gly Ala Asn Phe Ile Val Phe Pro Glu Leu Ala Leu
35                  40                  45

ACG ACC TTC TTC CCG CGC TGG CAT TTC ACC GAC GAG GCC GAG CTC GAT        427
Thr Thr Phe Phe Pro Arg Trp His Phe Thr Asp Glu Ala Glu Leu Asp
```

-continued

```
                  50                       55                       60                       65
AGC TTC TAT GAG ACC GAA ATG CCC GGC CCG GTG GTC CGT CCA CTC TTT                              475
Ser Phe Tyr Glu Thr Glu Met Pro Gly Pro Val Val Arg Pro Leu Phe
                70                       75                       80

GAG AAG GCC GCG GAA CTC GGG ATC GGC TTC AAT CTG GGC TAC GCT GAA                              523
Glu Lys Ala Ala Glu Leu Gly Ile Gly Phe Asn Leu Gly Tyr Ala Glu
                    85                       90                       95

CTC GTC GTC GAA GGC GGC GTC AAG CGT CGC TTC AAC ACG TCC ATT TTG                              571
Leu Val Val Glu Gly Gly Val Lys Arg Arg Phe Asn Thr Ser Ile Leu
                100                      105                      110

GTG GAT AAG TCA GGC AAG ATC GTC GGC AAG TAT CGT AAG ATC CAT TTG                              619
Val Asp Lys Ser Gly Lys Ile Val Gly Lys Tyr Arg Lys Ile His Leu
                115                      120                      125

CCG GGT CAC AAG GAG TAC GAG GCC TAC CGG CCG TTC CAG CAT CTT GAA                              667
Pro Gly His Lys Glu Tyr Glu Ala Tyr Arg Pro Phe Gln His Leu Glu
130                      135                      140                      145

AAG CGT TAT TTC GAG CCG GGC GAT CTC GGC TTC CCG GTC TAT GAC GTC                              715
Lys Arg Tyr Phe Glu Pro Gly Asp Leu Gly Phe Pro Val Tyr Asp Val
                150                      155                      160

GAC GCC GCG AAA ATG GGG ATG TTC ATC TGC AAC GAT CGC CGC TGG CCT                              763
Asp Ala Ala Lys Met Gly Met Phe Ile Cys Asn Asp Arg Arg Trp Pro
                165                      170                      175

GAA GCC TGG CGG GTG ATG GGC CTC AGG GGC GCC GAG ATC ATC TGC GGC                              811
Glu Ala Trp Arg Val Met Gly Leu Arg Gly Ala Glu Ile Ile Cys Gly
                180                      185                      190

GGC TAC AAC ACG CCG ACC CAC AAT CCC CCT GTT CCC CAG CAC GAC CAC                              859
Gly Tyr Asn Thr Pro Thr His Asn Pro Pro Val Pro Gln His Asp His
                195                      200                      205

CTG ACG TCC TTC CAC CAT CTC CTA TCG ATG CAG GCC GGG TCT TAT CAG                              907
Leu Thr Ser Phe His His Leu Leu Ser Met Gln Ala Gly Ser Tyr Gln
210                      215                      220                      225

AAC GGG GCC TGG TCC GCG GCC GCG GGC AAG GCG GGC ATG GAG GAG AAC                              955
Asn Gly Ala Trp Ser Ala Ala Ala Gly Lys Ala Gly Met Glu Glu Asn
                230                      235                      240

TGC ATG CTG CTC GGC CAC TCC TGC ATC GTG GCG CCG ACC GGG GAA ATC                              1003
Cys Met Leu Leu Gly His Ser Cys Ile Val Ala Pro Thr Gly Glu Ile
                245                      250                      255

GTC GCT CTC ACT ACG ACG CTG GAA GAC GAG GTG ATC ACC GCC GCC GTC                              1051
Val Ala Leu Thr Thr Thr Leu Glu Asp Glu Val Ile Thr Ala Ala Val
                260                      265                      270

GAT CTC GAT CGC TGC CGG GAA CTG CGT GAA CAC ATC TTC AAC TTC AAG                              1099
Asp Leu Asp Arg Cys Arg Glu Leu Arg Glu His Ile Phe Asn Phe Lys
                275                      280                      285

CAG CAT CGT CAG CCC CAG CAC TAT GGT CTG ATC GCG GAA CTC                                       1141
Gln His Arg Gln Pro Gln His Tyr Gly Leu Ile Ala Glu Leu
290                      295                      300

TGAGGTTGCC GAAAAGCATG TGTGTCGTTG TTCTCGGCGC CTGGGTCACA TCCAGGCGCG                             1201

CCAGGGTGAC GCTGGTGGAA TAGTACCACG ACCGCTTCAG GGCGATCCGC AAGGAGATGC                             1261

GGGTCGCCGG AGCGGCAAAG CCCGACATTG GTTTCGCACC GACGGCCGTC GTGAACTCGA                             1321

CAGTCCGCGA GAAGGGCGTA TTGCGCGGCC TGGACCTGTA CGTGGAACTG TAGCCCATAT                             1381

ATAGATTTCC AAAGAGTTTC GGCGAGGCGC GGCGCGCCTA GCCCCATGTG AGCGAGAACC                             1441

GTGCCCAGAT CAAAGAATGA GACCGACGCG CCGGCCGCGG CAAAGGATGA TCCTCAGGGT                             1501

CGGATCTATC GCTCCGCCCT GAAGCAGGAG GGCGCACGCT GGCTGCTGAC GGCGGAGGAA                             1561

GGGTTGCTGG CAAAGCCCAA GCCGCCCGGC CTTGTTCCGG CACTTGAGAA TGCGATCGCC                             1621

ATCGTCGATT ACATCAACGG TACACCGCCC CATATCGCGT CCCTGGCGGA GCTTTCAACG                             1681
```

```
ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785
```

(2) INFORMATION FOR SEQ ID NO:10:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:10:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
         35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
                115                 120                 125

Leu Pro Gly His Lys Glu Tyr Glu Ala Tyr Arg Pro Phe Gln His Leu
            130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300
```

(2) INFORMATION FOR SEQ ID NO:11:

(i) SEQUENCE CHARACTERISTICS:
        (A) LENGTH: 1785 base pairs (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli
         (B) STRAIN: JM109 pAD428

(ix) FEATURE:
         (A) NAME/KEY: CDS
         (B) LOCATION: join(233..1141)

(xi) SEQUENCE DESCRIPTION: SEQ ID NO:11:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                         Thr
                                                          1

CGT CAG ATG ATA CTT GCA GTG GGA CAA CAA GGT CCG ATC GCG CGC GCG       283
Arg Gln Met Ile Leu Ala Val Gly Gln Gln Gly Pro Ile Ala Arg Ala
            5                  10                  15

GAG ACA CGC GAA CAG GTC GTC GTT CGT CTT CTC GAC ATG CTG ACG AAA       331
Glu Thr Arg Glu Gln Val Val Val Arg Leu Leu Asp Met Leu Thr Lys
 20                  25                  30

GCC GCG AGC CGG GGC GCG AAT TTC ATT GTC TTC CCC GAA CTC GCG CTT       379
Ala Ala Ser Arg Gly Ala Asn Phe Ile Val Phe Pro Glu Leu Ala Leu
         35                  40                  45

ACG ACC TTC TTC CCG CGC TGG CAT TTC ACC GAC GAG GCC GAG CTC GAT       427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT       475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA       523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG       571
Leu Val Val Glu Gly Gly Val Lys Arg Arg Phe Asn Thr Ser Ile Leu
     100                 105                 110

GTG GAT AAG TCA GGC AAG ATC GTC GGC AAG TAT CGT AAG ATC CAT TTG       619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA       667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC       715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT       763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC       811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC       859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG       907
```

```
Leu Thr Ser Phe His His Leu Ser Met Gln Ala Gly Ser Tyr Gln
210                 215                 220                 225

AAC GGG GCC TGG TCC GCG GCC GCG GGC AAG GCC GGC ATG GAG GAG AAC        955
Asn Gly Ala Trp Ser Ala Ala Ala Gly Lys Ala Gly Met Glu Glu Asn
                    230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
                245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
            260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
        275                 280                 285

CAG CAT CGT CAG CCC CAG CAC TAT GGT CTG ATC GCG GAA CTC               1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTC GTTTCGCACC GACGGCCGTC GTGAACTCGA     1321

CAGTCCGCGA AAGGGCGTA TTGCGCGGCC TGGACCTGTA CGTGGAACTG TAGCCCATAT      1381

ATAGATTTCC AAAGAGTTTC GGCGAGGCGC GGCGCGCCTA GCCCCATGTG AGCGAGAACC     1441

GTGCCCAGAT CAAAGAATGA GACCGACGCG CCGGCCGCGG CAAAGGATGA TCCTCAGGGT     1501

CGGATCTATC GCTCCGCCCT GAAGCAGGAG GGCGCACGCT GGCTGCTGAC GGCGGAGGAA     1561

GGGTTGCTGG CAAAGCCCAA GCCGCCCGGC CTTGTTCCGG CACTTGAGAA TGCGATCGCC     1621

ATCGTCGATT ACATCAACGG TACACCGCCC CATATCGCGT CCCTGGCGGA GCTTTCAACG     1681

ACGCTCGGGA TATCCAAGAG CCACTGTCAC TCCATCCTCA AGACGCTGAC GCATTTCGGC     1741

TGGCTGAAAT TCGACAATCG CTCAAAGAGC TACGAGCTGA ATTC                      1785

(2) INFORMATION FOR SEQ ID NO:12:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:12:

Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
```

```
            115                 120                 125
Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300

(2) INFORMATION FOR SEQ ID NO:13:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD429

(ix) FEATURE:
        (A) NAME/KEY: CDS
        (B) LOCATION: join(233..1141)

(xi) SEQUENCE DESCRIPTION: SEQ ID NO:13:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA    120

TGTAGAATTT GCATTGCGCC GCGAGTCACA AAGCCGGTTT TCGGCGATGT GTTTCACAAC    180

GTTTTCCCGG CCGCTGGGCC GGACATCACC TAGGAAGGAG CAGAGGTTCA TG ACA         235
                                                        Thr
                                                         1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
        5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
    20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT      427
```

-continued

```
Thr Thr Phe Phe Pro Arg Trp His Phe Thr Asp Glu Ala Glu Leu Asp
 50              55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
         100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
     115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                 150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
             165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
         180                 185                 190

GGC TAC AAC ACG CCG ACC CAC AAT CCC GAA GTT CCC CAG CAC GAC CAC      859
Gly Tyr Asn Thr Pro Thr His Asn Pro Glu Val Pro Gln His Asp His
     195                 200                 205

CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC      955
Asn Gly Ala Trp Ser Ala Ala Ala Gly Lys Val Gly Met Glu Glu Asn
                 230                 235                 240

TGC ATG CTG CTC GGC CAC TCC TGC ATC GTG GCG CCG ACC GGG GAA ATC      1003
Cys Met Leu Leu Gly His Ser Cys Ile Val Ala Pro Thr Gly Glu Ile
             245                 250                 255

GTC GCT CTC ACT ACG ACG CTG GAA GAC GAG GTG ATC ACC GCC GCC GTC      1051
Val Ala Leu Thr Thr Thr Leu Glu Asp Glu Val Ile Thr Ala Ala Val
         260                 265                 270

GAT CTC GAT CGC TGC CGG GAA CTG CGT GAA CAC ATC TTC AAC TTC AAG      1099
Asp Leu Asp Arg Cys Arg Glu Leu Arg Glu His Ile Phe Asn Phe Lys
     275                 280                 285

CAG CAT CGT CAG CCC CAG CAC TAT GGT CTG ATC GCG GAA CTC              1141
Gln His Arg Gln Pro Gln His Tyr Gly Leu Ile Ala Glu Leu
290                 295                 300
```

TGAGGTTGCC GAAAAGCATG TGTGTCGTTG TTCTCGGCGC CTGGGTCACA TCCAGGCGCG  1201

CCAGGGTGAC GCTGGTGGAA TAGTACCACG ACCGCTTCAG GGCGATCCGC AAGGAGATGC  1261

GGGTCGCCGG AGCGGCAAAG CCCGACATTG GTTTCGCACC GACGGCCGTC GTGAACTCGA  1321

CAGTCCGCGA GAAGGGCGTA TTGCGCGGCC TGGACCTGTA CGTGGAACTG TAGCCCATAT  1381

ATAGATTTCC AAAGAGTTTC GGCGAGGCGC GGCGCGCCTA GCCCCATGTG AGCGAGAACC  1441

GTGCCCAGAT CAAAGAATGA GACCGACGCG CCGGCCGCGG CAAAGGATGA TCCTCAGGGT  1501

CGGATCTATC GCTCCGCCCT GAAGCAGGAG GGCGCACGCT GGCTGCTGAC GGCGGAGGAA  1561

GGGTTGCTGG CAAAGCCCAA GCCGCCCGGC CTTGTTCCGG CACTTGAGAA TGCGATCGCC  1621

```
ATCGTCGATT ACATCAACGG TACACCGCCC CATATCGCGT CCCTGGCGGA GCTTTCAACG        1681

ACGCTCGGGA TATCCAAGAG CCACTGTCAC TCCATCCTCA AGACGCTGAC GCATTTCGGC        1741

TGGCTGAAAT TCGACAATCG CTCAAAGAGC TACGAGCTGA ATTC                        1785
```

(2) INFORMATION FOR SEQ ID NO:14:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:14:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
             35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Glu Val Pro Gln His Asp
            195                 200                 205

His Leu Thr Ser Phe His His Leu Leu Ser Met Gln Ala Gly Ser Tyr
        210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
        290                 295                 300
```

(2) INFORMATION FOR SEQ ID NO:15:

(i) SEQUENCE CHARACTERISTICS:

(A) LENGTH: 1785 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Escherichia coli
(B) STRAIN: JM109 pAD431

(ix) FEATURE:
(A) NAME/KEY: CDS
(B) LOCATION: join(233..1141)

(xi) SEQUENCE DESCRIPTION: SEQ ID NO:15:

```
GTCGACGGCG GGCTCGCGCG AGAGCTTGTC AAGCAGCGCA AATTCCGGTT CCGCTCCGGT    60

TGACAGATCA AAAATTTTAC GCCTGTTATT GTCGTGCTGC ATGTAATATT TCGTACTTTA   120

TGTAGAATTT GCATTGCGCC GCGAGTCACA AAGCCGGTTT TCGGCGATGT GTTTCACAAC   180

GTTTTCCCGG CCGCTGGGCC GGACATCACC TAGGAAGGAG CAGAGGTTCA TG ACA       235
                                                         Thr
                                                          1

CGT CAG ATG ATA CTT GCA GTG GGA CAA CAA GGT CCG ATC GCG CGC GCG    283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA    331
Glu Thr Arg Glu Gln Val Val Val Arg Leu Leu Asp Met Leu Thr Lys
 20                  25                  30

GCC GCG AGC CGG GGC GCG AAT TTC ATT GTC TTC CCC GAA CTC GCG CTT    379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT    427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT    475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA    523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG    571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG    619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA    667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC    715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT    763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
        180                 185                 190

GGC TAC AAC ACG CCG ACC CAC AAT CCC AAC GTT CCC CAG CAC GAC CAC    859
Gly Tyr Asn Thr Pro Thr His Asn Pro Asn Val Pro Gln His Asp His
    195                 200                 205
```

```
CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC      955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC             1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG    1201

CCAGGGTGAC GCTGGTGGAA TAGTACCACG ACCGCTTCAG GGCGATCCGC AAGGAGATGC    1261

GGGTCGCCGG AGCGGCAAAG CCCGACATTC GTTTCGCACC GACGGCCGTC GTGAACTCGA    1321

CAGTCCGCGA AAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785

(2) INFORMATION FOR SEQ ID NO:16:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:16:

Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
            100                 105                 110
```

```
Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Asn Val Pro Gln His Asp
        195                 200                 205

His Leu Thr Ser Phe His His Leu Leu Ser Met Gln Ala Gly Ser Tyr
        210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
        290                 295                 300

(2) INFORMATION FOR SEQ ID NO:17:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD434

(ix) FEATURE:
        (A) NAME/KEY: CDS
        (B) LOCATION: join(233..1141)

(xi) SEQUENCE DESCRIPTION: SEQ ID NO:17:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA    120

TGTAGAATTT GCATTGCGCC GCGAGTCACA AAGCCGGTTT TCGGCGATGT GTTTCACAAC    180

GTTTTCCCGG CCGCTGGGCC GGACATCACC TAGGAAGGAG CAGAGGTTCA TG ACA        235
                                                           Thr
                                                             1

CGT CAG ATG ATA CTT GCA GTG GGA CAA CAA GGT CCG ATC GCG CGC GCG     283
Arg Gln Met Ile Leu Ala Val Gly Gln Gln Gly Pro Ile Ala Arg Ala
            5                  10                  15

GAG ACA CGC GAA CAG GTC GTC GTT CGT CTT CTC GAC ATG CTG ACG AAA     331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT     379
Ala Ala Ser Arg Gly Ala Asn Phe Ile Val Phe Pro Glu Leu Ala Leu
     35                  40                  45
```

```
ACG ACC TTC TTC CCG CGC TGG CTA TTC ACC GAC GAG GCC GAG CTC GAT        427
Thr Thr Phe Phe Pro Arg Trp Leu Phe Thr Asp Glu Ala Glu Leu Asp
 50              55                  60                  65

AGC TTC TAT GAG ACC GAA ATG CCC GGC CCG GTG GTC CGT CCA CTC TTT        475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA        523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG        571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG        619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA        667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC        715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT        763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC        811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC        859
Gly Tyr Asn Thr Pro Thr His Asn Pro Pro Val Pro Gln His Asp His
195                 200                 205

CTG ACG TCC TTC CAC CAT CTC CTA TCG ATG CAG GCC GGG TCT TAT CAG        907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC        955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
275                 280                 285

CAG CAT CGT CAG CCC CAG CAC TAT GGT CTG ATC GCG GAA CTC               1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTC GTTTCGCACC GACGGCCGTC GTGAACTCGA     1321

CAGTCCGCGA GAAGGGCGTA TTGCGCGGCC TGGACCTGTA CGTGGAACTG TAGCCCATAT     1381

ATAGATTTCC AAAGAGTTTC GGCGAGGCGC GGCGCGCCTA GCCCCATGTG AGCGAGAACC     1441

GTGCCCAGAT CAAAGAATGA GACCGACGCG CCGGCCGCGG CAAAGGATGA TCCTCAGGGT     1501

CGGATCTATC GCTCCGCCCT GAAGCAGGAG GGCGCACGCT GGCTGCTGAC GGCGGAGGAA     1561

GGGTTGCTGG CAAAGCCCAA GCCGCCCGGC CTTGTTCCGG CACTTGAGAA TGCGATCGCC     1621
```

```
ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785
```

(2) INFORMATION FOR SEQ ID NO:18:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:18:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
        35                  40                  45

Leu Thr Thr Phe Phe Pro Arg Trp Leu Phe Thr Asp Glu Ala Glu Leu
    50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300
```

(2) INFORMATION FOR SEQ ID NO:19:

(i) SEQUENCE CHARACTERISTICS:
    (A) LENGTH: 1785 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Escherichia coli
    (B) STRAIN: JM109 pAD435

(ix) FEATURE:
    (A) NAME/KEY: CDS
    (B) LOCATION: join(233..1141)

(xi) SEQUENCE DESCRIPTION: SEQ ID NO:19:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                         Thr
                                                         1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
        5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
    20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
35                  40                  45

ACG ACC TTC TTC CCG CGC TGG CTT TTC ACC GAC GAG GCC GAG CTC GAT      427
Thr Thr Phe Phe Pro Arg Trp Leu Phe Thr Asp Glu Ala Glu Leu Asp
50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
            70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
            100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
            150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
            180                 185                 190

GGC TAC AAC ACG CCG ACC CAC AAT CCC CCT GTT CCC CAG CAC GAC CAC      859
Gly Tyr Asn Thr Pro Thr His Asn Pro Pro Val Pro Gln His Asp His
            195                 200                 205
```

-continued

```
CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210             215                 220                 225

AAC GGG GCC TGG TCC GCG GCC GCG GGC AAG GTG GGC ATG GAG GAG AAC      955
Asn Gly Ala Trp Ser Ala Ala Ala Gly Lys Val Gly Met Glu Glu Asn
                    230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
                245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
                260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
                275                 280                 285

CAG CAT CGT CAG CCC CAG CAC TAT GGT CTG ATC GCG GAA CTC             1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG   1201

CCAGGGTGAC GCTGGTGGAA TAGTACCACG ACCGCTTCAG GGCGATCCGC AAGGAGATGC   1261

GGGTCGCCGG AGCGGCAAAG CCCGACATTC GTTTCGCACC GACGGCCGTC GTGAACTCGA   1321

CAGTCCGCGA GAAGGGCGTA TTGCGCGGCC TGGACCTGTA CGTGGAACTG TAGCCCATAT   1381

ATAGATTTCC AAAGAGTTTC GGCGAGGCGC GGCGCGCCTA GCCCCATGTG AGCGAGAACC   1441

GTGCCCAGAT CAAAGAATGA GACCGACGCG CCGGCCGCGG CAAAGGATGA TCCTCAGGGT   1501

CGGATCTATC GCTCCGCCCT GAAGCAGGAG GGCGCACGCT GGCTGCTGAC GGCGGAGGAA   1561

GGGTTGCTGG CAAAGCCCAA GCCGCCCGGC CTTGTTCCGG CACTTGAGAA TGCGATCGCC   1621

ATCGTCGATT ACATCAACGG TACACCGCCC CATATCGCGT CCCTGGCGGA GCTTTCAACG   1681

ACGCTCGGGA TATCCAAGAG CCACTGTCAC TCCATCCTCA AGACGCTGAC GCATTTCGGC   1741

TGGCTGAAAT CGACAATCG CTCAAAGAGC TACGAGCTGA ATTC                    1785
```

(2) INFORMATION FOR SEQ ID NO:20:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:20:

```
Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
                35                  40                  45

Leu Thr Thr Phe Phe Pro Arg Trp Leu Phe Thr Asp Glu Ala Glu Leu
            50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110
```

```
Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300

(2) INFORMATION FOR SEQ ID NO:21:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli
         (B) STRAIN: JM109 pAD439

(ix) FEATURE:
         (A) NAME/KEY: CDS
         (B) LOCATION: join(233..1141)

(xi) SEQUENCE DESCRIPTION: SEQ ID NO:21:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA    120

TGTAGAATTT GCATTGCGCC GCGAGTCACA AAGCCGGTTT TCGGCGATGT GTTTCACAAC    180

GTTTTCCCGG CCGCTGGGCC GGACATCACC TAGGAAGGAG CAGAGGTTCA TG ACA        235
                                                         Thr
                                                          1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
        35                  40                  45
```

-continued

```
ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC      859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210                 215                 220                 225

AAC GGG GCC TGG TCC GCG GCC GCG GGC AAG GCT GGC ATG GAG GAG AAC      955
Asn Gly Ala Trp Ser Ala Ala Ala Gly Lys Ala Gly Met Glu Glu Asn
                230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC             1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG   1201

CCAGGGTGAC GCTGGTGGAA TAGTACCACG ACCGCTTCAG GGCGATCCGC AAGGAGATGC   1261

GGGTCGCCGG AGCGGCAAAG CCCGACATTC GTTTCGCACC GACGGCCGTC GTGAACTCGA   1321

CAGTCCGCGA GAAGGGCGTA TTGCGCGGCC TGGACCTGTA CGTGGAACTG TAGCCCATAT   1381

ATAGATTTCC AAAGAGTTTC GGCGAGGCGC GGCGCGCCTA GCCCCATGTG AGCGAGAACC   1441

GTGCCCAGAT CAAAGAATGA GACCGACGCG CCGGCCGCGG CAAAGGATGA TCCTCAGGGT   1501

CGGATCTATC GCTCCGCCCT GAAGCAGGAG GGCGCACGCT GGCTGCTGAC GGCGGAGGAA   1561
```

-continued

```
GGGTTGCTGG CAAAGCCCAA GCCGCCCGGC CTTGTTCCGG CACTTGAGAA TGCGATCGCC   1621

ATCGTCGATT ACATCAACGG TACACCGCCC CATATCGCGT CCCTGGCGGA GCTTTCAACG   1681

ACGCTCGGGA TATCCAAGAG CCACTGTCAC TCCATCCTCA AGACGCTGAC GCATTTCGGC   1741

TGGCTGAAAT TCGACAATCG CTCAAAGAGC TACGAGCTGA ATTC                    1785
```

(2) INFORMATION FOR SEQ ID NO:22:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:22:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
         35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300
```

(2) INFORMATION FOR SEQ ID NO:23:

(i) SEQUENCE CHARACTERISTICS:
    (A) LENGTH: 1785 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Escherichia coli
    (B) STRAIN: JM109 pAD441

(ix) FEATURE:
    (A) NAME/KEY: CDS
    (B) LOCATION: join(233..1141)

(xi) SEQUENCE DESCRIPTION: SEQ ID NO:23:

```
GTCGACGGCG GGCTCGCGCG AGAGCTTGTC AAGCAGCGCA AATTCCGGTT CCGCTCCGGT          60

TGACAGATCA AAAATTTTAC GCCTGTTATT GTCGTGCTGC ATGTAATATT TCGTACTTTA         120

TGTAGAATTT GCATTGCGCC GCGAGTCACA AAGCCGGTTT TCGGCGATGT GTTTCACAAC         180

GTTTTCCCGG CCGCTGGGCC GGACATCACC TAGGAAGGAG CAGAGGTTCA TG ACA            235
                                                         Thr
                                                          1

CGT CAG ATG ATA CTT GCA GTG GGA CAA CAA GGT CCG ATC GCG CGC GCG          283
Arg Gln Met Ile Leu Ala Val Gly Gln Gln Gly Pro Ile Ala Arg Ala
            5                  10                  15

GAG ACA CGC GAA CAG GTC GTC GTT CGT CTT CTC GAC ATG CTG ACG AAA          331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT          379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT          427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT          475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA          523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG          571
Leu Val Val Glu Gly Gly Val Lys Arg Arg Phe Asn Thr Ser Ile Leu
    100                 105                 110

GTG GAT AAG TCA GGC AAG ATC GTC GGC AAG TAT CGT AAG ATC CAT TTG          619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA          667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC          715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT          763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC          811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC          859
Gly Tyr Asn Thr Pro Thr His Asn Pro Pro Val Pro Gln His Asp His
```

```
                                                                    -continued
        195                     200                     205
CTG ACG TCC TTC CAC CAT CTC CTA TCG ATG CAG GCC GGG TCT TAT CAG       907
Leu Thr Ser Phe His His Leu Leu Ser Met Gln Ala Gly Ser Tyr Gln
210                     215                     220             225

AAC GGG GCC TGG TCC GCG GCC GCG GGC AAG AGT GGC ATG GAG GAG AAC       955
Asn Gly Ala Trp Ser Ala Ala Ala Gly Lys Ser Gly Met Glu Glu Asn
                    230                     235                 240

TGC ATG CTG CTC GGC CAC TCC TGC ATC GTG GCG CCG ACC GGG GAA ATC      1003
Cys Met Leu Leu Gly His Ser Cys Ile Val Ala Pro Thr Gly Glu Ile
                245                     250                 255

GTC GCT CTC ACT ACG ACG CTG GAA GAC GAG GTG ATC ACC GCC GCC GTC      1051
Val Ala Leu Thr Thr Thr Leu Glu Asp Glu Val Ile Thr Ala Ala Val
            260                     265                 270

GAT CTC GAT CGC TGC CGG GAA CTG CGT GAA CAC ATC TTC AAC TTC AAG      1099
Asp Leu Asp Arg Cys Arg Glu Leu Arg Glu His Ile Phe Asn Phe Lys
        275                     280                 285

CAG CAT CGT CAG CCC CAG CAC TAT GGT CTG ATC GCG GAA CTC              1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG    1201

CCAGGGTGAC GCTGGTGGAA TAGTACCACG ACCGCTTCAG GGCGATCCGC AAGGAGATGC    1261

GGGTCGCCGG AGCGGCAAAG CCCGACATTC GTTTCGCACC GACGGCCGTC GTGAACTCGA    1321

CAGTCCGCGA GAAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785

(2) INFORMATION FOR SEQ ID NO:24:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:24:

Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
             35                  40                  45

Leu Thr Thr Phe Phe Pro Arg Trp His Phe Thr Asp Glu Ala Glu Leu
 50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
```

-continued

```
                100                 105                 110
Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ser Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300
```

(2) INFORMATION FOR SEQ ID NO:25:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD445

(ix) FEATURE:
        (A) NAME/KEY: CDS
        (B) LOCATION: join(233..1141)

(xi) SEQUENCE DESCRIPTION: SEQ ID NO:25:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                          Thr
                                                            1

CGT CAG ATG ATA CTT GCA GTG GGA CAA CAA GGT CCG ATC GCG CGC GCG       283
Arg Gln Met Ile Leu Ala Val Gly Gln Gln Gly Pro Ile Ala Arg Ala
        5                  10                  15

GAG ACA CGC GAA CAG GTC GTC GTT CGT CTT CTC GAC ATG CTG ACG AAA       331
Glu Thr Arg Glu Gln Val Val Val Arg Leu Leu Asp Met Leu Thr Lys
    20                  25                  30

GCC GCG AGC CGG GGC GCG AAT TTC ATT GTC TTC CCC GAA CTC GCG CTT       379
Ala Ala Ser Arg Gly Ala Asn Phe Ile Val Phe Pro Glu Leu Ala Leu
```

```
                35                        40                         45
ACG ACC TTC TTC CCG CGC TGG CAT TTC ACC GAC GAG GCC GAG CTC GAT        427
Thr Thr Phe Phe Pro Arg Trp His Phe Thr Asp Glu Ala Glu Leu Asp
 50                   55                      60                  65

AGC TTC TAT GAG ACC GAA ATG CCC GGC CCG GTG GTC CGT CCA CTC TTT        475
Ser Phe Tyr Glu Thr Glu Met Pro Gly Pro Val Val Arg Pro Leu Phe
                 70                      75                  80

GAG AAG GCC GCG GAA CTC GGG ATC GGC TTC AAT CTG GGC TAC GCT GAA        523
Glu Lys Ala Ala Glu Leu Gly Ile Gly Phe Asn Leu Gly Tyr Ala Glu
             85                      90                  95

CTC GTC GTC GAA GGC GGC GTC AAG CGT CGC TTC AAC ACG TCC ATT TTG        571
Leu Val Val Glu Gly Gly Val Lys Arg Arg Phe Asn Thr Ser Ile Leu
            100                     105                 110

GTG GAT AAG TCA GGC AAG ATC GTC GGC AAG TAT CGT AAG ATC CAT TTG        619
Val Asp Lys Ser Gly Lys Ile Val Gly Lys Tyr Arg Lys Ile His Leu
        115                     120                 125

CCG GGT CAC AAG GAG TAC GAG GCC TAC CGG CCG TTC CAG CAT CTT GAA        667
Pro Gly His Lys Glu Tyr Glu Ala Tyr Arg Pro Phe Gln His Leu Glu
130                     135                 140                 145

AAG CGT TAT TTC GAG CCG GGC GAT CTC GGC TTC CCG GTC TAT GAC GTC        715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT        763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC        811
Glu Ala Trp Arg Val Met Gly Leu Arg Gly Ala Glu Ile Ile Cys Gly
            180                 185                 190

GGC TAC AAC ACG CCG ACC CAC AAT CCC ACC GTT CCC CAG CAC GAC CAC        859
Gly Tyr Asn Thr Pro Thr His Asn Pro Thr Val Pro Gln His Asp His
        195                 200                 205

CTG ACG TCC TTC CAC CAT CTC CTA TCG ATG CAG GCC GGG TCT TAT CAG        907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC        955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
            260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
        275                 280                 285

CAG CAT CGT CAG CCC CAG CAC TAT GGT CTG ATC GCG GAA CTC               1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTC GTTTCGCACC GACGGCCGTC GTGAACTCGA     1321

CAGTCCGCGA AAGGGCGTA TTGCGCGGCC TGGACCTGTA CGTGGAACTG TAGCCCATAT      1381

ATAGATTTCC AAAGAGTTTC GGCGAGGCGC GGCGCGCCTA GCCCCATGTG AGCGAGAACC     1441

GTGCCCAGAT CAAAGAATGA GACCGACGCG CCGGCCGCGG CAAAGGATGA TCCTCAGGGT     1501

CGGATCTATC GCTCCGCCCT GAAGCAGGAG GGCGCACGCT GGCTGCTGAC GGCGGAGGAA     1561
```

-continued

```
GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785
```

(2) INFORMATION FOR SEQ ID NO:26:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:26:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
                 20                  25                  30

Lys Ala Ala Ser Arg Gly Ala Asn Phe Ile Val Phe Pro Glu Leu Ala
             35                  40                  45

Leu Thr Thr Phe Phe Pro Arg Trp His Phe Thr Asp Glu Ala Glu Leu
 50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Thr Val Pro Gln His Asp
        195                 200                 205

His Leu Thr Ser Phe His His Leu Leu Ser Met Gln Ala Gly Ser Tyr
210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
275                 280                 285

Lys Gln His Arg Gln Pro Gln His Tyr Gly Leu Ile Ala Glu Leu
290                 295                 300
```

(2) INFORMATION FOR SEQ ID NO:27:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD447

(ix) FEATURE:
        (A) NAME/KEY: CDS
        (B) LOCATION: join(233..1141)

(xi) SEQUENCE DESCRIPTION: SEQ ID NO:27:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                         Thr
                                                          1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
     20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
    100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
        180                 185                 190

GGC TAC AAC ACG CCG ACC CAC AAT CCC CCT GTT CCC CAG CAC GAC CAC      859
```

```
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG        907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCA GGC ATG GAG GAG AAC        955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC               1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTC GTTTCGCACC GACGGCCGTC GTGAACTCGA     1321

CAGTCCGCGA GAAGGGCGTA TTGCGCGGCC TGGACCTGTA CGTGGAACTG TAGCCCATAT     1381

ATAGATTTCC AAAGAGTTTC GGCGAGGCGC GGCGCGCCTA GCCCCATGTG AGCGAGAACC     1441

GTGCCCAGAT CAAAGAATGA GACCGACGCG CCGGCCGCGG CAAAGGATGA TCCTCAGGGT     1501

CGGATCTATC GCTCCGCCCT GAAGCAGGAG GGCGCACGCT GGCTGCTGAC GGCGGAGGAA     1561

GGGTTGCTGG CAAAGCCCAA GCCGCCCGGC CTTGTTCCGG CACTTGAGAA TGCGATCGCC     1621

ATCGTCGATT ACATCAACGG TACACCGCCC CATATCGCGT CCCTGGCGGA GCTTTCAACG     1681

ACGCTCGGGA TATCCAAGAG CCACTGTCAC TCCATCCTCA AGACGCTGAC GCATTTCGGC     1741

TGGCTGAAAT TCGACAATCG CTCAAAGAGC TACGAGCTGA ATTC                      1785
```

(2) INFORMATION FOR SEQ ID NO:28:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:28:

```
Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
        35                  40                  45

Leu Thr Thr Phe Phe Pro Arg Trp His Phe Thr Asp Glu Ala Glu Leu
    50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95
```

```
Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ser Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300

(2) INFORMATION FOR SEQ ID NO:29:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD448

(ix) FEATURE:
        (A) NAME/KEY: CDS
        (B) LOCATION: join(233..1141)

(xi) SEQUENCE DESCRIPTION: SEQ ID NO:29:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                        Thr
                                                         1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
         20                 25                  30

GCC GCG AGC CGG GGC GCG AAT TTC ATT GTC TTC CCC GAA CTC GCG CTT      379
```

```
Ala Ala Ser Arg Gly Ala Asn Phe Ile Val Phe Pro Glu Leu Ala Leu
         35                  40                  45

ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
         100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
     115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                 150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
             165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
         180                 185                 190

GGC TAC AAC ACG CCG ACC CAC AAT CCC CCT GTT CCC CAG CAC GAC CAC      859
Gly Tyr Asn Thr Pro Thr His Asn Pro Pro Val Pro Gln His Asp His
     195                 200                 205

CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCG GGC ATG GAG GAG AAC      955
Asn Gly Ala Trp Ser Ala Ala Ala Gly Lys Ser Gly Met Glu Glu Asn
                 230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
             245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
         260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
     275                 280                 285

CAG CAT CGT CAG CCC CAG CAC TAT GGT CTG ATC GCG GAA CTC              1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG   1201

CCAGGGTGAC GCTGGTGGAA TAGTACCACG ACCGCTTCAG GGCGATCCGC AAGGAGATGC   1261

GGGTCGCCGG AGCGGCAAAG CCCGACATTC GTTTCGCACC GACGGCCGTC GTGAACTCGA   1321

CAGTCCGCGA GAAGGGCGTA TTGCGCGGCC TGGACCTGTA CGTGGAACTG TAGCCCATAT   1381

ATAGATTTCC AAAGAGTTTC GGCGAGGCGC GGCGCGCCTA GCCCCATGTG AGCGAGAACC   1441

GTGCCCAGAT CAAAGAATGA GACCGACGCG CCGGCCGCGG CAAAGGATGA TCCTCAGGGT   1501
```

```
CGGATCTATC GCTCCGCCCT GAAGCAGGAG GGCGCACGCT GGCTGCTGAC GGCGGAGGAA     1561

GGGTTGCTGG CAAAGCCCAA GCCGCCCGGC CTTGTTCCGG CACTTGAGAA TGCGATCGCC     1621

ATCGTCGATT ACATCAACGG TACACCGCCC CATATCGCGT CCCTGGCGGA GCTTTCAACG     1681

ACGCTCGGGA TATCCAAGAG CCACTGTCAC TCCATCCTCA AGACGCTGAC GCATTTCGGC     1741

TGGCTGAAAT TCGACAATCG CTCAAAGAGC TACGAGCTGA ATTC                      1785
```

(2) INFORMATION FOR SEQ ID NO:30:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:30:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
             35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
                115                 120                 125

Leu Pro Gly His Lys Glu Tyr Glu Ala Tyr Arg Pro Phe Gln His Leu
            130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Val Pro Gln His Asp
                195                 200                 205

His Leu Thr Ser Phe His His Leu Leu Ser Met Gln Ala Gly Ser Tyr
            210                 215                 220

Gln Asn Gly Ala Trp Ser Ala Ala Ala Gly Lys Ser Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
290                 295                 300
```

(2) INFORMATION FOR SEQ ID NO:31:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD450

(ix) FEATURE:
        (A) NAME/KEY: CDS
        (B) LOCATION: join(233..1141)

(xi) SEQUENCE DESCRIPTION: SEQ ID NO:31:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                         Thr
                                                          1

CGT CAG ATG ATA CTT GCA GTG GGA CAA CAA GGT CCG ATC GCG CGC GCG       283
Arg Gln Met Ile Leu Ala Val Gly Gln Gln Gly Pro Ile Ala Arg Ala
              5                  10                  15

GAG ACA CGC GAA CAG GTC GTC GTT CGT CTT CTC GAC ATG CTG ACG AAA       331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT       379
Ala Ala Ser Arg Gly Ala Asn Phe Ile Val Phe Pro Glu Leu Ala Leu
     35                  40                  45

ACG ACC TTC TTC CCG CGC TGG CAT TTC ACC GAC GAG GCC GAG CTC GAT       427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT       475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA       523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG       571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG       619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA       667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC       715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT       763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC       811
Glu Ala Trp Arg Val Met Gly Leu Arg Gly Ala Glu Ile Ile Cys Gly
        180                 185                 190
```

```
GGC TAC AAC ACG CCG ACC CAC AAT CCC CCT GTT CCC CAG CAC GAC CAC        859
Gly Tyr Asn Thr Pro Thr His Asn Pro Pro Val Pro Gln His Asp His
    195                 200                 205

CTG ACG TCC TTC CAC CAT CTC CTA TCG ATG CAG GCC GGG TCT TAT CAG        907
Leu Thr Ser Phe His His Leu Leu Ser Met Gln Ala Gly Ser Tyr Gln
210                 215                 220                 225

AAC GGG GCC TGG TCC GCG GCC GCG GGC AAG ACG GGC ATG GAG GAG AAC        955
Asn Gly Ala Trp Ser Ala Ala Ala Gly Lys Thr Gly Met Glu Glu Asn
                230                 235                 240

TGC ATG CTG CTC GGC CAC TCC TGC ATC GTG GCG CCG ACC GGG GAA ATC       1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC       1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG       1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC               1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTG GTTTCGCACC GACGGCCGTC GTGAACTCGA     1321

CAGTCCGCGA GAAGGGCGTA TTGCGCGGCC TGGACCTGTA CGTGGAACTG TAGCCCATAT     1381

ATAGATTTCC AAAGAGTTTC GGCGAGGCGC GGCGCGCCTA GCCCCATGTG AGCGAGAACC     1441

GTGCCCAGAT CAAAGAATGA GACCGACGCG CCGGCCGCGG CAAAGGATGA TCCTCAGGGT     1501

CGGATCTATC GCTCCGCCCT GAAGCAGGAG GGCGCACGCT GGCTGCTGAC GGCGGAGGAA     1561

GGGTTGCTGG CAAAGCCCAA GCCGCCCGGC CTTGTTCCGG CACTTGAGAA TGCGATCGCC     1621

ATCGTCGATT ACATCAACGG TACACCGCCC CATATCGCGT CCCTGGCGGA GCTTTCAACG     1681

ACGCTCGGGA TATCCAAGAG CCACTGTCAC TCCATCCTCA AGACGCTGAC GCATTTCGGC     1741

TGGCTGAAAT TCGACAATCG CTCAAAGAGC TACGAGCTGA ATTC                      1785

(2) INFORMATION FOR SEQ ID NO:32:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:32:

Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95
```

```
Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Pro Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Thr Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300

(2) INFORMATION FOR SEQ ID NO:33:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD421

(ix) FEATURE:
        (A) NAME/KEY: CDS
        (B) LOCATION: join(7..915)

(xi) SEQUENCE DESCRIPTION: SEQ ID NO:33:

CATATG ACA CGT CAG ATG ATA CTT GCA GTG GGA CAA CAA GGT CCG ATC        48
       Thr Arg Gln Met Ile Leu Ala Val Gly Gln Gln Gly Pro Ile
        1               5                   10

GCG CGC GCG GAG ACA CGC GAA CAG GTC GTC GTT CGT CTT CTC GAC ATG        96
Ala Arg Ala Glu Thr Arg Glu Gln Val Val Val Arg Leu Leu Asp Met
 15                  20                  25                  30

CTG ACG AAA GCC GCG AGC CGG GGC GCG AAT TTC ATT GTC TTC CCC GAA       144
Leu Thr Lys Ala Ala Ser Arg Gly Ala Asn Phe Ile Val Phe Pro Glu
                 35                  40                  45

CTC GCG CTT ACG ACC TTC TTC CCG CGC TGG TAT TTC ACC GAC GAG GCC       192
Leu Ala Leu Thr Thr Phe Phe Pro Arg Trp Tyr Phe Thr Asp Glu Ala
             50                  55                  60

GAG CTC GAT AGC TTC TAT GAG ACC GAA ATG CCC GGC CCG GTG GTC CGT       240
Glu Leu Asp Ser Phe Tyr Glu Thr Glu Met Pro Gly Pro Val Val Arg
```

-continued

```
              65                   70                      75
CCA CTC TTT GAG AAG GCC GCG GAA CTC GGG ATC GGC TTC AAT CTG GGC        288
Pro Leu Phe Glu Lys Ala Ala Glu Leu Gly Ile Gly Phe Asn Leu Gly
         80                  85                  90

TAC GCT GAA CTC GTC GTC GAA GGC GGC GTC AAG CGT CGC TTC AAC ACG        336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG        384
Ser Ile Leu Val Asp Lys Ser Gly Lys Ile Val Gly Lys Tyr Arg Lys
                    115                 120                 125

ATC CAT TTG CCG GGT CAC AAG GAG TAC GAG GCC TAC CGG CCG TTC CAG        432
Ile His Leu Pro Gly His Lys Glu Tyr Glu Ala Tyr Arg Pro Phe Gln
                130                 135                 140

CAT CTT GAA AAG CGT TAT TTC GAG CCG GGC GAT CTC GGC TTC CCG GTC        480
His Leu Glu Lys Arg Tyr Phe Glu Pro Gly Asp Leu Gly Phe Pro Val
            145                 150                 155

TAT GAC GTC GAC GCC GCG AAA ATG GGG ATG TTC ATC TGC AAC GAT CGC        528
Tyr Asp Val Asp Ala Ala Lys Met Gly Met Phe Ile Cys Asn Asp Arg
        160                 165                 170

CGC TGG CCT GAA GCC TGG CGG GTG ATG GGC CTC AGG GGC GCC GAG ATC        576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC CTT GTT CCC CAG        624
Ile Cys Gly Gly Tyr Asn Thr Pro Thr His Asn Pro Leu Val Pro Gln
                    195                 200                 205

CAC GAC CAC CTG ACG TCC TTC CAC CAT CTC CTA TCG ATG CAG GCC GGG        672
His Asp His Leu Thr Ser Phe His His Leu Leu Ser Met Gln Ala Gly
                210                 215                 220

TCT TAT CAG AAC GGG GCC TGG TCC GCG GCC GCG GGC AAG GTG GGC ATG        720
Ser Tyr Gln Asn Gly Ala Trp Ser Ala Ala Ala Gly Lys Val Gly Met
            225                 230                 235

GAG GAG AAC TGC ATG CTG CTC GGC CAC TCC TGC ATC GTG GCG CCG ACC        768
Glu Glu Asn Cys Met Leu Leu Gly His Ser Cys Ile Val Ala Pro Thr
        240                 245                 250

GGG GAA ATC GTC GCT CTC ACT ACG ACG CTG GAA GAC GAG GTG ATC ACC        816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC        864
Ala Ala Val Asp Leu Asp Arg Cys Arg Glu Leu Arg Glu His Ile Phe
                    275                 280                 285

AAC TTC AAG CAG CAT CGT CAG CCC CAG CAC TAT GGT CTG ATC GCG GAA        912
Asn Phe Lys Gln His Arg Gln Pro Gln His Tyr Gly Leu Ile Ala Glu
                290                 295                 300

CTC TGAGGTTGCC GAAAAGCATG TGTGTCGTTG TTCTCGGCGC CTGGGTCACA             965
Leu

TCCAGGCGCG CCAGGGTGAC GCTGGTGGAA TAGTACCACG ACCGCTTCAG GGCGATCCGC     1025

AAGGAGATGC GGGTCGCCGG AGCGGCAAAG CCCGACATTC GTTTCGCACC GACGGCCGTC     1085

GTGAACTCGA CAGTCCGCGA GAAGGGCGTA TTGCGCGGCC TGGACCTGTA CGTGGAACTG     1145

TAGCCCATAT ATAGATTTCC AAAGAGTTTC GGCGAGGCGG GCGCGCCTA GCCCCATGTG       1205

AGCGAGAACC GTGCCCAGAT CAAAGAATGA GACCGACGCG CCGGCCGCGG CAAAGGATGA     1265

TCCTCAGGGT CGGATCTATC GCTCCGCCCT GAAGCAGGAG GGCGCACGCT GGCTGCTGAC     1325

GGCGGAGGAA GGGTTGCTGG CAAAGCCCAA GCCGCCCGGC CTTGTTCCGG CACTTGAGAA     1385

TGCGATCGCC ATCGTCGATT ACATCAACGG TACACCGCCC CATATCGCGT CCCTGGCGGA     1445

GCTTTCAACG ACGCTCGGGA TATCCAAGAG CCACTGTCAC TCCATCCTCA AGACGCTGAC     1505
```

GCATTTCGGC TGGCTGAAAT TCGACAATCG CTCAAAGAGC TACGAGCTGA ATTC        1559

(2) INFORMATION FOR SEQ ID NO:34:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:34:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp Tyr Phe Thr Asp Glu Ala Glu Leu
 50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Leu Val Pro Gln His Asp
            195                 200                 205

His Leu Thr Ser Phe His His Leu Leu Ser Met Gln Ala Gly Ser Tyr
210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
290                 295                 300
```

(2) INFORMATION FOR SEQ ID NO:35:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD422

(ix) FEATURE:
        (A) NAME/KEY: CDS
        (B) LOCATION: join(7..915)

(xi) SEQUENCE DESCRIPTION: SEQ ID NO:35:

```
CATATG ACA CGT CAG ATG ATA CTT GCA GTG GGA CAA CAA GGT CCG ATC          48
       Thr Arg Gln Met Ile Leu Ala Val Gly Gln Gln Gly Pro Ile
         1               5                  10

GCG CGC GCG GAG ACA CGC GAA CAG GTC GTC GTT CGT CTT CTC GAC ATG         96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA        144
Leu Thr Lys Ala Ala Ser Arg Gly Ala Asn Phe Ile Val Phe Pro Glu
             35                  40                  45

CTC GCG CTT ACG ACC TTC TTC CCG CGC TGG TAT TTC ACC GAC GAG GCC        192
Leu Ala Leu Thr Thr Phe Phe Pro Arg Trp Tyr Phe Thr Asp Glu Ala
                 50                  55                  60

GAG CTC GAT AGC TTC TAT GAG ACC GAA ATG CCC GGC CCG GTG GTC CGT        240
Glu Leu Asp Ser Phe Tyr Glu Thr Glu Met Pro Gly Pro Val Val Arg
                     65                  70                  75

CCA CTC TTT GAG AAG GCC GCG GAA CTC GGG ATC GGC TTC AAT CTG GGC        288
Pro Leu Phe Glu Lys Ala Ala Glu Leu Gly Ile Gly Phe Asn Leu Gly
                         80                  85                  90

TAC GCT GAA CTC GTC GTC GAA GGC GGC GTC AAG CGT CGC TTC AAC ACG        336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG        384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG        432
Ile His Leu Pro Gly His Lys Glu Tyr Glu Ala Tyr Arg Pro Phe Gln
                    130                 135                 140

CAT CTT GAA AAG CGT TAT TTC GAG CCG GGC GAT CTC GGC TTC CCG GTC        480
His Leu Glu Lys Arg Tyr Phe Glu Pro Gly Asp Leu Gly Phe Pro Val
                145                 150                 155

TAT GAC GTC GAC GCC GCG AAA ATG GGG ATG TTC ATC TGC AAC GAT CGC        528
Tyr Asp Val Asp Ala Ala Lys Met Gly Met Phe Ile Cys Asn Asp Arg
160                 165                 170

CGC TGG CCT GAA GCC TGG CGG GTG ATG GGC CTC AGG GGC GCC GAG ATC        576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC TCT GTT CCC CAG        624
Ile Cys Gly Gly Tyr Asn Thr Pro Thr His Asn Pro Ser Val Pro Gln
                    195                 200                 205

CAC GAC CAC CTG ACG TCC TTC CAC CAT CTC CTA TCG ATG CAG GCC GGG        672
His Asp His Leu Thr Ser Phe His His Leu Leu Ser Met Gln Ala Gly
                        210                 215                 220

TCT TAT CAG AAC GGG GCC TGG TCC GCG GCC GCG GGC AAG GTG GGC ATG        720
Ser Tyr Gln Asn Gly Ala Trp Ser Ala Ala Ala Gly Lys Val Gly Met
                225                 230                 235

GAG GAG AAC TGC ATG CTG CTC GGC CAC TCC TGC ATC GTG GCG CCG ACC        768
Glu Glu Asn Cys Met Leu Leu Gly His Ser Cys Ile Val Ala Pro Thr
240                 245                 250

GGG GAA ATC GTC GCT CTC ACT ACG ACG CTG GAA GAC GAG GTG ATC ACC        816
Gly Glu Ile Val Ala Leu Thr Thr Thr Leu Glu Asp Glu Val Ile Thr
```

```
                    255                 260                 265                 270
GCC GCC GTC GAT CTC GAT CGC TGC CGG GAA CTG CGT GAA CAC ATC TTC              864
Ala Ala Val Asp Leu Asp Arg Cys Arg Glu Leu Arg Glu His Ile Phe
                        275                 280                 285

AAC TTC AAG CAG CAT CGT CAG CCC CAG CAC TAT GGT CTG ATC GCG GAA              912
Asn Phe Lys Gln His Arg Gln Pro Gln His Tyr Gly Leu Ile Ala Glu
                290                 295                 300

CTC TGAGGTTGCC GAAAAGCATG TGTGTCGTTG TTCTCGGCGC CTGGGTCACA                   965
Leu

TCCAGGCGCG CCAGGGTGAC GCTGGTGGAA TAGTACCACG ACCGCTTCAG GGCGATCCGC           1025

AAGGAGATGC GGGTCGCCGG AGCGGCAAAG CCCGACATTC GTTTCGCACC GACGGCCGTC           1085

GTGAACTCGA CAGTCCGCGA GAAGGGCGTA TTGCGCGGCC TGGACCTGTA CGTGGAACTG           1145

TAGCCCATAT ATAGATTTCC AAAGAGTTTC GGCGAGGCGC GGCGCGCCTA GCCCCATGTG           1205

AGCGAGAACC GTGCCCAGAT CAAAGAATGA GACCGACGCG CCGGCCGCGG CAAAGGATGA           1265

TCCTCAGGGT CGGATCTATC GCTCCGCCCT GAAGCAGGAG GGCGCACGCT GGCTGCTGAC           1325

GGCGGAGGAA GGGTTGCTGG CAAAGCCCAA GCCGCCCGGC CTTGTTCCGG CACTTGAGAA           1385

TGCGATCGCC ATCGTCGATT ACATCAACGG TACACCGCCC CATATCGCGT CCCTGGCGGA           1445

GCTTTCAACG ACGCTCGGGA TATCCAAGAG CCACTGTCAC TCCATCCTCA AGACGCTGAC           1505

GCATTTCGGC TGGCTGAAAT TCGACAATCG CTCAAAGAGC TACGAGCTGA ATTC                 1559
```

(2) INFORMATION FOR SEQ ID NO:36:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:36:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
                 20                  25                  30

Lys Ala Ala Ser Arg Gly Ala Asn Phe Ile Val Phe Pro Glu Leu Ala
                 35                  40                  45

Leu Thr Thr Phe Phe Pro Arg Trp Tyr Phe Thr Asp Glu Ala Glu Leu
         50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                     85                  90                  95

Glu Leu Val Val Glu Gly Val Lys Arg Arg Phe Asn Thr Ser Ile
                100                 105                 110

Leu Val Asp Lys Ser Gly Lys Ile Val Gly Lys Tyr Arg Lys Ile His
                115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                    165                 170                 175

Pro Glu Ala Trp Arg Val Met Gly Leu Arg Gly Ala Glu Ile Ile Cys
```

```
                        180                 185                 190
Gly Gly Tyr Asn Thr Pro Thr His Asn Pro Ser Val Pro Gln His Asp
            195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
    290                 295                 300
```

(2) INFORMATION FOR SEQ ID NO:37:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD423

(ix) FEATURE:
        (A) NAME/KEY: CDS
        (B) LOCATION: join(7..915)

(xi) SEQUENCE DESCRIPTION: SEQ ID NO:37:

```
CATATG ACA CGT CAG ATG ATA CTT GCA GTG GGA CAA CAA GGT CCG ATC        48
       Thr Arg Gln Met Ile Leu Ala Val Gly Gln Gln Gly Pro Ile
        1               5                  10

GCG CGC GCG GAG ACA CGC GAA CAG GTC GTC GTT CGT CTT CTC GAC ATG       96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA      144
Leu Thr Lys Ala Ala Ser Arg Gly Ala Asn Phe Ile Val Phe Pro Glu
                 35                  40                  45

CTC GCG CTT ACG ACC TTC TTC CCG CGC TGG TAT TTC ACC GAC GAG GCC      192
Leu Ala Leu Thr Thr Phe Phe Pro Arg Trp Tyr Phe Thr Asp Glu Ala
                 50                  55                  60

GAG CTC GAT AGC TTC TAT GAG ACC GAA ATG CCC GGC CCG GTG GTC CGT      240
Glu Leu Asp Ser Phe Tyr Glu Thr Glu Met Pro Gly Pro Val Val Arg
             65                  70                  75

CCA CTC TTT GAG AAG GCC GCG GAA CTC GGG ATC GGC TTC AAT CTG GGC      288
Pro Leu Phe Glu Lys Ala Ala Glu Leu Gly Ile Gly Phe Asn Leu Gly
         80                  85                  90

TAC GCT GAA CTC GTC GTC GAA GGC GGC GTC AAG CGT CGC TTC AAC ACG      336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG      384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG      432
Ile His Leu Pro Gly His Lys Glu Tyr Glu Ala Tyr Arg Pro Phe Gln
                130                 135                 140
```

```
CAT CTT GAA AAG CGT TAT TTC GAG CCG GGC GAT CTC GGC TTC CCG GTC      480
His Leu Glu Lys Arg Tyr Phe Glu Pro Gly Asp Leu Gly Phe Pro Val
            145                 150                 155

TAT GAC GTC GAC GCC GCG AAA ATG GGG ATG TTC ATC TGC AAC GAT CGC      528
Tyr Asp Val Asp Ala Ala Lys Met Gly Met Phe Ile Cys Asn Asp Arg
        160                 165                 170

CGC TGG CCT GAA GCC TGG CGG GTG ATG GGC CTC AGG GGC GCC GAG ATC      576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC CCT GTT CCC CAG      624
Ile Cys Gly Gly Tyr Asn Thr Pro Thr His Asn Pro Pro Val Pro Gln
                195                 200                 205

CAC GAC CAC CTG ACG TCC TTC CAC CAT CTC CTA TCG ATG CAG GCC GGG      672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG      720
Ser Tyr Gln Asn Gly Ala Trp Ser Ala Ala Ala Gly Lys Ala Gly Met
        225                 230                 235

GAG GAG AAC TGC ATG CTG CTC GGC CAC TCC TGC ATC GTG GCG CCG ACC      768
Glu Glu Asn Cys Met Leu Leu Gly His Ser Cys Ile Val Ala Pro Thr
    240                 245                 250

GGG GAA ATC GTC GCT CTC ACT ACG ACG CTG GAA GAC GAG GTG ATC ACC      816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC      864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA      912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA           965
Leu

TCCAGGCGCG CCAGGGTGAC GCTGGTGGAA TAGTACCACG ACCGCTTCAG GGCGATCCGC   1025

AAGGAGATGC GGGTCGCCGG AGCGGCAAAG CCCGACATTC GTTTCGCACC GACGGCCGTC   1085

GTGAACTCGA CAGTCCGCGA GAAGGGCGTA TTGCGCGGCC TGGACCTGTA CGTGGAACTG   1145

TAGCCCATAT ATAGATTTCC AAAGAGTTTC GGCGAGGCGC GGCGCGCCTA GCCCCATGTG   1205

AGCGAGAACC GTGCCCAGAT CAAAGAATGA GACCGACGCG CCGGCCGCGG CAAAGGATGA   1265

TCCTCAGGGT CGGATCTATC GCTCCGCCCT GAAGCAGGAG GGCGCACGCT GGCTGCTGAC   1325

GGCGGAGGAA GGGTTGCTGG CAAAGCCCAA GCCGCCCGGC CTTGTTCCGG CACTTGAGAA   1385

TGCGATCGCC ATCGTCGATT ACATCAACGG TACACCGCCC CATATCGCGT CCCTGGCGGA   1445

GCTTTCAACG ACGCTCGGGA TATCCAAGAG CCACTGTCAC TCCATCCTCA AGACGCTGAC   1505

GCATTTCGGC TGGCTGAAAT TCGACAATCG CTCAAAGAGC TACGAGCTGA ATTC        1559
```

(2) INFORMATION FOR SEQ ID NO:38:

(i) SEQUENCE CHARACTERISTICS:
    (A) LENGTH: 303 amino acids
    (B) TYPE: amino acid
    (D) TOPOLOGY: linear (ii) MOLECULE TYPE: protein (xi) SEQUENCE DESCRIPTION: SEQ ID NO:38:

```
Thr Arg Gln Met Ile Leu Ala Val Gly Gln Gln Gly Pro Ile Ala Arg
 1               5                  10                  15
```

```
Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
        35                  40                  45

Leu Thr Thr Phe Phe Pro Arg Trp Tyr Phe Thr Asp Glu Ala Glu Leu
    50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Pro Val Pro Gln His Asp
            195                 200                 205

His Leu Thr Ser Phe His His Leu Leu Ser Met Gln Ala Gly Ser Tyr
        210                 215                 220

Gln Asn Gly Ala Trp Ser Ala Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
290                 295                 300

(2) INFORMATION FOR SEQ ID NO:39:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD424 (FERM BP-4034)

(ix) FEATURE:
        (A) NAME/KEY: CDS
        (B) LOCATION: join(7..915)

(xi) SEQUENCE DESCRIPTION: SEQ ID NO:39:

CATATG ACA CGT CAG ATG ATA CTT GCA GTG GGA CAA CAA GGT CCG ATC        48
       Thr Arg Gln Met Ile Leu Ala Val Gly Gln Gln Gly Pro Ile
        1               5                  10
```

```
GCG CGC GCG GAG ACA CGC GAA CAG GTC GTC GTT CGT CTT CTC GAC ATG        96
Ala Arg Ala Glu Thr Arg Glu Gln Val Val Val Arg Leu Leu Asp Met
 15              20              25              30

CTG ACG AAA GCC GCG AGC CGG GGC GCG AAT TTC ATT GTC TTC CCC GAA       144
Leu Thr Lys Ala Ala Ser Arg Gly Ala Asn Phe Ile Val Phe Pro Glu
         35              40              45

CTC GCG CTT ACG ACC TTC TTC CCG CGC TGG CAT TTC ACC GAC GAG GCC       192
Leu Ala Leu Thr Thr Phe Phe Pro Arg Trp His Phe Thr Asp Glu Ala
     50              55              60

GAG CTC GAT AGC TTC TAT GAG ACC GAA ATG CCC GGC CCG GTG GTC CGT       240
Glu Leu Asp Ser Phe Tyr Glu Thr Glu Met Pro Gly Pro Val Val Arg
         65              70              75

CCA CTC TTT GAG AAG GCC GCG GAA CTC GGG ATC GGC TTC AAT CTG GGC       288
Pro Leu Phe Glu Lys Ala Ala Glu Leu Gly Ile Gly Phe Asn Leu Gly
 80              85              90

TAC GCT GAA CTC GTC GTC GAA GGC GGC GTC AAG CGT CGC TTC AAC ACG       336
Tyr Ala Glu Leu Val Val Glu Gly Gly Val Lys Arg Arg Phe Asn Thr
 95             100             105             110

TCC ATT TTG GTG GAT AAG TCA GGC AAG ATC GTC GGC AAG TAT CGT AAG       384
Ser Ile Leu Val Asp Lys Ser Gly Lys Ile Val Gly Lys Tyr Arg Lys
            115             120             125

ATC CAT TTG CCG GGT CAC AAG GAG TAC GAG GCC TAC CGG CCG TTC CAG       432
Ile His Leu Pro Gly His Lys Glu Tyr Glu Ala Tyr Arg Pro Phe Gln
            130             135             140

CAT CTT GAA AAG CGT TAT TTC GAG CCG GGC GAT CTC GGC TTC CCG GTC       480
His Leu Glu Lys Arg Tyr Phe Glu Pro Gly Asp Leu Gly Phe Pro Val
        145             150             155

TAT GAC GTC GAC GCC GCG AAA ATG GGG ATG TTC ATC TGC AAC GAT CGC       528
Tyr Asp Val Asp Ala Ala Lys Met Gly Met Phe Ile Cys Asn Asp Arg
160             165             170

CGC TGG CCT GAA GCC TGG CGG GTG ATG GGC CTC AGG GGC GCC GAG ATC       576
Arg Trp Pro Glu Ala Trp Arg Val Met Gly Leu Arg Gly Ala Glu Ile
175             180             185             190

ATC TGC GGC GGC TAC AAC ACG CCG ACC CAC AAT CCC CTT GTT CCC CAG       624
Ile Cys Gly Gly Tyr Asn Thr Pro Thr His Asn Pro Leu Val Pro Gln
            195             200             205

CAC GAC CAC CTG ACG TCC TTC CAC CAT CTC CTA TCG ATG CAG GCC GGG       672
His Asp His Leu Thr Ser Phe His His Leu Leu Ser Met Gln Ala Gly
            210             215             220

TCT TAT CAG AAC GGG GCC TGG TCC GCG GCC GCG GGC AAG GCG GGC ATG       720
Ser Tyr Gln Asn Gly Ala Trp Ser Ala Ala Ala Gly Lys Ala Gly Met
            225             230             235

GAG GAG AAC TGC ATG CTG CTC GGC CAC TCC TGC ATC GTG GCG CCG ACC       768
Glu Glu Asn Cys Met Leu Leu Gly His Ser Cys Ile Val Ala Pro Thr
240             245             250

GGG GAA ATC GTC GCT CTC ACT ACG ACG CTG GAA GAC GAG GTG ATC ACC       816
Gly Glu Ile Val Ala Leu Thr Thr Thr Leu Glu Asp Glu Val Ile Thr
255             260             265             270

GCC GCC GTC GAT CTC GAT CGC TGC CGG GAA CTG CGT GAA CAC ATC TTC       864
Ala Ala Val Asp Leu Asp Arg Cys Arg Glu Leu Arg Glu His Ile Phe
            275             280             285

AAC TTC AAG CAG CAT CGT CAG CCC CAG CAC TAT GGT CTG ATC GCG GAA       912
Asn Phe Lys Gln His Arg Gln Pro Gln His Tyr Gly Leu Ile Ala Glu
            290             295             300

CTC TGAGGTTGCC GAAAAGCATG TGTGTCGTTG TTCTCGGCGC CTGGGTCACA            965
Leu

TCCAGGCGCG CCAGGGTGAC GCTGGTGGAA TAGTACCACG ACCGCTTCAG GGCGATCCGC    1025

AAGGAGATGC GGGTCGCCGG AGCGGCAAAG CCCGACATTC GTTTCGCACC GACGGCCGTC    1085
```

```
GTGAACTCGA CAGTCCGCGA GAAGGGCGTA TTGCGCGGCC TGGACCTGTA CGTGGAACTG    1145

TAGCCCATAT ATAGATTTCC AAAGAGTTTC GGCGAGGCGC GGCGCGCCTA GCCCCATGTG    1205

AGCGAGAACC GTGCCCAGAT CAAAGAATGA GACCGACGCG CCGGCCGCGG CAAAGGATGA    1265

TCCTCAGGGT CGGATCTATC GCTCCGCCCT GAAGCAGGAG GGCGCACGCT GGCTGCTGAC    1325

GGCGGAGGAA GGGTTGCTGG CAAAGCCCAA GCCGCCCGGC CTTGTTCCGG CACTTGAGAA    1385

TGCGATCGCC ATCGTCGATT ACATCAACGG TACACCGCCC CATATCGCGT CCCTGGCGGA    1445

GCTTTCAACG ACGCTCGGGA TATCCAAGAG CCACTGTCAC TCCATCCTCA AGACGCTGAC    1505

GCATTTCGGC TGGCTGAAAT TCGACAATCG CTCAAAGAGC TACGAGCTGA ATTC          1559
```

(2) INFORMATION FOR SEQ ID NO:40:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:40:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
        35                  40                  45

Leu Thr Thr Phe Phe Pro Arg Trp His Phe Thr Asp Glu Ala Glu Leu
    50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Leu Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270
```

-continued

```
Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
        290                 295                 300
```

(2) INFORMATION FOR SEQ ID NO:41:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD425

(ix) FEATURE:
        (A) NAME/KEY: CDS
        (B) LOCATION: join(7..915)

(xi) SEQUENCE DESCRIPTION: SEQ ID NO:41:

```
CATATG ACA CGT CAG ATG ATA CTT GCA GTG GGA CAA CAA GGT CCG ATC        48
       Thr Arg Gln Met Ile Leu Ala Val Gly Gln Gln Gly Pro Ile
        1               5                  10

GCG CGC GCG GAG ACA CGC GAA CAG GTC GTC GTT CGT CTT CTC GAC ATG        96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA       144
Leu Thr Lys Ala Ala Ser Arg Gly Ala Asn Phe Ile Val Phe Pro Glu
             35                  40                  45

CTC GCG CTT ACG ACC TTC TTC CCG CGC TGG CAT TTC ACC GAC GAG GCC       192
Leu Ala Leu Thr Thr Phe Phe Pro Arg Trp His Phe Thr Asp Glu Ala
         50                  55                  60

GAG CTC GAT AGC TTC TAT GAG ACC GAA ATG CCC GGC CCG GTG GTC CGT       240
Glu Leu Asp Ser Phe Tyr Glu Thr Glu Met Pro Gly Pro Val Val Arg
     65                  70                  75

CCA CTC TTT GAG AAG GCC GCG GAA CTC GGG ATC GGC TTC AAT CTG GGC       288
Pro Leu Phe Glu Lys Ala Ala Glu Leu Gly Ile Gly Phe Asn Leu Gly
 80                  85                  90

TAC GCT GAA CTC GTC GTC GAA GGC GGC GTC AAG CGT CGC TTC AAC ACG       336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG       384
Ser Ile Leu Val Asp Lys Ser Gly Lys Ile Val Gly Lys Tyr Arg Lys
             115                 120                 125

ATC CAT TTG CCG GGT CAC AAG GAG TAC GAG GCC TAC CGG CCG TTC CAG       432
Ile His Leu Pro Gly His Lys Glu Tyr Glu Ala Tyr Arg Pro Phe Gln
         130                 135                 140

CAT CTT GAA AAG CGT TAT TTC GAG CCG GGC GAT CTC GGC TTC CCG GTC       480
His Leu Glu Lys Arg Tyr Phe Glu Pro Gly Asp Leu Gly Phe Pro Val
     145                 150                 155

TAT GAC GTC GAC GCC GCG AAA ATG GGG ATG TTC ATC TGC AAC GAT CGC       528
Tyr Asp Val Asp Ala Ala Lys Met Gly Met Phe Ile Cys Asn Asp Arg
 160                 165                 170

CGC TGG CCT GAA GCC TGG CGG GTG ATG GGC CTC AGG GGC GCC GAG ATC       576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC TCT GTT CCC CAG       624
Ile Cys Gly Gly Tyr Asn Thr Pro Thr His Asn Pro Ser Val Pro Gln
             195                 200                 205
```

```
CAC GAC CAC CTG ACG TCC TTC CAC CAT CTC CTA TCG ATG CAG GCC GGG      672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG      720
Ser Tyr Gln Asn Gly Ala Trp Ser Ala Ala Ala Gly Lys Ala Gly Met
                225                 230                 235

GAG GAG AAC TGC ATG CTG CTC GGC CAC TCC TGC ATC GTG GCG CCG ACC      768
Glu Glu Asn Cys Met Leu Leu Gly His Ser Cys Ile Val Ala Pro Thr
        240                 245                 250

GGG GAA ATC GTC GCT CTC ACT ACG ACG CTG GAA GAC GAG GTG ATC ACC      816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC      864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA      912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA           965
Leu

TCCAGGCGCG CCAGGGTGAC GCTGGTGGAA TAGTACCACG ACCGCTTCAG GGCGATCCGC   1025

AAGGAGATGC GGGTCGCCGG AGCGGCAAAG CCCGACATTG GTTTCGCACC GACGGCCGTC   1085

GTGAACTCGA CAGTCCGCGA GAAGGGCGTA TTGCGCGGCC TGGACCTGTA CGTGGAACTG   1145

TAGCCCATAT ATAGATTTCC AAAGAGTTTC GGCGAGGCGC GGCGCGCCTA GCCCCATGTG   1205

AGCGAGAACC GTGCCCAGAT CAAAGAATGA GACCGACGCG CCGGCCGCGG CAAAGGATGA   1265

TCCTCAGGGT CGGATCTATC GCTCCGCCCT GAAGCAGGAG GGCGCACGCT GGCTGCTGAC   1325

GGCGGAGGAA GGGTTGCTGG CAAAGCCCAA GCCGCCCGGC CTTGTTCCGG CACTTGAGAA   1385

TGCGATCGCC ATCGTCGATT ACATCAACGG TACACCGCCC CATATCGCGT CCCTGGCGGA   1445

GCTTTCAACG ACGCTCGGGA TATCCAAGAG CCACTGTCAC TCCATCCTCA AGACGCTGAC   1505

GCATTTCGGC TGGCTGAAAT TCGACAATCG CTCAAAGAGC TACGAGCTGA ATTC         1559

(2) INFORMATION FOR SEQ ID NO:42:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:42:

Thr Arg Gln Met Ile Leu Ala Val Gly Gln Gln Gly Pro Ile Ala Arg
1               5                   10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
            35                  40                  45

Leu Thr Thr Phe Phe Pro Arg Trp His Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110
```

-continued

```
Leu Val Asp Lys Ser Gly Lys Ile Val Gly Lys Tyr Arg Lys Ile His
            115                 120                 125
Leu Pro Gly His Lys Glu Tyr Glu Ala Tyr Arg Pro Phe Gln His Leu
        130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                165                 170                 175
Pro Glu Ala Trp Arg Val Met Gly Leu Arg Gly Ala Glu Ile Ile Cys
            180                 185                 190
Gly Gly Tyr Asn Thr Pro Thr His Asn Pro Ser Val Pro Gln His Asp
        195                 200                 205
His Leu Thr Ser Phe His His Leu Leu Ser Met Gln Ala Gly Ser Tyr
        210                 215                 220
Gln Asn Gly Ala Trp Ser Ala Ala Gly Lys Ala Gly Met Glu Glu
225                 230                 235                 240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
        275                 280                 285
Lys Gln His Arg Gln Pro Gln His Tyr Gly Leu Ile Ala Glu Leu
        290                 295                 300
```

(2) INFORMATION FOR SEQ ID NO:43:

(i) SEQUENCE CHARACTERISTICS:
      (A) LENGTH: 1559 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Escherichia coli
      (B) STRAIN: JM109 pAD426

(ix) FEATURE:
      (A) NAME/KEY: CDS
      (B) LOCATION: join(7..915)

(xi) SEQUENCE DESCRIPTION: SEQ ID NO:43:

```
CATATG ACA CGT CAG ATG ATA CTT GCA GTG GGA CAA CAA GGT CCG ATC       48
       Thr Arg Gln Met Ile Leu Ala Val Gly Gln Gln Gly Pro Ile
        1               5                  10

GCG CGC GCG GAG ACA CGC GAA CAG GTC GTC GTT CGT CTT CTC GAC ATG       96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA      144
Leu Thr Lys Ala Ala Ser Arg Gly Ala Asn Phe Ile Val Phe Pro Glu
              35                  40                  45

CTC GCG CTT ACG ACC TTC TTC CCG CGC TGG TAT TTC ACC GAC GAG GCC      192
Leu Ala Leu Thr Thr Phe Phe Pro Arg Trp Tyr Phe Thr Asp Glu Ala
          50                  55                  60

GAG CTC GAT AGC TTC TAT GAG ACC GAA ATG CCC GGC CCG GTG GTC CGT      240
Glu Leu Asp Ser Phe Tyr Glu Thr Glu Met Pro Gly Pro Val Val Arg
      65                  70                  75

CCA CTC TTT GAG AAG GCC GCG GAA CTC GGG ATC GGC TTC AAT CTG GGC      288
```

```
Pro Leu Phe Glu Lys Ala Ala Glu Leu Gly Ile Gly Phe Asn Leu Gly
    80              85                  90

TAC GCT GAA CTC GTC GTC GAA GGC GGC GTC AAG CGT CGC TTC AAC ACG         336
Tyr Ala Glu Leu Val Val Glu Gly Gly Val Lys Arg Arg Phe Asn Thr
 95             100                 105                     110

TCC ATT TTG GTG GAT AAG TCA GGC AAG ATC GTC GGC AAG TAT CGT AAG         384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG         432
Ile His Leu Pro Gly His Lys Glu Tyr Glu Ala Tyr Arg Pro Phe Gln
            130                 135                 140

CAT CTT GAA AAG CGT TAT TTC GAG CCG GGC GAT CTC GGC TTC CCG GTC         480
His Leu Glu Lys Arg Tyr Phe Glu Pro Gly Asp Leu Gly Phe Pro Val
        145                 150                 155

TAT GAC GTC GAC GCC GCG AAA ATG GGG ATG TTC ATC TGC AAC GAT CGC         528
Tyr Asp Val Asp Ala Ala Lys Met Gly Met Phe Ile Cys Asn Asp Arg
    160                 165                 170

CGC TGG CCT GAA GCC TGG CGG GTG ATG GGC CTC AGG GGC GCC GAG ATC         576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC CTT GTT CCC CAG         624
Ile Cys Gly Gly Tyr Asn Thr Pro Thr His Asn Pro Leu Val Pro Gln
                195                 200                 205

CAC GAC CAC CTG ACG TCC TTC CAC CAT CTC CTA TCG ATG CAG GCC GGG         672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG         720
Ser Tyr Gln Asn Gly Ala Trp Ser Ala Ala Ala Gly Lys Ala Gly Met
        225                 230                 235

GAG GAG AAC TGC ATG CTG CTC GGC CAC TCC TGC ATC GTG GCG CCG ACC         768
Glu Glu Asn Cys Met Leu Leu Gly His Ser Cys Ile Val Ala Pro Thr
    240                 245                 250

GGG GAA ATC GTC GCT CTC ACT ACG ACG CTG GAA GAC GAG GTG ATC ACC         816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC         864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA         912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA              965
Leu

TCCAGGCGCG CCAGGGTGAC GCTGGTGGAA TAGTACCACG ACCGCTTCAG GGCGATCCGC      1025

AAGGAGATGC GGGTCGCCGG AGCGGCAAAG CCCGACATTC GTTTCGCACC GACGGCCGTC      1085

GTGAACTCGA CAGTCCGCGA GAAGGGCGTA TTGCGCGGCC TGGACCTGTA CGTGGAACTG      1145

TAGCCCATAT ATAGATTTCC AAAGAGTTTC GGCGAGGCGC GGCGCGCCTA GCCCCATGTG      1205

AGCGAGAACC GTGCCCAGAT CAAAGAATGA GACCGACGCG CCGGCCGCGG CAAAGGATGA      1265

TCCTCAGGGT CGGATCTATC GCTCCGCCCT GAAGCAGGAG GGCGCACGCT GGCTGCTGAC      1325

GGCGGAGGAA GGGTTGCTGG CAAAGCCCAA GCCGCCCGGC CTTGTTCCGG CACTTGAGAA      1385

TGCGATCGCC ATCGTCGATT ACATCAACGG TACACCGCCC CATATCGCGT CCCTGGCGGA      1445

GCTTTCAACG ACGCTCGGGA TATCCAAGAG CCACTGTCAC TCCATCCTCA AGACGCTGAC      1505

GCATTTCGGC TGGCTGAAAT TCGACAATCG CTCAAAGAGC TACGAGCTGA ATTC           1559
```

(2) INFORMATION FOR SEQ ID NO:44:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:44:

```
Thr Arg Gln Met Ile Leu Ala Val Gly Gln Gln Gly Pro Ile Ala Arg
 1               5                  10                  15
Ala Glu Thr Arg Glu Gln Val Val Arg Leu Leu Asp Met Leu Thr
            20                  25                  30
Lys Ala Ala Ser Arg Gly Ala Asn Phe Ile Val Phe Pro Glu Leu Ala
            35                  40                  45
Leu Thr Thr Phe Phe Pro Arg Trp Tyr Phe Thr Asp Glu Ala Glu Leu
     50                  55                  60
Asp Ser Phe Tyr Glu Thr Glu Met Pro Gly Pro Val Val Arg Pro Leu
 65                  70                  75                  80
Phe Glu Lys Ala Ala Glu Leu Gly Ile Gly Phe Asn Leu Gly Tyr Ala
                 85                  90                  95
Glu Leu Val Val Glu Gly Gly Val Lys Arg Arg Phe Asn Thr Ser Ile
            100                 105                 110
Leu Val Asp Lys Ser Gly Lys Ile Val Gly Lys Tyr Arg Lys Ile His
            115                 120                 125
Leu Pro Gly His Lys Glu Tyr Glu Ala Tyr Arg Pro Phe Gln His Leu
130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                165                 170                 175
Pro Glu Ala Trp Arg Val Met Gly Leu Arg Gly Ala Glu Ile Ile Cys
                180                 185                 190
Gly Gly Tyr Asn Thr Pro Thr His Asn Pro Leu Val Pro Gln His Asp
            195                 200                 205
His Leu Thr Ser Phe His His Leu Leu Ser Met Gln Ala Gly Ser Tyr
210                 215                 220
Gln Asn Gly Ala Trp Ser Ala Ala Gly Lys Ala Gly Met Glu Glu
225                 230                 235                 240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
275                 280                 285
Lys Gln His Arg Gln Pro Gln His Tyr Gly Leu Ile Ala Glu Leu
290                 295                 300
```

(2) INFORMATION FOR SEQ ID NO:45:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (A) ORGANISM: Escherichia coli
    (B) STRAIN: JM109 pAD427

(ix) FEATURE:
    (A) NAME/KEY: CDS
    (B) LOCATION: join(7..915)

(xi) SEQUENCE DESCRIPTION: SEQ ID NO:45:

| | | | | | | | | | | | | | | |
|---|---|---|---|---|---|---|---|---|---|---|---|---|---|---|
| CATATG | ACA | CGT | CAG | ATG | ATA | CTT | GCA | GTG | GGA | CAA | CAA | GGT | CCG | ATC | 48 |
| | Thr | Arg | Gln | Met | Ile | Leu | Ala | Val | Gly | Gln | Gln | Gly | Pro | Ile |
| | 1 | | | 5 | | | | | 10 | | | | | |

| GCG | CGC | GCG | GAG | ACA | CGC | GAA | CAG | GTC | GTC | GTT | CGT | CTT | CTC | GAC | ATG | 96 |
|---|---|---|---|---|---|---|---|---|---|---|---|---|---|---|---|---|
| Ala | Arg | Ala | Glu | Thr | Arg | Glu | Gln | Val | Val | Val | Arg | Leu | Leu | Asp | Met |
| 15 | | | | 20 | | | | | 25 | | | | | | 30 |

| CTG | ACG | AAA | GCC | GCG | AGC | CGG | GGC | GCG | AAT | TTC | ATT | GTC | TTC | CCC | GAA | 144 |
|---|---|---|---|---|---|---|---|---|---|---|---|---|---|---|---|---|
| Leu | Thr | Lys | Ala | Ala | Ser | Arg | Gly | Ala | Asn | Phe | Ile | Val | Phe | Pro | Glu |
| | | | | 35 | | | | | 40 | | | | | 45 | |

| CTC | GCG | CTT | ACG | ACC | TTC | TTC | CCG | CGC | TGG | TAT | TTC | ACC | GAC | GAG | GCC | 192 |
|---|---|---|---|---|---|---|---|---|---|---|---|---|---|---|---|---|
| Leu | Ala | Leu | Thr | Thr | Phe | Phe | Pro | Arg | Trp | Tyr | Phe | Thr | Asp | Glu | Ala |
| | | | 50 | | | | | 55 | | | | | 60 | | |

| GAG | CTC | GAT | AGC | TTC | TAT | GAG | ACC | GAA | ATG | CCC | GGC | CCG | GTG | GTC | CGT | 240 |
|---|---|---|---|---|---|---|---|---|---|---|---|---|---|---|---|---|
| Glu | Leu | Asp | Ser | Phe | Tyr | Glu | Thr | Glu | Met | Pro | Gly | Pro | Val | Val | Arg |
| | | 65 | | | | | 70 | | | | | 75 | | | |

| CCA | CTC | TTT | GAG | AAG | GCC | GCG | GAA | CTC | GGG | ATC | GGC | TTC | AAT | CTG | GGC | 288 |
|---|---|---|---|---|---|---|---|---|---|---|---|---|---|---|---|---|
| Pro | Leu | Phe | Glu | Lys | Ala | Ala | Glu | Leu | Gly | Ile | Gly | Phe | Asn | Leu | Gly |
| 80 | | | | | 85 | | | | | 90 | | | | | |

| TAC | GCT | GAA | CTC | GTC | GTC | GAA | GGC | GGC | GTC | AAG | CGT | CGC | TTC | AAC | ACG | 336 |
|---|---|---|---|---|---|---|---|---|---|---|---|---|---|---|---|---|
| Tyr | Ala | Glu | Leu | Val | Val | Glu | Gly | Gly | Val | Lys | Arg | Arg | Phe | Asn | Thr |
| 95 | | | | | 100 | | | | | 105 | | | | | 110 |

| TCC | ATT | TTG | GTG | GAT | AAG | TCA | GGC | AAG | ATC | GTC | GGC | AAG | TAT | CGT | AAG | 384 |
|---|---|---|---|---|---|---|---|---|---|---|---|---|---|---|---|---|
| Ser | Ile | Leu | Val | Asp | Lys | Ser | Gly | Lys | Ile | Val | Gly | Lys | Tyr | Arg | Lys |
| | | | | 115 | | | | | 120 | | | | | 125 | |

| ATC | CAT | TTG | CCG | GGT | CAC | AAG | GAG | TAC | GAG | GCC | TAC | CGG | CCG | TTC | CAG | 432 |
|---|---|---|---|---|---|---|---|---|---|---|---|---|---|---|---|---|
| Ile | His | Leu | Pro | Gly | His | Lys | Glu | Tyr | Glu | Ala | Tyr | Arg | Pro | Phe | Gln |
| | | | 130 | | | | | 135 | | | | | 140 | | |

| CAT | CTT | GAA | AAG | CGT | TAT | TTC | GAG | CCG | GGC | GAT | CTC | GGC | TTC | CCG | GTC | 480 |
|---|---|---|---|---|---|---|---|---|---|---|---|---|---|---|---|---|
| His | Leu | Glu | Lys | Arg | Tyr | Phe | Glu | Pro | Gly | Asp | Leu | Gly | Phe | Pro | Val |
| | | 145 | | | | | 150 | | | | | 155 | | | |

| TAT | GAC | GTC | GAC | GCC | GCG | AAA | ATG | GGG | ATG | TTC | ATC | TGC | AAC | GAT | CGC | 528 |
|---|---|---|---|---|---|---|---|---|---|---|---|---|---|---|---|---|
| Tyr | Asp | Val | Asp | Ala | Ala | Lys | Met | Gly | Met | Phe | Ile | Cys | Asn | Asp | Arg |
| 160 | | | | | 165 | | | | | 170 | | | | | |

| CGC | TGG | CCT | GAA | GCC | TGG | CGG | GTG | ATG | GGC | CTC | AGG | GGC | GCC | GAG | ATC | 576 |
|---|---|---|---|---|---|---|---|---|---|---|---|---|---|---|---|---|
| Arg | Trp | Pro | Glu | Ala | Trp | Arg | Val | Met | Gly | Leu | Arg | Gly | Ala | Glu | Ile |
| 175 | | | | | 180 | | | | | 185 | | | | | 190 |

| ATC | TGC | GGC | GGC | TAC | AAC | ACG | CCG | ACC | CAC | AAT | CCC | TCT | GTT | CCC | CAG | 624 |
|---|---|---|---|---|---|---|---|---|---|---|---|---|---|---|---|---|
| Ile | Cys | Gly | Gly | Tyr | Asn | Thr | Pro | Thr | His | Asn | Pro | Ser | Val | Pro | Gln |
| | | | | 195 | | | | | 200 | | | | | 205 | |

| CAC | GAC | CAC | CTG | ACG | TCC | TTC | CAC | CAT | CTC | CTA | TCG | ATG | CAG | GCC | GGG | 672 |
|---|---|---|---|---|---|---|---|---|---|---|---|---|---|---|---|---|
| His | Asp | His | Leu | Thr | Ser | Phe | His | His | Leu | Leu | Ser | Met | Gln | Ala | Gly |
| | | | 210 | | | | | 215 | | | | | 220 | | |

| TCT | TAT | CAG | AAC | GGG | GCC | TGG | TCC | GCG | GCC | GCG | GGC | AAG | GCG | GGC | ATG | 720 |
|---|---|---|---|---|---|---|---|---|---|---|---|---|---|---|---|---|
| Ser | Tyr | Gln | Asn | Gly | Ala | Trp | Ser | Ala | Ala | Ala | Gly | Lys | Ala | Gly | Met |
| | | 225 | | | | | 230 | | | | | 235 | | | |

| GAG | GAG | AAC | TGC | ATG | CTG | CTC | GGC | CAC | TCC | TGC | ATC | GTG | GCG | CCG | ACC | 768 |
|---|---|---|---|---|---|---|---|---|---|---|---|---|---|---|---|---|
| Glu | Glu | Asn | Cys | Met | Leu | Leu | Gly | His | Ser | Cys | Ile | Val | Ala | Pro | Thr |
| | | 240 | | | | | 245 | | | | | 250 | | | |

| GGG | GAA | ATC | GTC | GCT | CTC | ACT | ACG | ACG | CTG | GAA | GAC | GAG | GTG | ATC | ACC | 816 |
|---|---|---|---|---|---|---|---|---|---|---|---|---|---|---|---|---|
| Gly | Glu | Ile | Val | Ala | Leu | Thr | Thr | Thr | Leu | Glu | Asp | Glu | Val | Ile | Thr |
| 255 | | | | | 260 | | | | | 265 | | | | | 270 |

| GCC | GCC | GTC | GAT | CTC | GAT | CGC | TGC | CGG | GAA | CTG | CGT | GAA | CAC | ATC | TTC | 864 |
|---|---|---|---|---|---|---|---|---|---|---|---|---|---|---|---|---|

```
Ala Ala Val Asp Leu Asp Arg Cys Arg Glu Leu Arg Glu His Ile Phe
            275                 280                 285

AAC TTC AAG CAG CAT CGT CAG CCC CAG CAC TAT GGT CTG ATC GCG GAA        912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA             965
Leu

TCCAGGCGCG CCAGGGTGAC GCTGGTGGAA TAGTACCACG ACCGCTTCAG GGCGATCCGC      1025

AAGGAGATGC GGGTCGCCGG AGCGGCAAAG CCCGACATTC GTTTCGCACC GACGGCCGTC      1085

GTGAACTCGA CAGTCCGCGA GAAGGGCGTA TTGCGCGGCC TGGACCTGTA CGTGGAACTG      1145

TAGCCCATAT ATAGATTTCC AAAGAGTTTC GGCGAGGCGC GGCGCGCCTA GCCCCATGTG      1205

AGCGAGAACC GTGCCCAGAT CAAAGAATGA GACCGACGCG CCGGCCGCGG CAAAGGATGA      1265

TCCTCAGGGT CGGATCTATC GCTCCGCCCT GAAGCAGGAG GGCGCACGCT GGCTGCTGAC      1325

GGCGGAGGAA GGGTTGCTGG CAAAGCCCAA GCCGCCCGGC CTTGTTCCGG CACTTGAGAA      1385

TGCGATCGCC ATCGTCGATT ACATCAACGG TACACCGCCC CATATCGCGT CCCTGGCGGA      1445

GCTTTCAACG ACGTCGGGA TATCCAAGAG CCACTGTCAC TCCATCCTCA AGACGCTGAC       1505

GCATTTCGGC TGGCTGAAAT CGACAATCG CTCAAAGAGC TACGAGCTGA ATTC             1559
```

(2) INFORMATION FOR SEQ ID NO:46:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:46:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp Tyr Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                85                  90                  95

Glu Leu Val Val Glu Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
     130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Ser Val Pro Gln His Asp
```

```
                195                  200                      205
His Leu Thr Ser Phe His His Leu Leu Ser Met Gln Ala Gly Ser Tyr
        210                  215                  220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
    290                 295                 300
```

(2) INFORMATION FOR SEQ ID NO:47:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD451

(ix) FEATURE:
        (A) NAME/KEY: CDS
        (B) LOCATION: join(233..1141)

(xi) SEQUENCE DESCRIPTION: SEQ ID NO:47:

```
GTCGACGGCG GGCTCGCGCG AGAGCTTGTC AAGCAGCGCA AATTCCGGTT CCGCTCCGGT    60

TGACAGATCA AAAATTTTAC GCCTGTTATT GTCGTGCTGC ATGTAATATT TCGTACTTTA   120

TGTAGAATTT GCATTGCGCC GCGAGTCACA AAGCCGGTTT TCGGCGATGT GTTTCACAAC   180

GTTTTCCCGG CCGCTGGGCC GGACATCACC TAGGAAGGAG CAGAGGTTCA TG ACA       235
                                                        Thr
                                                         1

CGT CAG ATG ATA CTT GCA GTG GGA CAA CAA GGT CCG ATC GCG CGC GCG    283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA    331
Glu Thr Arg Glu Gln Val Val Val Arg Leu Leu Asp Met Leu Thr Lys
        20                  25                  30

GCC GCG AGC CGG GGC GCG AAT TTC ATT GTC TTC CCC GAA CTC GCG CTT    379
Ala Ala Ser Arg Gly Ala Asn Phe Ile Val Phe Pro Glu Leu Ala Leu
    35                  40                  45

ACG ACC TTC TTC CCG CGC TGG TAT TTC ACC GAC GAG GCC GAG CTC GAT    427
Thr Thr Phe Phe Pro Arg Trp Tyr Phe Thr Asp Glu Ala Glu Leu Asp
 50                 55                  60                  65

AGC TTC TAT GAG ACC GAA ATG CCC GGC CCG GTG GTC CGT CCA CTC TTT    475
Ser Phe Tyr Glu Thr Glu Met Pro Gly Pro Val Val Arg Pro Leu Phe
                70                  75                  80

GAG AAG GCC GCG GAA CTC GGG ATC GGC TTC AAT CTG GGC TAC GCT GAA    523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG    571
Leu Val Val Glu Gly Gly Val Lys Arg Arg Phe Asn Thr Ser Ile Leu
        100                 105                 110
```

```
GTG GAT AAG TCA GGC AAG ATC GTC GGC AAG TAT CGT AAG ATC CAT TTG          619
Val Asp Lys Ser Gly Lys Ile Val Gly Lys Tyr Arg Lys Ile His Leu
        115                 120                 125

CCG GGT CAC AAG GAG TAC GAG GCC TAC CGG CCG TTC CAG CAT CTT GAA          667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC          715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT          763
Asp Ala Ala Lys Met Gly Met Phe Ile Cys Asn Asp Arg Arg Trp Pro
                165                 170                 175

GAA GCC TGG CGG GTG ATG GGC CTC AGG GGC GCC GAG ATC ATC TGC GGC          811
Glu Ala Trp Arg Val Met Gly Leu Arg Gly Ala Glu Ile Ile Cys Gly
        180                 185                 190

GGC TAC AAC ACG CCG ACC CAC AAT CCC GAA GTT CCC CAG CAC GAC CAC          859
Gly Tyr Asn Thr Pro Thr His Asn Pro Glu Val Pro Gln His Asp His
        195                 200                 205

CTG ACG TCC TTC CAC CAT CTC CTA TCG ATG CAG GCC GGG TCT TAT CAG          907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC          955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC         1003
Cys Met Leu Leu Gly His Ser Cys Ile Val Ala Pro Thr Gly Glu Ile
                245                 250                 255

GTC GCT CTC ACT ACG ACG CTG GAA GAC GAG GTG ATC ACC GCC GCC GTC         1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG         1099
Asp Leu Asp Arg Cys Arg Glu Leu Arg Glu His Ile Phe Asn Phe Lys
275                 280                 285

CAG CAT CGT CAG CCC CAG CAC TAT GGT CTG ATC GCG GAA CTC                 1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG        1201

CCAGGGTGAC GCTGGTGGAA TAGTACCACG ACCGCTTCAG GGCGATCCGC AAGGAGATGC        1261

GGGTCGCCGG AGCGGCAAAG CCCGACATTC GTTTCGCACC GACGGCCGTC GTGAACTCGA        1321

CAGTCCGCGA AAGGGCGTA TTGCGCGGCC TGGACCTGTA CGTGGAACTG TAGCCCATAT        1381

ATAGATTTCC AAAGAGTTTC GGCGAGGCGC GGCGCGCCTA GCCCCATGTG AGCGAGAACC        1441

GTGCCCAGAT CAAAGAATGA GACCGACGCG CCGGCCGCGG CAAAGGATGA TCCTCAGGGT        1501

CGGATCTATC GCTCCGCCCT GAAGCAGGAG GGCGCACGCT GGCTGCTGAC GGCGGAGGAA        1561

GGGTTGCTGG CAAAGCCCAA GCCGCCCGGC CTTGTTCCGG CACTTGAGAA TGCGATCGCC        1621

ATCGTCGATT ACATCAACGG TACACCGCCC CATATCGCGT CCCTGGCGGA GCTTTCAACG        1681

ACGCTCGGGA TATCCAAGAG CCACTGTCAC TCCATCCTCA AGACGCTGAC GCATTTCGGC        1741

TGGCTGAAAT TCGACAATCG CTCAAAGAGC TACGAGCTGA ATTC                        1785
```

(2) INFORMATION FOR SEQ ID NO:48:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:48:

Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
             35                  40                  45

Leu Thr Thr Phe Phe Pro Arg Trp Tyr Phe Thr Asp Glu Ala Glu Leu
         50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
             115                 120                 125

Leu Pro Gly His Lys Glu Tyr Glu Ala Tyr Arg Pro Phe Gln His Leu
 130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Glu Val Pro Gln His Asp
         195                 200                 205

His Leu Thr Ser Phe His His Leu Leu Ser Met Gln Ala Gly Ser Tyr
 210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
290                 295                 300

(2) INFORMATION FOR SEQ ID NO:49:

(i) SEQUENCE CHARACTERISTICS:
       (A) LENGTH: 1785 base pairs
       (B) TYPE: nucleic acid
       (C) STRANDEDNESS: double
       (D) TOPOLOGY: linear (ii) MOLECULE TYPE: DNA (genomic)

(vi) ORIGINAL SOURCE:
       (A) ORGANISM: Escherichia coli
       (B) STRAIN: JM109 pAD452

(ix) FEATURE:
       (A) NAME/KEY: CDS
       (B) LOCATION: join(233..1141)

(xi) SEQUENCE DESCRIPTION: SEQ ID NO:49:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                        Thr
                                                         1
```

| | | | | | | | | | | | | | | | | |
|---|---|---|---|---|---|---|---|---|---|---|---|---|---|---|---|---|
| CGT | CAG | ATG | ATA | CTT | GCA | GTG | GGA | CAA | CAA | GGT | CCG | ATC | GCG | CGC | GCG | 283 |
| Arg | Gln | Met | Ile | Leu | Ala | Val | Gly | Gln | Gln | Gly | Pro | Ile | Ala | Arg | Ala | |
| | | | 5 | | | | | 10 | | | | | 15 | | | |
| GAG | ACA | CGC | GAA | CAG | GTC | GTC | GTT | CGT | CTT | CTC | GAC | ATG | CTG | ACG | AAA | 331 |
| Glu | Thr | Arg | Glu | Gln | Val | Val | Val | Arg | Leu | Leu | Asp | Met | Leu | Thr | Lys | |
| | | 20 | | | | | 25 | | | | | 30 | | | | |
| GCC | GCG | AGC | CGG | GGC | GCG | AAT | TTC | ATT | GTC | TTC | CCC | GAA | CTC | GCG | CTT | 379 |
| Ala | Ala | Ser | Arg | Gly | Ala | Asn | Phe | Ile | Val | Phe | Pro | Glu | Leu | Ala | Leu | |
| | 35 | | | | | 40 | | | | | 45 | | | | | |
| ACG | ACC | TTC | TTC | CCG | CGC | TGG | TAT | TTC | ACC | GAC | GAG | GCC | GAG | CTC | GAT | 427 |
| Thr | Thr | Phe | Phe | Pro | Arg | Trp | Tyr | Phe | Thr | Asp | Glu | Ala | Glu | Leu | Asp | |
| 50 | | | | | 55 | | | | | 60 | | | | | 65 | |
| AGC | TTC | TAT | GAG | ACC | GAA | ATG | CCC | GGC | CCG | GTG | GTC | CGT | CCA | CTC | TTT | 475 |
| Ser | Phe | Tyr | Glu | Thr | Glu | Met | Pro | Gly | Pro | Val | Val | Arg | Pro | Leu | Phe | |
| | | | 70 | | | | | 75 | | | | | 80 | | | |
| GAG | AAG | GCC | GCG | GAA | CTC | GGG | ATC | GGC | TTC | AAT | CTG | GGC | TAC | GCT | GAA | 523 |
| Glu | Lys | Ala | Ala | Glu | Leu | Gly | Ile | Gly | Phe | Asn | Leu | Gly | Tyr | Ala | Glu | |
| | | 85 | | | | | 90 | | | | | 95 | | | | |
| CTC | GTC | GTC | GAA | GGC | GGC | GTC | AAG | CGT | CGC | TTC | AAC | ACG | TCC | ATT | TTG | 571 |
| Leu | Val | Val | Glu | Gly | Gly | Val | Lys | Arg | Arg | Phe | Asn | Thr | Ser | Ile | Leu | |
| | | 100 | | | | | 105 | | | | | 110 | | | | |
| GTG | GAT | AAG | TCA | GGC | AAG | ATC | GTC | GGC | AAG | TAT | CGT | AAG | ATC | CAT | TTG | 619 |
| Val | Asp | Lys | Ser | Gly | Lys | Ile | Val | Gly | Lys | Tyr | Arg | Lys | Ile | His | Leu | |
| | 115 | | | | | 120 | | | | | 125 | | | | | |
| CCG | GGT | CAC | AAG | GAG | TAC | GAG | GCC | TAC | CGG | CCG | TTC | CAG | CAT | CTT | GAA | 667 |
| Pro | Gly | His | Lys | Glu | Tyr | Glu | Ala | Tyr | Arg | Pro | Phe | Gln | His | Leu | Glu | |
| 130 | | | | | 135 | | | | | 140 | | | | | 145 | |
| AAG | CGT | TAT | TTC | GAG | CCG | GGC | GAT | CTC | GGC | TTC | CCG | GTC | TAT | GAC | GTC | 715 |
| Lys | Arg | Tyr | Phe | Glu | Pro | Gly | Asp | Leu | Gly | Phe | Pro | Val | Tyr | Asp | Val | |
| | | | 150 | | | | | 155 | | | | | 160 | | | |
| GAC | GCC | GCG | AAA | ATG | GGG | ATG | TTC | ATC | TGC | AAC | GAT | CGC | CGC | TGG | CCT | 763 |
| Asp | Ala | Ala | Lys | Met | Gly | Met | Phe | Ile | Cys | Asn | Asp | Arg | Arg | Trp | Pro | |
| | | | 165 | | | | | 170 | | | | | 175 | | | |
| GAA | GCC | TGG | CGG | GTG | ATG | GGC | CTC | AGG | GGC | GCC | GAG | ATC | ATC | TGC | GGC | 811 |
| Glu | Ala | Trp | Arg | Val | Met | Gly | Leu | Arg | Gly | Ala | Glu | Ile | Ile | Cys | Gly | |
| | | 180 | | | | | 185 | | | | | 190 | | | | |
| GGC | TAC | AAC | ACG | CCG | ACC | CAC | AAT | CCC | CCT | GTT | CCC | CAG | CAC | GAC | CAC | 859 |
| Gly | Tyr | Asn | Thr | Pro | Thr | His | Asn | Pro | Pro | Val | Pro | Gln | His | Asp | His | |
| | 195 | | | | | 200 | | | | | 205 | | | | | |
| CTG | ACG | TCC | TTC | CAC | CAT | CTC | CTA | TCG | ATG | CAG | GCC | GGG | TCT | TAT | CAG | 907 |
| Leu | Thr | Ser | Phe | His | His | Leu | Leu | Ser | Met | Gln | Ala | Gly | Ser | Tyr | Gln | |
| 210 | | | | | 215 | | | | | 220 | | | | | 225 | |
| AAC | GGG | GCC | TGG | TCC | GCG | GCC | GCG | GGC | AAG | TCA | GGC | ATG | GAG | GAG | AAC | 955 |
| Asn | Gly | Ala | Trp | Ser | Ala | Ala | Ala | Gly | Lys | Ser | Gly | Met | Glu | Glu | Asn | |
| | | | 230 | | | | | 235 | | | | | 240 | | | |
| TGC | ATG | CTG | CTC | GGC | CAC | TCC | TGC | ATC | GTG | GCG | CCG | ACC | GGG | GAA | ATC | 1003 |
| Cys | Met | Leu | Leu | Gly | His | Ser | Cys | Ile | Val | Ala | Pro | Thr | Gly | Glu | Ile | |
| | | | 245 | | | | | 250 | | | | | 255 | | | |
| GTC | GCT | CTC | ACT | ACG | ACG | CTG | GAA | GAC | GAG | GTG | ATC | ACC | GCC | GCC | GTC | 1051 |
| Val | Ala | Leu | Thr | Thr | Thr | Leu | Glu | Asp | Glu | Val | Ile | Thr | Ala | Ala | Val | |
| | | | 260 | | | | | 265 | | | | | 270 | | | |

-continued

```
GAT CTC GAT CGC TGC CGG GAA CTG CGT GAA CAC ATC TTC AAC TTC AAG    1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC             1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG   1201

CCAGGGTGAC GCTGGTGGAA TAGTACCACG ACCGCTTCAG GGCGATCCGC AAGGAGATGC   1261

GGGTCGCCGG AGCGGCAAAG CCCGACATTC GTTTCGCACC GACGGCCGTC GTGAACTCGA   1321

CAGTCCGCGA GAAGGGCGTA TTGCGCGGCC TGGACCTGTA CGTGGAACTG TAGCCCATAT   1381

ATAGATTTCC AAAGAGTTTC GGCGAGGCGC GGCGCGCCTA GCCCCATGTG AGCGAGAACC   1441

GTGCCCAGAT CAAAGAATGA GACCGACGCG CCGGCCGCGG CAAAGGATGA TCCTCAGGGT   1501

CGGATCTATC GCTCCGCCCT GAAGCAGGAG GGCGCACGCT GGCTGCTGAC GGCGGAGGAA   1561

GGGTTGCTGG CAAAGCCCAA GCCGCCCGGC CTTGTTCCGG CACTTGAGAA TGCGATCGCC   1621

ATCGTCGATT ACATCAACGG TACACCGCCC CATATCGCGT CCCTGGCGGA GCTTTCAACG   1681

ACGCTCGGGA TATCCAAGAG CCACTGTCAC TCCATCCTCA AGACGCTGAC GCATTTCGGC   1741

TGGCTGAAAT TCGACAATCG CTCAAAGAGC TACGAGCTGA ATTC                   1785
```

(2) INFORMATION FOR SEQ ID NO:50:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:50:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
             35                  40                  45

Leu Thr Thr Phe Phe Pro Arg Trp Tyr Phe Thr Asp Glu Ala Glu Leu
 50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Val Lys Arg Arg Phe Asn Thr Ser Ile
                100                 105                 110

Leu Val Asp Lys Ser Gly Lys Ile Val Gly Lys Tyr Arg Lys Ile His
                115                 120                 125

Leu Pro Gly His Lys Glu Tyr Glu Ala Tyr Arg Pro Phe Gln His Leu
            130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Trp
                165                 170                 175

Pro Glu Ala Trp Arg Val Met Gly Leu Arg Gly Ala Glu Ile Ile Cys
            180                 185                 190
```

-continued

```
Gly Gly Tyr Asn Thr Pro Thr His Asn Pro Pro Val Pro Gln His Asp
            195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ser Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
290                 295                 300
```

(2) INFORMATION FOR SEQ ID NO:51:

(i) SEQUENCE CHARACTERISTICS:
      (A) LENGTH: 1785 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Escherichia coli
      (B) STRAIN: JM109 pAD453

(ix) FEATURE:
      (A) NAME/KEY: CDS
      (B) LOCATION: join(233..1141)

(xi) SEQUENCE DESCRIPTION: SEQ ID NO:51:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                        Thr
                                                         1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
        20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
    35                  40                  45

ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
                70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
        100                 105                 110
```

```
GTG GAT AAG TCA GGC AAG ATC GTC GGC AAG TAT CGT AAG ATC CAT TTG            619
Val Asp Lys Ser Gly Lys Ile Val Gly Lys Tyr Arg Lys Ile His Leu
        115                 120                 125

CCG GGT CAC AAG GAG TAC GAG GCC TAC CGG CCG TTC CAG CAT CTT GAA            667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC            715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT            763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC            811
Glu Ala Trp Arg Val Met Gly Leu Arg Gly Ala Glu Ile Ile Cys Gly
        180                 185                 190

GGC TAC AAC ACG CCG ACC CAC AAT CCC GAA GTT CCC CAG CAC GAC CAC            859
Gly Tyr Asn Thr Pro Thr His Asn Pro Glu Val Pro Gln His Asp His
    195                 200                 205

CTG ACG TCC TTC CAC CAT CTC CTA TCG ATG CAG GCC GGG TCT TAT CAG            907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCA GGC ATG GAG GAG AAC            955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC           1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC           1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG           1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC                   1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG         1201

CCAGGGTGAC GCTGGTGGAA TAGTACCACG ACCGCTTCAG GGCGATCCGC AAGGAGATGC         1261

GGGTCGCCGG AGCGGCAAAG CCCGACATTC GTTTCGCACC GACGGCCGTC GTGAACTCGA         1321

CAGTCCGCGA GAAGGGCGTA TTGCGCGGCC TGGACCTGTA CGTGGAACTG TAGCCCATAT         1381

ATAGATTTCC AAAGAGTTTC GGCGAGGCGC GGCGCGCCTA GCCCCATGTG AGCGAGAACC         1441

GTGCCCAGAT CAAAGAATGA GACCGACGCG CCGGCCGCGG CAAAGGATGA TCCTCAGGGT         1501

CGGATCTATC GCTCCGCCCT GAAGCAGGAG GGCGCACGCT GGCTGCTGAC GGCGGAGGAA         1561

GGGTTGCTGG CAAAGCCCAA GCCGCCCGGC CTTGTTCCGG CACTTGAGAA TGCGATCGCC         1621

ATCGTCGATT ACATCAACGG TACACCGCCC CATATCGCGT CCCTGGCGGA GCTTTCAACG         1681

ACGCTCGGGA TATCCAAGAG CCACTGTCAC TCCATCCTCA AGACGCTGAC GCATTTCGGC         1741

TGGCTGAAAT TCGACAATCG CTCAAAGAGC TACGAGCTGA ATTC                         1785
```

(2) INFORMATION FOR SEQ ID NO:52:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:52:

| Thr | Arg | Gln | Met | Ile | Leu | Ala | Val | Gly | Gln | Gln | Gly | Pro | Ile | Ala | Arg |
|---|---|---|---|---|---|---|---|---|---|---|---|---|---|---|---|
| 1 | | | | 5 | | | | | 10 | | | | | 15 | |

| Ala | Glu | Thr | Arg | Glu | Gln | Val | Val | Arg | Leu | Leu | Asp | Met | Leu | Thr |
|---|---|---|---|---|---|---|---|---|---|---|---|---|---|---|
| | | 20 | | | | | 25 | | | | | 30 | | |

| Lys | Ala | Ala | Ser | Arg | Gly | Ala | Asn | Phe | Ile | Val | Phe | Pro | Glu | Leu | Ala |
|---|---|---|---|---|---|---|---|---|---|---|---|---|---|---|---|
| | | 35 | | | | | 40 | | | | | 45 | | | |

| Leu | Thr | Thr | Phe | Phe | Pro | Arg | Trp | His | Phe | Thr | Asp | Glu | Ala | Glu | Leu |
|---|---|---|---|---|---|---|---|---|---|---|---|---|---|---|---|
| | 50 | | | | | 55 | | | | | 60 | | | | |

| Asp | Ser | Phe | Tyr | Glu | Thr | Glu | Met | Pro | Gly | Pro | Val | Val | Arg | Pro | Leu |
|---|---|---|---|---|---|---|---|---|---|---|---|---|---|---|---|
| 65 | | | | | 70 | | | | | 75 | | | | | 80 |

| Phe | Glu | Lys | Ala | Ala | Glu | Leu | Gly | Ile | Gly | Phe | Asn | Leu | Gly | Tyr | Ala |
|---|---|---|---|---|---|---|---|---|---|---|---|---|---|---|---|
| | | | | 85 | | | | | 90 | | | | | 95 | |

| Glu | Leu | Val | Val | Glu | Gly | Gly | Val | Lys | Arg | Arg | Phe | Asn | Thr | Ser | Ile |
|---|---|---|---|---|---|---|---|---|---|---|---|---|---|---|---|
| | | | 100 | | | | | 105 | | | | | 110 | | |

| Leu | Val | Asp | Lys | Ser | Gly | Lys | Ile | Val | Gly | Lys | Tyr | Arg | Lys | Ile | His |
|---|---|---|---|---|---|---|---|---|---|---|---|---|---|---|---|
| | | | 115 | | | | | 120 | | | | | 125 | | |

| Leu | Pro | Gly | His | Lys | Glu | Tyr | Glu | Ala | Tyr | Arg | Pro | Phe | Gln | His | Leu |
|---|---|---|---|---|---|---|---|---|---|---|---|---|---|---|---|
| | 130 | | | | | 135 | | | | | 140 | | | | |

| Glu | Lys | Arg | Tyr | Phe | Glu | Pro | Gly | Asp | Leu | Gly | Phe | Pro | Val | Tyr | Asp |
|---|---|---|---|---|---|---|---|---|---|---|---|---|---|---|---|
| 145 | | | | | 150 | | | | | 155 | | | | | 160 |

| Val | Asp | Ala | Ala | Lys | Met | Gly | Met | Phe | Ile | Cys | Asn | Asp | Arg | Arg | Trp |
|---|---|---|---|---|---|---|---|---|---|---|---|---|---|---|---|
| | | | | 165 | | | | | 170 | | | | | 175 | |

| Pro | Glu | Ala | Trp | Arg | Val | Met | Gly | Leu | Arg | Gly | Ala | Glu | Ile | Ile | Cys |
|---|---|---|---|---|---|---|---|---|---|---|---|---|---|---|---|
| | | | 180 | | | | | 185 | | | | | 190 | | |

| Gly | Gly | Tyr | Asn | Thr | Pro | Thr | His | Asn | Pro | Glu | Val | Pro | Gln | His | Asp |
|---|---|---|---|---|---|---|---|---|---|---|---|---|---|---|---|
| | | | 195 | | | | | 200 | | | | | 205 | | |

| His | Leu | Thr | Ser | Phe | His | His | Leu | Leu | Ser | Met | Gln | Ala | Gly | Ser | Tyr |
|---|---|---|---|---|---|---|---|---|---|---|---|---|---|---|---|
| | 210 | | | | | 215 | | | | | 220 | | | | |

| Gln | Asn | Gly | Ala | Trp | Ser | Ala | Ala | Gly | Lys | Ser | Gly | Met | Glu | Glu |
|---|---|---|---|---|---|---|---|---|---|---|---|---|---|---|
| 225 | | | | | 230 | | | | | 235 | | | | | 240 |

| Asn | Cys | Met | Leu | Leu | Gly | His | Ser | Cys | Ile | Val | Ala | Pro | Thr | Gly | Glu |
|---|---|---|---|---|---|---|---|---|---|---|---|---|---|---|---|
| | | | | 245 | | | | | 250 | | | | | 255 | |

| Ile | Val | Ala | Leu | Thr | Thr | Thr | Leu | Glu | Asp | Glu | Val | Ile | Thr | Ala | Ala |
|---|---|---|---|---|---|---|---|---|---|---|---|---|---|---|---|
| | | | | 260 | | | | | 265 | | | | | 270 | |

| Val | Asp | Leu | Asp | Arg | Cys | Arg | Glu | Leu | Arg | Glu | His | Ile | Phe | Asn | Phe |
|---|---|---|---|---|---|---|---|---|---|---|---|---|---|---|---|
| | | 275 | | | | | 280 | | | | | 285 | | | |

| Lys | Gln | His | Arg | Gln | Pro | Gln | His | Tyr | Gly | Leu | Ile | Ala | Glu | Leu |
|---|---|---|---|---|---|---|---|---|---|---|---|---|---|---|
| 290 | | | | | 295 | | | | | 300 | | | | | |

(2) INFORMATION FOR SEQ ID NO:53:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD461

(ix) FEATURE:
        (A) NAME/KEY: CDS
        (B) LOCATION: join(7..915)

(xi) SEQUENCE DESCRIPTION: SEQ ID NO:53:

```
CATATG ACA CGT CAG ATG ATA CTT GCA GTG GGA CAA CAA GGT CCG ATC        48
       Thr Arg Gln Met Ile Leu Ala Val Gly Gln Gln Gly Pro Ile
        1               5                  10

GCG CGC GCG GAG ACA CGC GAA CAG GTC GTC GTT CGT CTT CTC GAC ATG       96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA      144
Leu Thr Lys Ala Ala Ser Arg Gly Ala Asn Phe Ile Val Phe Pro Glu
                 35                  40                  45

CTC GCG CTT ACG ACC TTC TTC CCG CGC TGG CAT TTC ACC GAC GAG GCC      192
Leu Ala Leu Thr Thr Phe Phe Pro Arg Trp His Phe Thr Asp Glu Ala
             50                  55                  60

GAG CTC GAT AGC TTC TAT GAG ACC GAA ATG CCC GGC CCG GTG GTC CGT      240
Glu Leu Asp Ser Phe Tyr Glu Thr Glu Met Pro Gly Pro Val Val Arg
         65                  70                  75

CCA CTC TTT GAG AAG GCC GCG GAA CTC GGG ATC GGC TTC AAT CTG GGC      288
Pro Leu Phe Glu Lys Ala Ala Glu Leu Gly Ile Gly Phe Asn Leu Gly
     80                  85                  90

TAC GCT GAA CTC GTC GTC GAA GGC GGC GTC AAG CGT CGC TTC AAC ACG      336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG      384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG      432
Ile His Leu Pro Gly His Lys Glu Tyr Glu Ala Tyr Arg Pro Phe Gln
            130                 135                 140

CAT CTT GAA AAG CGT TAT TTC GAG CCG GGC GAT CTC GGC TTC CCG GTC      480
His Leu Glu Lys Arg Tyr Phe Glu Pro Gly Asp Leu Gly Phe Pro Val
        145                 150                 155

TAT GAC GTC GAC GCC GCG AAA ATG GGG ATG TTC ATC TGC AAC GAT CGC      528
Tyr Asp Val Asp Ala Ala Lys Met Gly Met Phe Ile Cys Asn Asp Arg
    160                 165                 170

CGC TGG CCT GAA GCC TGG CGG GTG ATG GGC CTC AGG GGC GCC GAG ATC      576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC GAA GTT CCC CAG      624
Ile Cys Gly Gly Tyr Asn Thr Pro Thr His Asn Pro Glu Val Pro Gln
                195                 200                 205

CAC GAC CAC CTG ACG TCC TTC CAC CAT CTC CTA TCG ATG CAG GCC GGG      672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG      720
Ser Tyr Gln Asn Gly Ala Trp Ser Ala Ala Ala Gly Lys Ala Gly Met
        225                 230                 235

GAG GAG AAC TGC ATG CTG CTC GGC CAC TCC TGC ATC GTG GCG CCG ACC      768
Glu Glu Asn Cys Met Leu Leu Gly His Ser Cys Ile Val Ala Pro Thr
    240                 245                 250

GGG GAA ATC GTC GCT CTC ACT ACG ACG CTG GAA GAC GAG GTG ATC ACC      816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC      864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA      912
Asn Phe Lys Gln His Arg Gln Pro Gln His Tyr Gly Leu Ile Ala Glu
            290                 295                 300
```

```
CTC TGAGGTTGCC GAAAAGCATG TGTGTCGTTG TTCTCGGCGC CTGGGTCACA       965
Leu

TCCAGGCGCG CCAGGGTGAC GCTGGTGGAA TAGTACCACG ACCGCTTCAG GGCGATCCGC  1025

AAGGAGATGC GGGTCGCCGG AGCGGCAAAG CCCGACATTC GTTTCGCACC GACGGCCGTC  1085

GTGAACTCGA CAGTCCGCGA GAAGGGCGTA TTGCGCGGCC TGGACCTGTA CGTGGAACTG  1145

TAGCCCATAT ATAGATTTCC AAAGAGTTTC GGCGAGGCGC GGCGCGCCTA GCCCCATGTG  1205

AGCGAGAACC GTGCCCAGAT CAAAGAATGA GACCGACGCG CCGGCCGCGG CAAAGGATGA  1265

TCCTCAGGGT CGGATCTATC GCTCCGCCCT GAAGCAGGAG GGCGCACGCT GGCTGCTGAC  1325

GGCGGAGGAA GGGTTGCTGG CAAAGCCCAA GCCGCCCGGC CTTGTTCCGG CACTTGAGAA  1385

TGCGATCGCC ATCGTCGATT ACATCAACGG TACACCGCCC CATATCGCGT CCCTGGCGGA  1445

GCTTTCAACG ACGCTCGGGA TATCCAAGAG CCACTGTCAC TCCATCCTCA AGACGCTGAC  1505

GCATTTCGGC TGGCTGAAAT TCGACAATCG CTCAAAGAGC TACGAGCTGA ATTC        1559
```

(2) INFORMATION FOR SEQ ID NO:54:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:54:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
                35                  40                  45

Leu Thr Thr Phe Phe Pro Arg Trp His Phe Thr Asp Glu Ala Glu Leu
            50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
                100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Glu Val Pro Gln His Asp
            195                 200                 205

His Leu Thr Ser Phe His His Leu Leu Ser Met Gln Ala Gly Ser Tyr
        210                 215                 220

Gln Asn Gly Ala Trp Ser Ala Ala Gly Lys Ala Gly Met Glu Glu
225                 230                 235                 240
```

```
Asn Cys Met Leu Leu Gly His Ser Cys Ile Val Ala Pro Thr Gly Glu
            245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
            275                 280                 285

Lys Gln His Arg Gln Pro Gln His Tyr Gly Leu Ile Ala Glu Leu
            290                 295                 300
```

(2) INFORMATION FOR SEQ ID NO:55:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD454

(ix) FEATURE:
        (A) NAME/KEY: CDS
        (B) LOCATION: join(233..1141)

(xi) SEQUENCE DESCRIPTION: SEQ ID NO:55:

```
GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA         235
                                                        Thr
                                                         1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
             5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
     35                  40                  45

ACG ACC TTC TTC CCG CGC TGG TAT TTC ACC GAC GAG GCC GAG CTC GAT      427
Thr Thr Phe Phe Pro Arg Trp Tyr Phe Thr Asp Glu Ala Glu Leu Asp
 50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
                 70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
             85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145
```

```
AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
        180                 185                 190

GGC TAC AAC ACG CCG ACC CAC AAT CCC GAA GTT CCC CAG CAC GAC CAC      859
Gly Tyr Asn Thr Pro Thr His Asn Pro Glu Val Pro Gln His Asp His
    195                 200                 205

CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCA GGC ATG GAG GAG AAC      955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC              1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG    1201

CCAGGGTGAC GCTGGTGGAA TAGTACCACG ACCGCTTCAG GGCGATCCGC AAGGAGATGC    1261

GGGTCGCCGG AGCGGCAAAG CCCGACATTC GTTTCGCACC GACGGCCGTC GTGAACTCGA    1321

CAGTCCGCGA GAAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785

(2) INFORMATION FOR SEQ ID NO:56:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:56:

Thr Arg Gln Met Ile Leu Ala Val Gly Gln Gln Gly Pro Ile Ala Arg
  1               5                  10                  15

Ala Glu Thr Arg Glu Gln Val Val Val Arg Leu Leu Asp Met Leu Thr
```

```
                  20                  25                  30
Lys Ala Ala Ser Arg Gly Ala Asn Phe Ile Val Phe Pro Glu Leu Ala
             35                  40                  45
Leu Thr Thr Phe Phe Pro Arg Trp Tyr Phe Thr Asp Glu Ala Glu Leu
         50                  55                  60
Asp Ser Phe Tyr Glu Thr Glu Met Pro Gly Pro Val Val Arg Pro Leu
 65                  70                  75                  80
Phe Glu Lys Ala Ala Glu Leu Gly Ile Gly Phe Asn Leu Gly Tyr Ala
                 85                  90                  95
Glu Leu Val Val Glu Gly Val Lys Arg Arg Phe Asn Thr Ser Ile
                100                 105                 110
Leu Val Asp Lys Ser Gly Lys Ile Val Gly Lys Tyr Arg Lys Ile His
            115                 120                 125
Leu Pro Gly His Lys Glu Tyr Glu Ala Tyr Arg Pro Phe Gln His Leu
        130                 135                 140
Glu Lys Arg Tyr Phe Glu Pro Gly Asp Leu Gly Phe Pro Val Tyr Asp
145                 150                 155                 160
Val Asp Ala Ala Lys Met Gly Met Phe Ile Cys Asn Asp Arg Arg Trp
                165                 170                 175
Pro Glu Ala Trp Arg Val Met Gly Leu Arg Gly Ala Glu Ile Ile Cys
            180                 185                 190
Gly Gly Tyr Asn Thr Pro Thr His Asn Pro Glu Val Pro Gln His Asp
        195                 200                 205
His Leu Thr Ser Phe His His Leu Leu Ser Met Gln Ala Gly Ser Tyr
    210                 215                 220
Gln Asn Gly Ala Trp Ser Ala Ala Gly Lys Ser Gly Met Glu Glu
225                 230                 235                 240
Asn Cys Met Leu Leu Gly His Ser Cys Ile Val Ala Pro Thr Gly Glu
                245                 250                 255
Ile Val Ala Leu Thr Thr Thr Leu Glu Asp Glu Val Ile Thr Ala Ala
            260                 265                 270
Val Asp Leu Asp Arg Cys Arg Glu Leu Arg Glu His Ile Phe Asn Phe
        275                 280                 285
Lys Gln His Arg Gln Pro Gln His Tyr Gly Leu Ile Ala Glu Leu
    290                 295                 300

(2) INFORMATION FOR SEQ ID NO:57:

(i) SEQUENCE CHARACTERISTICS:
        (A) LENGTH: 1559 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD455 (FERM BP-4036)

(ix) FEATURE:
        (A) NAME/KEY: CDS
        (B) LOCATION: join(7..915)

(xi) SEQUENCE DESCRIPTION: SEQ ID NO:57:

CATATG ACA CGT CAG ATG ATA CTT GCA GTG GGA CAA CAA GGT CCG ATC        48
       Thr Arg Gln Met Ile Leu Ala Val Gly Gln Gln Gly Pro Ile
         1               5                  10

GCG CGC GCG GAG ACA CGC GAA CAG GTC GTC GTT CGT CTT CTC GAC ATG        96
```

-continued

```
Ala Arg Ala Glu Thr Arg Glu Gln Val Val Arg Leu Leu Asp Met
 15              20                  25                  30

CTG ACG AAA GCC GCG AGC CGG GGC GCG AAT TTC ATT GTC TTC CCC GAA       144
Leu Thr Lys Ala Ala Ser Arg Gly Ala Asn Phe Ile Val Phe Pro Glu
                 35                  40                  45

CTC GCG CTT ACG ACC TTC TTC CCG CGC TGG TAT TTC ACC GAC GAG GCC       192
Leu Ala Leu Thr Thr Phe Phe Pro Arg Trp Tyr Phe Thr Asp Glu Ala
             50                  55                  60

GAG CTC GAT AGC TTC TAT GAG ACC GAA ATG CCC GGC CCG GTG GTC CGT       240
Glu Leu Asp Ser Phe Tyr Glu Thr Glu Met Pro Gly Pro Val Val Arg
         65                  70                  75

CCA CTC TTT GAG AAG GCC GCG GAA CTC GGG ATC GGC TTC AAT CTG GGC       288
Pro Leu Phe Glu Lys Ala Ala Glu Leu Gly Ile Gly Phe Asn Leu Gly
     80                  85                  90

TAC GCT GAA CTC GTC GTC GAA GGC GGC GTC AAG CGT CGC TTC AAC ACG       336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG       384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG       432
Ile His Leu Pro Gly His Lys Glu Tyr Glu Ala Tyr Arg Pro Phe Gln
            130                 135                 140

CAT CTT GAA AAG CGT TAT TTC GAG CCG GGC GAT CTC GGC TTC CCG GTC       480
His Leu Glu Lys Arg Tyr Phe Glu Pro Gly Asp Leu Gly Phe Pro Val
        145                 150                 155

TAT GAC GTC GAC GCC GCG AAA ATG GGG ATG TTC ATC TGC AAC GAT CGC       528
Tyr Asp Val Asp Ala Ala Lys Met Gly Met Phe Ile Cys Asn Asp Arg
    160                 165                 170

CGC TGG CCT GAA GCC TGG CGG GTG ATG GGC CTC AGG GGC GCC GAG ATC       576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC GAA GTT CCC CAG       624
Ile Cys Gly Gly Tyr Asn Thr Pro Thr His Asn Pro Glu Val Pro Gln
                195                 200                 205

CAC GAC CAC CTG ACG TCC TTC CAC CAT CTC CTA TCG ATG CAG GCC GGG       672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG       720
Ser Tyr Gln Asn Gly Ala Trp Ser Ala Ala Ala Gly Lys Ala Gly Met
        225                 230                 235

GAG GAG AAC TGC ATG CTG CTC GGC CAC TCC TGC ATC GTG GCG CCG ACC       768
Glu Glu Asn Cys Met Leu Leu Gly His Ser Cys Ile Val Ala Pro Thr
    240                 245                 250

GGG GAA ATC GTC GCT CTC ACT ACG ACG CTG GAA GAC GAG GTG ATC ACC       816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC       864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA       912
Asn Phe Lys Gln His Arg Gln Pro Gln His Tyr Gly Leu Ile Ala Glu
            290                 295                 300

CTC TGAGGTTGCC GAAAAGCATG TGTGTCGTTG TTCTCGGCGC CTGGGTCACA            965
Leu

TCCAGGCGCG CCAGGGTGAC GCTGGTGGAA TAGTACCACG ACCGCTTCAG GGCGATCCGC    1025

AAGGAGATGC GGGTCGCCGG AGCGGCAAAG CCCGACATTC GTTTCGCACC GACGGCCGTC    1085

GTGAACTCGA CAGTCCGCGA GAAGGGCGTA TTGCGCGGCC TGGACCTGTA CGTGGAACTG    1145
```

-continued

```
TAGCCCATAT ATAGATTTCC AAAGAGTTTC GGCGAGGCGC GGCGCGCCTA GCCCCATGTG    1205

AGCGAGAACC GTGCCCAGAT CAAAGAATGA GACCGACGCG CCGGCCGCGG CAAAGGATGA    1265

TCCTCAGGGT CGGATCTATC GCTCCGCCCT GAAGCAGGAG GGCGCACGCT GGCTGCTGAC    1325

GGCGGAGGAA GGGTTGCTGG CAAAGCCCAA GCCGCCCGGC CTTGTTCCGG CACTTGAGAA    1385

TGCGATCGCC ATCGTCGATT ACATCAACGG TACACCGCCC CATATCGCGT CCCTGGCGGA    1445

GCTTTCAACG ACGCTCGGGA TATCCAAGAG CCACTGTCAC TCCATCCTCA AGACGCTGAC    1505

GCATTTCGGC TGGCTGAAAT TCGACAATCG CTCAAAGAGC TACGAGCTGA ATTC          1559
```

(2) INFORMATION FOR SEQ ID NO:58:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:58:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
         35                  40                  45

Leu Thr Thr Phe Phe Pro Arg Trp Tyr Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Glu Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270

Val Asp Leu Asp Arg Cys Arg Glu Leu Arg Glu His Ile Phe Asn Phe
```

```
                   275                 280                 285
Lys Gln His Arg Gln Pro Gln His Tyr Gly Leu Ile Ala Glu Leu
    290                 295                 300
```

(2) INFORMATION FOR SEQ ID NO:59:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD456

(ix) FEATURE:
        (A) NAME/KEY: CDS
        (B) LOCATION: join(233..1141)

(xi) SEQUENCE DESCRIPTION: SEQ ID NO:59:

```
GTCGACGGCG GGCTCGCGCG AGAGCTTGTC AAGCAGCGCA AATTCCGGTT CCGCTCCGGT     60

TGACAGATCA AAAATTTTAC GCCTGTTATT GTCGTGCTGC ATGTAATATT TCGTACTTTA    120

TGTAGAATTT GCATTGCGCC GCGAGTCACA AAGCCGGTTT TCGGCGATGT GTTTCACAAC    180

GTTTTCCCGG CCGCTGGGCC GGACATCACC TAGGAAGGAG CAGAGGTTCA TG ACA        235
                                                         Thr
                                                           1

CGT CAG ATG ATA CTT GCA GTG GGA CAA CAA GGT CCG ATC GCG CGC GCG     283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA     331
Glu Thr Arg Glu Gln Val Val Val Arg Leu Leu Asp Met Leu Thr Lys
     20                  25                  30

GCC GCG AGC CGG GGC GCG AAT TTC ATT GTC TTC CCC GAA CTC GCG CTT     379
Ala Ala Ser Arg Gly Ala Asn Phe Ile Val Phe Pro Glu Leu Ala Leu
 35                  40                  45

ACG ACC TTC TTC CCG CGC TGG TAT TTC ACC GAC GAG GCC GAG CTC GAT     427
Thr Thr Phe Phe Pro Arg Trp Tyr Phe Thr Asp Glu Ala Glu Leu Asp
 50                  55                  60                  65

AGC TTC TAT GAG ACC GAA ATG CCC GGC CCG GTG GTC CGT CCA CTC TTT     475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA     523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG     571
Leu Val Val Glu Gly Gly Val Lys Arg Arg Phe Asn Thr Ser Ile Leu
    100                 105                 110

GTG GAT AAG TCA GGC AAG ATC GTC GGC AAG TAT CGT AAG ATC CAT TTG     619
Val Asp Lys Ser Gly Lys Ile Val Gly Lys Tyr Arg Lys Ile His Leu
115                 120                 125

CCG GGT CAC AAG GAG TAC GAG GCC TAC CGG CCG TTC CAG CAT CTT GAA     667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC     715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT     763
Asp Ala Ala Lys Met Gly Met Phe Ile Cys Asn Asp Arg Arg Trp Pro
            165                 170                 175
```

-continued

```
GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
        180                 185                 190

GGC TAC AAC ACG CCG ACC CAC AAT CCC CTT GTT CCC CAG CAC GAC CAC    859
Gly Tyr Asn Thr Pro Thr His Asn Pro Leu Val Pro Gln His Asp His
195                 200                 205

CTG ACG TCC TTC CAC CAT CTC CTA TCG ATG CAG GCC GGG TCT TAT CAG    907
Leu Thr Ser Phe His His Leu Leu Ser Met Gln Ala Gly Ser Tyr Gln
210                 215                 220                 225

AAC GGG GCC TGG TCC GCG GCC GCG GGC AAG TCA GGC ATG GAG GAG AAC    955
Asn Gly Ala Trp Ser Ala Ala Ala Gly Lys Ser Gly Met Glu Glu Asn
                230                 235                 240

TGC ATG CTG CTC GGC CAC TCC TGC ATC GTG GCG CCG ACC GGG GAA ATC   1003
Cys Met Leu Leu Gly His Ser Cys Ile Val Ala Pro Thr Gly Glu Ile
        245                 250                 255

GTC GCT CTC ACT ACG ACG CTG GAA GAC GAG GTG ATC ACC GCC GCC GTC   1051
Val Ala Leu Thr Thr Thr Leu Glu Asp Glu Val Ile Thr Ala Ala Val
            260                 265                 270

GAT CTC GAT CGC TGC CGG GAA CTG CGT GAA CAC ATC TTC AAC TTC AAG   1099
Asp Leu Asp Arg Cys Arg Glu Leu Arg Glu His Ile Phe Asn Phe Lys
275                 280                 285

CAG CAT CGT CAG CCC CAG CAC TAT GGT CTG ATC GCG GAA CTC            1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG  1201

CCAGGGTGAC GCTGGTGGAA TAGTACCACG ACCGCTTCAG GGCGATCCGC AAGGAGATGC  1261

GGGTCGCCGG AGCGGCAAAG CCCGACATTC GTTTCGCACC GACGGCCGTC GTGAACTCGA  1321

CAGTCCGCGA GAAGGGCGTA TTGCGCGGCC TGGACCTGTA CGTGGAACTG TAGCCCATAT  1381

ATAGATTTCC AAAGAGTTTC GGCGAGGCGC GGCGCGCCTA GCCCCATGTG AGCGAGAACC  1441

GTGCCCAGAT CAAAGAATGA GACCGACGCG CCGGCCGCGG CAAAGGATGA TCCTCAGGGT  1501

CGGATCTATC GCTCCGCCCT GAAGCAGGAG GGCGCACGCT GGCTGCTGAC GGCGGAGGAA  1561

GGGTTGCTGG CAAAGCCCAA GCCGCCCGGC CTTGTTCCGG CACTTGAGAA TGCGATCGCC  1621

ATCGTCGATT ACATCAACGG TACACCGCCC CATATCGCGT CCCTGGCGGA GCTTTCAACG  1681

ACGCTCGGGA TATCCAAGAG CCACTGTCAC TCCATCCTCA AGACGCTGAC GCATTTCGGC  1741

TGGCTGAAAT CGACAATCG CTCAAAGAGC TACGAGCTGA ATTC                    1785
```

(2) INFORMATION FOR SEQ ID NO:60:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:60:

```
Thr Arg Gln Met Ile Leu Ala Val Gly Gln Gln Gly Pro Ile Ala Arg
  1               5                  10                  15

Ala Glu Thr Arg Glu Gln Val Val Arg Leu Leu Asp Met Leu Thr
                20                  25                  30

Lys Ala Ala Ser Arg Gly Ala Asn Phe Ile Val Phe Pro Glu Leu Ala
            35                  40                  45

Leu Thr Thr Phe Phe Pro Arg Trp Tyr Phe Thr Asp Glu Ala Glu Leu
        50                  55                  60
```

```
Asp Ser Phe Tyr Glu Thr Glu Met Pro Gly Pro Val Arg Pro Leu
 65                  70                  75                  80

Phe Glu Lys Ala Ala Glu Leu Gly Ile Gly Phe Asn Leu Gly Tyr Ala
             85                  90                  95

Glu Leu Val Val Glu Gly Gly Val Lys Arg Arg Phe Asn Thr Ser Ile
         100                 105                 110

Leu Val Asp Lys Ser Gly Lys Ile Val Gly Lys Tyr Arg Lys Ile His
         115                 120                 125

Leu Pro Gly His Lys Glu Tyr Glu Ala Tyr Arg Pro Phe Gln His Leu
     130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                 165                 170                 175

Pro Glu Ala Trp Arg Val Met Gly Leu Arg Gly Ala Glu Ile Ile Cys
             180                 185                 190

Gly Gly Tyr Asn Thr Pro Thr His Asn Pro Leu Val Pro Gln His Asp
         195                 200                 205

His Leu Thr Ser Phe His His Leu Leu Ser Met Gln Ala Gly Ser Tyr
     210                 215                 220

Gln Asn Gly Ala Trp Ser Ala Ala Gly Lys Ser Gly Met Glu Glu
225                 230                 235                 240

Asn Cys Met Leu Leu Gly His Ser Cys Ile Val Ala Pro Thr Gly Glu
                 245                 250                 255

Ile Val Ala Leu Thr Thr Thr Leu Glu Asp Glu Val Ile Thr Ala Ala
             260                 265                 270

Val Asp Leu Asp Arg Cys Arg Glu Leu Arg Glu His Ile Phe Asn Phe
         275                 280                 285

Lys Gln His Arg Gln Pro Gln His Tyr Gly Leu Ile Ala Glu Leu
     290                 295                 300

(2) INFORMATION FOR SEQ ID NO:61:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD468

(ix) FEATURE:
        (A) NAME/KEY: CDS
        (B) LOCATION: join(233..1141)

(xi) SEQUENCE DESCRIPTION: SEQ ID NO:61:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA    120

TGTAGAATTT GCATTGCGCC GCGAGTCACA AAGCCGGTTT TCGGCGATGT GTTTCACAAC    180

GTTTTCCCGG CCGCTGGGCC GGACATCACC TAGGAAGGAG CAGAGGTTCA TG ACA        235
                                                        Thr
                                                         1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                  10                  15
```

```
GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
            20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
        35                  40                  45

ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
                70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
            85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
    115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
                150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
            165                 170                 175

GAA GCC TGG CGG GTG ATG GGC CTC AGG GGC GCC GAG ATC ATC TGC GGC      811
Glu Ala Trp Arg Val Met Gly Leu Arg Gly Ala Glu Ile Ile Cys Gly
        180                 185                 190

GGC TAC AAC ACG CCG ACC CAC AAT CCC GCT GTT CCC CAG CAC GAC CAC      859
Gly Tyr Asn Thr Pro Thr His Asn Pro Ala Val Pro Gln His Asp His
    195                 200                 205

CTG ACG TCC TTC CAC CAT CTC CTA TCG ATG CAG GCC GGG TCT TAT CAG      907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC      955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC     1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC     1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG     1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC                 1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG     1201

CCAGGGTGAC GCTGGTGGAA TAGTACCACG ACCGCTTCAG GGCGATCCGC AAGGAGATGC     1261

GGGTCGCCGG AGCGGCAAAG CCCGACATTC GTTTCGCACC GACGGCCGTC GTGAACTCGA     1321
```

```
CAGTCCGCGA AAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785
```

(2) INFORMATION FOR SEQ ID NO:62:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:62:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
             20                  25                  30

Lys Ala Ala Ser Arg Gly Ala Asn Phe Ile Val Phe Pro Glu Leu Ala
         35                  40                  45

Leu Thr Thr Phe Phe Pro Arg Trp His Phe Thr Asp Glu Ala Glu Leu
     50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
        115                 120                 125

Leu Pro Gly His Lys Glu Tyr Glu Ala Tyr Arg Pro Phe Gln His Leu
    130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Ala Val Pro Gln His Asp
        195                 200                 205

His Leu Thr Ser Phe His His Leu Leu Ser Met Gln Ala Gly Ser Tyr
    210                 215                 220

Gln Asn Gly Ala Trp Ser Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270
```

```
Val Asp Leu Asp Arg Cys Arg Glu Leu Arg Glu His Ile Phe Asn Phe
        275                 280                 285

Lys Gln His Arg Gln Pro Gln His Tyr Gly Leu Ile Ala Glu Leu
        290                 295                 300

(2) INFORMATION FOR SEQ ID NO:63:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli
         (B) STRAIN: JM109 pAD469

(ix) FEATURE:
         (A) NAME/KEY: CDS
         (B) LOCATION: join(233..1141)

(xi) SEQUENCE DESCRIPTION: SEQ ID NO:63:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA    120

TGTAGAATTT GCATTGCGCC GCGAGTCACA AAGCCGGTTT TCGGCGATGT GTTTCACAAC    180

GTTTTCCCGG CCGCTGGGCC GGACATCACC TAGGAAGGAG CAGAGGTTCA TG ACA        235
                                                         Thr
                                                          1

CGT CAG ATG ATA CTT GCA GTG GGA CAA CAA GGT CCG ATC GCG CGC GCG      283
Arg Gln Met Ile Leu Ala Val Gly Gln Gln Gly Pro Ile Ala Arg Ala
         5                  10                  15

GAG ACA CGC GAA CAG GTC GTC GTT CGT CTT CTC GAC ATG CTG ACG AAA      331
Glu Thr Arg Glu Gln Val Val Val Arg Leu Leu Asp Met Leu Thr Lys
         20                  25                  30

GCC GCG AGC CGG GGC GCG AAT TTC ATT GTC TTC CCC GAA CTC GCG CTT      379
Ala Ala Ser Arg Gly Ala Asn Phe Ile Val Phe Pro Glu Leu Ala Leu
 35                  40                  45

ACG ACC TTC TTC CCG CGC TGG CAT TTC ACC GAC GAG GCC GAG CTC GAT      427
Thr Thr Phe Phe Pro Arg Trp His Phe Thr Asp Glu Ala Glu Leu Asp
 50                  55                  60                  65

AGC TTC TAT GAG ACC GAA ATG CCC GGC CCG GTG GTC CGT CCA CTC TTT      475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA      523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG      571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG      619
Val Asp Lys Ser Gly Lys Ile Val Gly Lys Tyr Arg Lys Ile His Leu
 115                 120                 125

CCG GGT CAC AAG GAG TAC GAG GCC TAC CGG CCG TTC CAG CAT CTT GAA      667
Pro Gly His Lys Glu Tyr Glu Ala Tyr Arg Pro Phe Gln His Leu Glu
 130                 135                 140                 145

AAG CGT TAT TTC GAG CCG GGC GAT CTC GGC TTC CCG GTC TAT GAC GTC      715
Lys Arg Tyr Phe Glu Pro Gly Asp Leu Gly Phe Pro Val Tyr Asp Val
             150                 155                 160

GAC GCC GCG AAA ATG GGG ATG TTC ATC TGC AAC GAT CGC CGC TGG CCT      763
Asp Ala Ala Lys Met Gly Met Phe Ile Cys Asn Asp Arg Arg Trp Pro
```

```
                165                 170                 175
GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
            180                 185                 190

GGC TAC AAC ACG CCG ACC CAC AAT CCC ATT GTT CCC CAG CAC GAC CAC    859
Gly Tyr Asn Thr Pro Thr His Asn Pro Ile Val Pro Gln His Asp His
    195                 200                 205

CTG ACG TCC TTC CAC CAT CTC CTA TCG ATG CAG GCC GGG TCT TAT CAG    907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC    955
Asn Gly Ala Trp Ser Ala Ala Ala Gly Lys Val Gly Met Glu Glu Asn
                230                 235                 240

TGC ATG CTG CTC GGC CAC TCC TGC ATC GTG GCG CCG ACC GGG GAA ATC    1003
Cys Met Leu Leu Gly His Ser Cys Ile Val Ala Pro Thr Gly Glu Ile
            245                 250                 255

GTC GCT CTC ACT ACG ACG CTG GAA GAC GAG GTG ATC ACC GCC GCC GTC    1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG    1099
Asp Leu Asp Arg Cys Arg Glu Leu Arg Glu His Ile Phe Asn Phe Lys
    275                 280                 285

CAG CAT CGT CAG CCC CAG CAC TAT GGT CTG ATC GCG GAA CTC            1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG    1201

CCAGGGTGAC GCTGGTGGAA TAGTACCACG ACCGCTTCAG GGCGATCCGC AAGGAGATGC    1261

GGGTCGCCGG AGCGGCAAAG CCCGACATTC GTTTCGCACC GACGGCCGTC GTGAACTCGA    1321

CAGTCCGCGA GAAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                     1785

(2) INFORMATION FOR SEQ ID NO:64:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:64:

Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
        35                  40                  45

Leu Thr Thr Phe Phe Pro Arg Trp His Phe Thr Asp Glu Ala Glu Leu
    50                  55                  60
```

```
Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Val Lys Arg Arg Phe Asn Thr Ser Ile
            100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
            130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
                180                 185                 190

Gly Gly Tyr Asn Thr Pro Thr His Asn Pro Ile Val Pro Gln His Asp
                195                 200                 205

His Leu Thr Ser Phe His His Leu Leu Ser Met Gln Ala Gly Ser Tyr
210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
                275                 280                 285

Lys Gln His Arg Gln Pro Gln His Tyr Gly Leu Ile Ala Glu Leu
                290                 295                 300

(2) INFORMATION FOR SEQ ID NO:65:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: JM109 pAD470

(ix) FEATURE:
        (A) NAME/KEY: CDS
        (B) LOCATION: join(233..1141)

(xi) SEQUENCE DESCRIPTION: SEQ ID NO:65:

GTCGACGGCG GGCTCGCGCG AGAGCTTGTC AAGCAGCGCA AATTCCGGTT CCGCTCCGGT      60

TGACAGATCA AAAATTTTAC GCCTGTTATT GTCGTGCTGC ATGTAATATT TCGTACTTTA     120

TGTAGAATTT GCATTGCGCC GCGAGTCACA AAGCCGGTTT TCGGCGATGT GTTTCACAAC     180

GTTTTCCCGG CCGCTGGGCC GGACATCACC TAGGAAGGAG CAGAGGTTCA TG ACA          235
                                                        Thr
                                                         1

CGT CAG ATG ATA CTT GCA GTG GGA CAA CAA GGT CCG ATC GCG CGC GCG        283
Arg Gln Met Ile Leu Ala Val Gly Gln Gln Gly Pro Ile Ala Arg Ala
```

-continued

|     |     |     |     | 5   |     |     |     |     | 10  |     |     |     |     | 15  |     |     |      |
|-----|-----|-----|-----|-----|-----|-----|-----|-----|-----|-----|-----|-----|-----|-----|-----|-----|------|
| GAG | ACA | CGC | GAA | CAG | GTC | GTC | GTT | CGT | CTT | CTC | GAC | ATG | CTG | ACG | AAA |     | 331  |
| Glu | Thr | Arg | Glu | Gln | Val | Val | Val | Arg | Leu | Leu | Asp | Met | Leu | Thr | Lys |     |      |
|     |     |     |     | 20  |     |     |     |     | 25  |     |     |     |     | 30  |     |     |      |

GCC GCG AGC CGG GGC GCG AAT TTC ATT GTC TTC CCC GAA CTC GCG CTT    379
Ala Ala Ser Arg Gly Ala Asn Phe Ile Val Phe Pro Glu Leu Ala Leu
         35                  40                  45

ACG ACC TTC TTC CCG CGC TGG CAT TTC ACC GAC GAG GCC GAG CTC GAT    427
Thr Thr Phe Phe Pro Arg Trp His Phe Thr Asp Glu Ala Glu Leu Asp
 50              55                  60                  65

AGC TTC TAT GAG ACC GAA ATG CCC GGC CCG GTG GTC CGT CCA CTC TTT    475
Ser Phe Tyr Glu Thr Glu Met Pro Gly Pro Val Val Arg Pro Leu Phe
             70                  75                  80

GAG AAG GCC GCG GAA CTC GGG ATC GGC TTC AAT CTG GGC TAC GCT GAA    523
Glu Lys Ala Ala Glu Leu Gly Ile Gly Phe Asn Leu Gly Tyr Ala Glu
         85                  90                  95

CTC GTC GTC GAA GGC GGC GTC AAG CGT CGC TTC AAC ACG TCC ATT TTG    571
Leu Val Val Glu Gly Gly Val Lys Arg Arg Phe Asn Thr Ser Ile Leu
        100                 105                 110

GTG GAT AAG TCA GGC AAG ATC GTC GGC AAG TAT CGT AAG ATC CAT TTG    619
Val Asp Lys Ser Gly Lys Ile Val Gly Lys Tyr Arg Lys Ile His Leu
        115                 120                 125

CCG GGT CAC AAG GAG TAC GAG GCC TAC CGG CCG TTC CAG CAT CTT GAA    667
Pro Gly His Lys Glu Tyr Glu Ala Tyr Arg Pro Phe Gln His Leu Glu
130             135                 140                 145

AAG CGT TAT TTC GAG CCG GGC GAT CTC GGC TTC CCG GTC TAT GAC GTC    715
Lys Arg Tyr Phe Glu Pro Gly Asp Leu Gly Phe Pro Val Tyr Asp Val
            150                 155                 160

GAC GCC GCG AAA ATG GGG ATG TTC ATC TGC AAC GAT CGC CGC TGG CCT    763
Asp Ala Ala Lys Met Gly Met Phe Ile Cys Asn Asp Arg Arg Trp Pro
        165                 170                 175

GAA GCC TGG CGG GTG ATG GGC CTC AGG GGC GCC GAG ATC ATC TGC GGC    811
Glu Ala Trp Arg Val Met Gly Leu Arg Gly Ala Glu Ile Ile Cys Gly
        180                 185                 190

GGC TAC AAC ACG CCG ACC CAC AAT CCC CAT GTT CCC CAG CAC GAC CAC    859
Gly Tyr Asn Thr Pro Thr His Asn Pro His Val Pro Gln His Asp His
195                 200                 205

CTG ACG TCC TTC CAC CAT CTC CTA TCG ATG CAG GCC GGG TCT TAT CAG    907
Leu Thr Ser Phe His His Leu Leu Ser Met Gln Ala Gly Ser Tyr Gln
210                 215                 220                 225

AAC GGG GCC TGG TCC GCG GCC GCG GGC AAG GTG GGC ATG GAG GAG AAC    955
Asn Gly Ala Trp Ser Ala Ala Ala Gly Lys Val Gly Met Glu Glu Asn
            230                 235                 240

TGC ATG CTG CTC GGC CAC TCC TGC ATC GTG GCG CCG ACC GGG GAA ATC    1003
Cys Met Leu Leu Gly His Ser Cys Ile Val Ala Pro Thr Gly Glu Ile
        245                 250                 255

GTC GCT CTC ACT ACG ACG CTG GAA GAC GAG GTG ATC ACC GCC GCC GTC    1051
Val Ala Leu Thr Thr Thr Leu Glu Asp Glu Val Ile Thr Ala Ala Val
        260                 265                 270

GAT CTC GAT CGC TGC CGG GAA CTG CGT GAA CAC ATC TTC AAC TTC AAG    1099
Asp Leu Asp Arg Cys Arg Glu Leu Arg Glu His Ile Phe Asn Phe Lys
        275                 280                 285

CAG CAT CGT CAG CCC CAG CAC TAT GGT CTG ATC GCG GAA CTC                1141
Gln His Arg Gln Pro Gln His Tyr Gly Leu Ile Ala Glu Leu
290                 295                 300

TGAGGTTGCC GAAAAGCATG TGTGTCGTTG TTCTCGGCGC CTGGGTCACA TCCAGGCGCG    1201

CCAGGGTGAC GCTGGTGGAA TAGTACCACG ACCGCTTCAG GGCGATCCGC AAGGAGATGC    1261

GGGTCGCCGG AGCGGCAAAG CCCGACATTC GTTTCGCACC GACGGCCGTC GTGAACTCGA    1321

```
CAGTCCGCGA AAGGGCGTA TTGCGCGGCC TGGACCTGTA CGTGGAACTG TAGCCCATAT    1381

ATAGATTTCC AAAGAGTTTC GGCGAGGCGC GGCGCGCCTA GCCCCATGTG AGCGAGAACC    1441

GTGCCCAGAT CAAAGAATGA GACCGACGCG CCGGCCGCGG CAAAGGATGA TCCTCAGGGT    1501

CGGATCTATC GCTCCGCCCT GAAGCAGGAG GGCGCACGCT GGCTGCTGAC GGCGGAGGAA    1561

GGGTTGCTGG CAAAGCCCAA GCCGCCCGGC CTTGTTCCGG CACTTGAGAA TGCGATCGCC    1621

ATCGTCGATT ACATCAACGG TACACCGCCC CATATCGCGT CCCTGGCGGA GCTTTCAACG    1681

ACGCTCGGGA TATCCAAGAG CCACTGTCAC TCCATCCTCA AGACGCTGAC GCATTTCGGC    1741

TGGCTGAAAT TCGACAATCG CTCAAAGAGC TACGAGCTGA ATTC                    1785
```

(2) INFORMATION FOR SEQ ID NO:66:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:66:

```
Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
         35                  40                  45

Leu Thr Thr Phe Phe Pro Arg Trp His Phe Thr Asp Glu Ala Glu Leu
 50                  55                  60

Asp Ser Phe Tyr Glu Thr Glu Met Pro Gly Pro Val Val Arg Pro Leu
 65                  70                  75                  80

Phe Glu Lys Ala Ala Glu Leu Gly Ile Gly Phe Asn Leu Gly Tyr Ala
                 85                  90                  95

Glu Leu Val Val Glu Gly Val Lys Arg Arg Phe Asn Thr Ser Ile
            100                 105                 110

Leu Val Asp Lys Ser Gly Lys Ile Val Gly Lys Tyr Arg Lys Ile His
         115                 120                 125

Leu Pro Gly His Lys Glu Tyr Glu Ala Tyr Arg Pro Phe Gln His Leu
130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro His Val Pro Gln His Asp
         195                 200                 205

His Leu Thr Ser Phe His His Leu Leu Ser Met Gln Ala Gly Ser Tyr
210                 215                 220

Gln Asn Gly Ala Trp Ser Ala Ala Ala Gly Lys Val Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
            260                 265                 270
```

```
                 Val Asp Leu Asp Arg Cys Arg Glu Leu Arg Glu His Ile Phe Asn Phe
                         275                 280                 285

Lys Gln His Arg Gln Pro Gln His Tyr Gly Leu Ile Ala Glu Leu
                         290                 295                 300

(2) INFORMATION FOR SEQ ID NO:67:

(i) SEQUENCE CHARACTERISTICS:
        (A) LENGTH: 926 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Escherichia coli
         (B) STRAIN: HB101 pNT4553 (FERM BP-4368)

(ix) FEATURE:
         (A) NAME/KEY: CDS
         (B) LOCATION: join(7..915)

(xi) SEQUENCE DESCRIPTION: SEQ ID NO:67:

CATATG ACA CGT CAG ATG ATA CTT GCA GTG GGA CAA CAA GGT CCG ATC              48
       Thr Arg Gln Met Ile Leu Ala Val Gly Gln Gln Gly Pro Ile
         1               5                  10

GCG CGC GCG GAG ACA CGC GAA CAG GTC GTC GTT CGT CTT CTC GAC ATG             96
Ala Arg Ala Glu Thr Arg Glu Gln Val Val Val Arg Leu Leu Asp Met
 15              20                  25                  30

CTG ACG AAA GCC GCG AGC CGG GGC GCG AAT TTC ATT GTC TTC CCC GAA            144
Leu Thr Lys Ala Ala Ser Arg Gly Ala Asn Phe Ile Val Phe Pro Glu
             35                  40                  45

CTC GCG CTT ACG ACC TTC TTC CCG CGC TGG TAT TTC ACC GAC GAG GCC            192
Leu Ala Leu Thr Thr Phe Phe Pro Arg Trp Tyr Phe Thr Asp Glu Ala
                 50                  55                  60

GAG CTC GAT AGC TTC TAT GAG ACC GAA ATG CCC GGC CCG GTG GTC CGT            240
Glu Leu Asp Ser Phe Tyr Glu Thr Glu Met Pro Gly Pro Val Val Arg
             65                  70                  75

CCA CTC TTT GAG AAG GCC GCG GAA CTC GGG ATC GGC TTC AAT CTG GGC            288
Pro Leu Phe Glu Lys Ala Ala Glu Leu Gly Ile Gly Phe Asn Leu Gly
         80                  85                  90

TAC GCT GAA CTC GTC GTC GAA GGC GGC GTC AAG CGT CGC TTC AAC ACG            336
Tyr Ala Glu Leu Val Val Glu Gly Gly Val Lys Arg Arg Phe Asn Thr
 95                 100                 105                 110

TCC ATT TTG GTG GAT AAG TCA GGC AAG ATC GTC GGC AAG TAT CGT AAG            384
Ser Ile Leu Val Asp Lys Ser Gly Lys Ile Val Gly Lys Tyr Arg Lys
                115                 120                 125

ATC CAT TTG CCG GGT CAC AAG GAG TAC GAG GCC TAC CGG CCG TTC CAG            432
Ile His Leu Pro Gly His Lys Glu Tyr Glu Ala Tyr Arg Pro Phe Gln
                130                 135                 140

CAT CTT GAA AAG CGT TAT TTC GAG CCG GGC GAT CTC GGC TTC CCG GTC            480
His Leu Glu Lys Arg Tyr Phe Glu Pro Gly Asp Leu Gly Phe Pro Val
            145                 150                 155

TAT GAC GTC GAC GCC GCG AAA ATG GGG ATG TTC ATC TGC AAC GAT CGC            528
Tyr Asp Val Asp Ala Ala Lys Met Gly Met Phe Ile Cys Asn Asp Arg
        160                 165                 170

CGC TGG CCT GAA GCC TGG CGG GTG ATG GGC CTC AGG GGC GCC GAG ATC            576
Arg Trp Pro Glu Ala Trp Arg Val Met Gly Leu Arg Gly Ala Glu Ile
175                 180                 185                 190

ATC TGC GGC GGC TAC AAC ACG CCG ACC CAC AAT CCC GAA GTT CCC CAG            624
Ile Cys Gly Gly Tyr Asn Thr Pro Thr His Asn Pro Glu Val Pro Gln
                195                 200                 205
```

```
CAC GAC CAC CTG ACG TCC TTC CAC CAT CTC CTA TCG ATG CAG GCC GGG        672
His Asp His Leu Thr Ser Phe His His Leu Leu Ser Met Gln Ala Gly
            210                 215                 220

TCT TAT CAG AAC GGG GCC TGG TCC GCG GCC GCG GGC AAG GCG GGC ATG        720
Ser Tyr Gln Asn Gly Ala Trp Ser Ala Ala Ala Gly Lys Ala Gly Met
                225                 230                 235

GAG GAG AAC TGC ATG CTG CTC GGC CAC TCC TGC ATC GTG GCG CCG ACC        768
Glu Glu Asn Cys Met Leu Leu Gly His Ser Cys Ile Val Ala Pro Thr
        240                 245                 250

GGG GAA ATC GTC GCT CTC ACT ACG ACG CTG GAA GAC GAG GTG ATC ACC        816
Gly Glu Ile Val Ala Leu Thr Thr Thr Leu Glu Asp Glu Val Ile Thr
255                 260                 265                 270

GCC GCC GTC GAT CTC GAT CGC TGC CGG GAA CTG CGT GAA CAC ATC TTC        864
Ala Ala Val Asp Leu Asp Arg Cys Arg Glu Leu Arg Glu His Ile Phe
                275                 280                 285

AAC TTC AAG CAG CAT CGT CAG CCC CAG CAC TAT GGT CTG ATC GCG GAA        912
Asn Phe Lys Gln His Arg Gln Pro Gln His Tyr Gly Leu Ile Ala Glu
                290                 295                 300

CTC TGAGGCTGCA G                                                       926
Leu (2) INFORMATION FOR SEQ ID NO:68:

(i) SEQUENCE CHARACTERISTICS:
        (A) LENGTH: 303 amino acids
        (B) TYPE: amino acid
        (D) TOPOLOGY: linear (ii) MOLECULE TYPE: protein (xi) SEQUENCE DESCRIPTION: SEQ ID NO:68:

Thr Arg Gln Met Ile Leu Ala Val Gly Gln Gln Gly Pro Ile Ala Arg
 1               5                  10                  15

Ala Glu Thr Arg Glu Gln Val Val Arg Leu Leu Asp Met Leu Thr
            20                  25                  30

Lys Ala Ala Ser Arg Gly Ala Asn Phe Ile Val Phe Pro Glu Leu Ala
            35                  40                  45

Leu Thr Thr Phe Phe Pro Arg Trp Tyr Phe Thr Asp Glu Ala Glu Leu
        50                  55                  60

Asp Ser Phe Tyr Glu Thr Glu Met Pro Gly Pro Val Val Arg Pro Leu
65                  70                  75                  80

Phe Glu Lys Ala Ala Glu Leu Gly Ile Gly Phe Asn Leu Gly Tyr Ala
                85                  90                  95

Glu Leu Val Val Glu Gly Gly Val Lys Arg Arg Phe Asn Thr Ser Ile
            100                 105                 110

Leu Val Asp Lys Ser Gly Lys Ile Val Gly Lys Tyr Arg Lys Ile His
            115                 120                 125

Leu Pro Gly His Lys Glu Tyr Glu Ala Tyr Arg Pro Phe Gln His Leu
        130                 135                 140

Glu Lys Arg Tyr Phe Glu Pro Gly Asp Leu Gly Phe Pro Val Tyr Asp
145                 150                 155                 160

Val Asp Ala Ala Lys Met Gly Met Phe Ile Cys Asn Asp Arg Arg Trp
                165                 170                 175

Pro Glu Ala Trp Arg Val Met Gly Leu Arg Gly Ala Glu Ile Ile Cys
            180                 185                 190

Gly Gly Tyr Asn Thr Pro Thr His Asn Pro Glu Val Pro Gln His Asp
            195                 200                 205
```

```
                         -continued

His Leu Thr Ser Phe His His Leu Leu Ser Met Gln Ala Gly Ser Tyr
    210                 215                 220

Gln Asn Gly Ala Trp Ser Ala Ala Gly Lys Ala Gly Met Glu Glu
225                 230                 235                 240

Asn Cys Met Leu Leu Gly His Ser Cys Ile Val Ala Pro Thr Gly Glu
                245                 250                 255

Ile Val Ala Leu Thr Thr Thr Leu Glu Asp Glu Val Ile Thr Ala Ala
                260                 265                 270

Val Asp Leu Asp Arg Cys Arg Glu Leu Arg Glu His Ile Phe Asn Phe
                275                 280                 285

Lys Gln His Arg Gln Pro Gln His Tyr Gly Leu Ile Ala Glu Leu
290                 295                 300

(2) INFORMATION FOR SEQ ID NO:69:

(i) SEQUENCE CHARACTERISTICS:
        (A) LENGTH: 1820 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas
        (B) STRAIN: KNK 003A (FERM BP-3181)

(ix) FEATURE:
        (A) NAME/KEY: CDS
        (B) LOCATION: join(701..1633)

(xi) SEQUENCE DESCRIPTION: SEQ ID NO:69:

GCATGCGCGG GGAACTGAAG AACTTGCAAG ACGAACTCGG CATTACCTTC GTGCATGTAA     60

CCCATACCCA GCCTGAGGCG ATCGCGCTCG CCGACATGGT GGTTGTGATG GATACGGGCC    120

GCATAGAGCA GGCAGCGAGC GCCAACGAAA TCTACAACCG GCCCGCGACG CCCTATGTGG    180

CGCGCTTCAT GGGCGGCCAA AACGTGTTGA CGGGGAGGGT GGAGAGCATC TCGCCCACCG    240

GCATGGTGCT GAAAAGCGAA AAGGGCGAGA TCTTCAATGC GCCTCTTACG GGTGCTGCGC    300

CGAAGCTGGG CGAACCCGTA TCGATATCCA TGCGCCGCGA CCGCATCAGC ATCAGCAAGC    360

CGCAAAACGG CAAGGGCGCG CAGCAGGCTG ACGCGGTAAC GGGTGTGGTC GATTCCACGG    420

AATACCAGGG CAGCTTCGTG AAGGTCAGCA TAGTGCTCGA CGGTGGCGAG ACCTTCGTCG    480

CAAACATGCC CGACCATGAA TTTTTCGCGG AACCGGTGGA TCACGGCGTC CCGGTGGTCG    540

CCCGCTGGAA ACCGGAGCAT GTGCATGTCC TGTCCAAGTC TGACCGGGGC GCCGACCACA    600

CCGAAATCTA CCGCTTCCCT GCAGGCGAAA ATACCGTTTC AATGGGCAAG GGGCGGCAAA    660

CGGGGTTGAG ACGACCCGGT TTATCGAGGA GGACGAGATG ACA CGC ATC GTC AAT      715
                                             Thr Arg Ile Val Asn
                                              1               5

GCA GCC GCC GCG CAG ATG GGG CCC ATC AGC CGG TCC GAA ACG CGC AAG      763
Ala Ala Ala Ala Gln Met Gly Pro Ile Ser Arg Ser Glu Thr Arg Lys
                 10                  15                  20

GAT ACG GTC CGG CGC CTG ATC GCG CTC ATG CGC GAG GCG AAG GCC CGC      811
Asp Thr Val Arg Arg Leu Ile Ala Leu Met Arg Glu Ala Lys Ala Arg
             25                  30                  35

GGT TCC GAC CTT GTC GTC TTT ACC GAA CTC GCG CTC ACC ACC TTC TTT      859
Gly Ser Asp Leu Val Val Phe Thr Glu Leu Ala Leu Thr Thr Phe Phe
         40                  45                  50

CCC CGC TGG GTG ATC GAG GAC GAA GCT GAG CTC GAC AGC TTC TAC GAG      907
Pro Arg Trp Val Ile Glu Asp Glu Ala Glu Leu Asp Ser Phe Tyr Glu
```

```
            55                    60                       65
AAG GAG ATG CCA GGG CCC GAA ACC CAG CCG CTC TTC GAT GAG GCG AAG    955
Lys Glu Met Pro Gly Pro Glu Thr Gln Pro Leu Phe Asp Glu Ala Lys
 70              75                  80                      85

CGC TTG GAG ATC GGC TTC TAT CTC GGT TAT GCC GAG CTG GCG GAG GAG   1003
Arg Leu Glu Ile Gly Phe Tyr Leu Gly Tyr Ala Glu Leu Ala Glu Glu
                 90              95                  100

GGC GGC AGG AAG CGG CGC TTC AAC ACC TCT ATC CTT GTG GAC CGC AGC   1051
Gly Gly Arg Lys Arg Arg Phe Asn Thr Ser Ile Leu Val Asp Arg Ser
            105                 110                 115

GGC CGG ATC GTC GGC AAG TAC CGC AAG GTG CAC CTG CCC GGG CAC AAA   1099
Gly Arg Ile Val Gly Lys Tyr Arg Lys Val His Leu Pro Gly His Lys
        120                 125                 130

GAG CCG CAG CCC GGC AGG AAA CAC CAG CAT CTC GAG AAA CGC TAT TTC   1147
Glu Pro Gln Pro Gly Arg Lys His Gln His Leu Glu Lys Arg Tyr Phe
    135                 140                 145

GAG CCC GGC GAT CTC GGC TTC GGT GTC TGG CGC GCC TTC GAC GGC GTA   1195
Glu Pro Gly Asp Leu Gly Phe Gly Val Trp Arg Ala Phe Asp Gly Val
150                 155                 160                 165

ATG GGC ATG TGC ATT TGC AAC GAC CGC CGC TGG CCG GAG ACC TAC CGG   1243
Met Gly Met Cys Ile Cys Asn Asp Arg Arg Trp Pro Glu Thr Tyr Arg
                170                 175                 180

GTC ATG GGC TTG CAG GGA GTG GAG ATG GTC ATG CTG GGC TAC AAC ACG   1291
Val Met Gly Leu Gln Gly Val Glu Met Val Met Leu Gly Tyr Asn Thr
            185                 190                 195

CCG TAT GAC CAT ACC GGT CAC GAC GAC ATC GAT TCA CTC ACC CAG TTT   1339
Pro Tyr Asp His Thr Gly His Asp Asp Ile Asp Ser Leu Thr Gln Phe
        200                 205                 210

CAC AAT CAT CTC TCC ATG CAG GCG GGC GCC TAC CAG AAT TCG ACC TGG   1387
His Asn His Leu Ser Met Gln Ala Gly Ala Tyr Gln Asn Ser Thr Trp
    215                 220                 225

GTG ATC GGC ACC GCC AAA TGC GGC ACC GAG GAG GGC TCC AAA ATG GTG   1435
Val Ile Gly Thr Ala Lys Cys Gly Thr Glu Glu Gly Ser Lys Met Val
230                 235                 240                 245

GGG CAG AGC GTG ATC GTT GCG CCC TCG GGC GAG ATC GTC GCT ATG GCC   1483
Gly Gln Ser Val Ile Val Ala Pro Ser Gly Glu Ile Val Ala Met Ala
                250                 255                 260

TGC ACG ATC GAG GAC GAG ATC ATC ACC GCA CGC TGC GAT CTC GAC ATG   1531
Cys Thr Ile Glu Asp Glu Ile Ile Thr Ala Arg Cys Asp Leu Asp Met
            265                 270                 275

GGC AAG CGC TAC CGC GAG ACC ATC TTC GAT TTC GCC CGC CAT CGC GAG   1579
Gly Lys Arg Tyr Arg Glu Thr Ile Phe Asp Phe Ala Arg His Arg Glu
        280                 285                 290

CCC GAC GCC TAT CGC CTG ATC GTC GAA CGC AAA GGG GCT GTG CCG CCG   1627
Pro Asp Ala Tyr Arg Leu Ile Val Glu Arg Lys Gly Ala Val Pro Pro
    295                 300                 305

CCG CAG TGATCGGAAC CTGAAAACGA AATATCCCGC CGGACGGTGG GAAGGTGAAA   1683
Pro Gln
310

GGAGGAGTCT CCATGACAAC AGTTATCAAG GGTGGAACAT CGTCGCCGCC GATCGCAGCT   1743

ATGAAGCCGA TATCCTGATC GAAGGCGAAA AGATCGCCCA GATCGGCAGG GATCTGCAGG   1803

GCGACAAGAT TGTCGAC                                                 1820

(2) INFORMATION FOR SEQ ID NO:70:

(i) SEQUENCE CHARACTERISTICS:
          (A) LENGTH: 311 amino acids
          (B) TYPE: amino acid
          (D) TOPOLOGY: linear
```

(ii) MOLECULE TYPE: protein (xi) SEQUENCE DESCRIPTION: SEQ ID NO:70:

```
Thr Arg Ile Val Asn Ala Ala Ala Gln Met Gly Pro Ile Ser Arg
 1               5                  10                  15

Ser Glu Thr Arg Lys Asp Thr Val Arg Arg Leu Ile Ala Leu Met Arg
            20                  25                  30

Glu Ala Lys Ala Arg Gly Ser Asp Leu Val Val Phe Thr Glu Leu Ala
        35                  40                  45

Leu Thr Thr Phe Phe Pro Arg Trp Val Ile Glu Asp Glu Ala Glu Leu
    50                  55                  60

Asp Ser Phe Tyr Glu Lys Glu Met Pro Gly Pro Glu Thr Gln Pro Leu
65                  70                  75                  80

Phe Asp Glu Ala Lys Arg Leu Glu Ile Gly Phe Tyr Leu Gly Tyr Ala
                85                  90                  95

Glu Leu Ala Glu Glu Gly Gly Arg Lys Arg Arg Phe Asn Thr Ser Ile
            100                 105                 110

Leu Val Asp Arg Ser Gly Arg Ile Val Gly Lys Tyr Arg Lys Val His
            115                 120                 125

Leu Pro Gly His Lys Glu Pro Gln Pro Gly Arg Lys His Gln His Leu
        130                 135                 140

Glu Lys Arg Tyr Phe Glu Pro Gly Asp Leu Gly Phe Gly Val Trp Arg
145                 150                 155                 160

Ala Phe Asp Gly Val Met Gly Met Cys Ile Cys Asn Asp Arg Arg Trp
                165                 170                 175

Pro Glu Thr Tyr Arg Val Met Gly Leu Gln Gly Val Glu Met Val Met
            180                 185                 190

Leu Gly Tyr Asn Thr Pro Tyr Asp His Thr Gly His Asp Asp Ile Asp
        195                 200                 205

Ser Leu Thr Gln Phe His Asn His Leu Ser Met Gln Ala Gly Ala Tyr
    210                 215                 220

Gln Asn Ser Thr Trp Val Ile Gly Thr Ala Lys Cys Gly Thr Glu Glu
225                 230                 235                 240

Gly Ser Lys Met Val Gly Gln Ser Val Ile Val Ala Pro Ser Gly Glu
                245                 250                 255

Ile Val Ala Met Ala Cys Thr Ile Glu Asp Glu Ile Ile Thr Ala Arg
            260                 265                 270

Cys Asp Leu Asp Met Gly Lys Arg Tyr Arg Glu Thr Ile Phe Asp Phe
        275                 280                 285

Ala Arg His Arg Glu Pro Asp Ala Tyr Arg Leu Ile Val Glu Arg Lys
    290                 295                 300

Gly Ala Val Pro Pro Pro Gln
305                 310
```

DNA CODING FOR DECARBAMYLASE IMPROVED IN THERMOSTABILITY AND USE THEREOF

This application is a continuation of application Ser. No. 08/211,641, filed Apr. 11, 1994, which is a National Phase Application of PCT/JP93/01101, filed Aug. 5, 1993.

TECHNICAL FIELD

The present invention relates to a DNA fragment, and more particularly, it relates to a DNA fragment coding for a thermostability-improved enzyme capable of converting D-N-carbamoyl-α-amino acids into the corresponding D-α-amino acids (hereinafter referred to as decarbamylase). The present invention also relates to a process for preparing the DNA fragment, a vector comprising the DNA fragment, a transformant obtained by transformation with the vector, a decarbamylase improved in thermostability and its production process, and an improved process for producing amino acids using the decarbamylase. The present invention further relates to a method for increasing, by one or more, the number of mutations in amino acids related to the themostability of a decarbamylase.

BACKGROUND ART

Optically active D-α-amino acids are important compounds as intermediates of medicaments, and in particular, D-phenylglycine, D-parahydroxyphenylglycine and the like, which are intermediates for the production of semi-synthetic penicillins and semisynthetic sepharospolines, are useful compounds from an industrial point of view. As the production process for such D-α-amino acids, a process is known in which these compounds are obtained by the removal of carbamoyl groups of the corresponding D-N-carbamoyl-α-amino acids, wherein the removal of carbamoyl groups is effected by a chemical method (the specification of the Japanese Patent Publication No. 58-4707) or by the utilization of enzyme reactions of microorganisms (the specifications of the Japanese Patent Publication Nos. 57-18793, 63-20520 and 1-48758, and the Japanese Patent Application No. 2-407922).

However, because a mineral acid such as sulfuric acid is used at great amounts in the chemical method employed for the removal of carbamoyl groups, serious problems on the environment may occur in relation to the treatment thereof and the like. On the other hand, the method utilizing an enzyme reaction has disadvantages that the amount of enzyme produced is not satisfactory and there are some difficulties in its properties even if mass production is made possible, so that enzymes with reactivity to substrates and enzyme stability have not yet been found.

In general, some enzymes have poor stability, and when such an enzyme is prepared, a stabilizing agent is added or a means of preventing inactivation such as treatment at low temperatures is employed. When an enzyme is used in an actual reaction at ordinary or high temperatures, attention will be directed to the stability of the enzyme. In particular case where an enzyme is used on an industrial scale, its stability often has an effect upon the product cost. Also, in particular case where an enzyme is used on an industrial scale, as a means of allowing the enzyme reaction to proceed with advantage, the enzyme is repeatedly used in the reaction as a so-called bioreactor such as an immobilized enzyme or immobilized bacterial cells, and even at this time, the stability of the enzyme will give a limitation to the number of use and have an important effect upon the product cost.

In the present invention, attention is paid to the thermostability as an index of the enzyme stability and an improvement in the thermostability of an enzyme is achieved using a genetic engineering means, whereby the stability of this enzyme is increased and this makes it possible to produce a stabilized enzyme having excellent advantages for industrial applications.

To solve such a problem, the present invention has an object to prepare a decarbamylase with high reactivity to D-N-carbamoyl-α-amino acids as the substrate and excellent stability by an improvement of currently available decarbamylases and to produce D-α-amino acids using this enzyme with high efficiency.

SUMMARY OF THE INVENTION

That is, the present invention provides an improved process for producing D-α-amino acids, comprising converting D-N-carbamoyl-α-amino acids into the corresponding D-α-amino acids in an aqueous medium by the action of an enzyme and collecting the D-α-amino acids produced, said enzyme being produced by a transformant which has been obtained by the transformation of a host bacterial cell selected from the microorganisms of the genus Escherichia, Pseudomonas, Flavo-bacterium, Bacillus, Serratia, Corynebacterium or Brevi-bacterium with a gene which has been obtained by a process comprising subjecting a DNA fragment containing a decarbamylase gene to chemical or enzyme mutagenesis, introducing a recombinant DNA having a vector DNA ligated with this DNA fragment into a host cell and screening a strain capable of producing an enzyme improved in thermostability.

Thus, the present invention also provides a DNA fragment for conducting the improved process for producing D-α-amino acids according to the present invention, its production process and an expression vector containing the fragment, a transformed microorganism obtained by transformation with the expression vector, as well as a decarbamylase improved in thermostability and its production process. The present invention further provides a method for increasing, by one or more, the number of mutations in amino acids related to the thermostability of decarbamylases.

The present invention will hereinafter be illustrated by reference to the accompanying drawings.

BRIEF DESCRIPTION OF THE DRAWINGS

FIG. 3 shows restriction maps of plasmids pKK233-2 and pKK NE.

FIG. 4 shows restriction maps of plasmids pAD108 and pAD1086.

FIG. 5 shows restriction maps of plasmids pAD402 and pAD4021.

FIG. 6 shows restriction maps of plasmids pAD429 and pAD455.

FIG. 10 shows a restriction map of plasmid pUC NT and pNT4553.

DETAILED DESCRIPTION OF THE INVENTION

Figure 1:
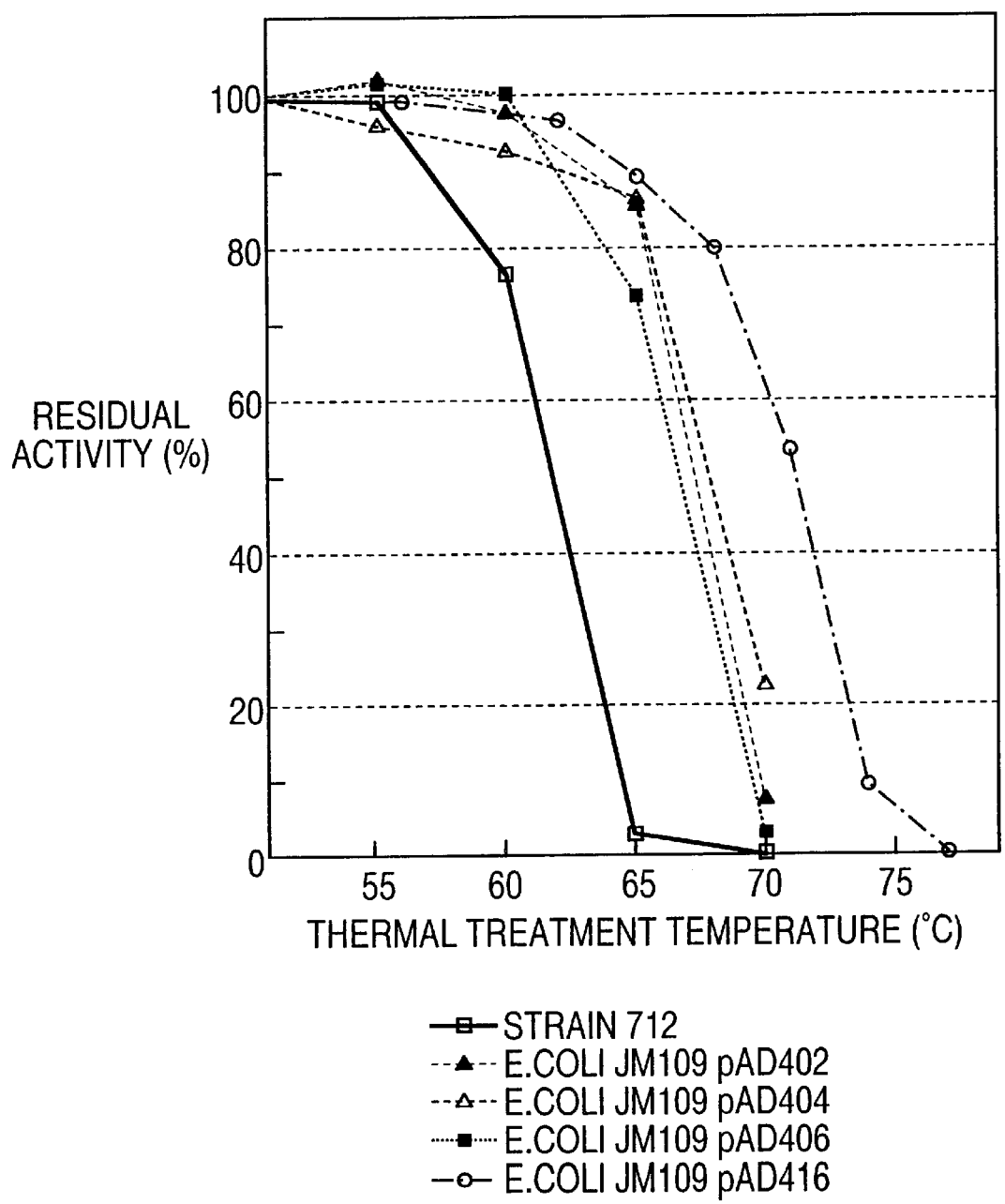
FIG. 1 is a graph showing the thermostable activity of a decarbamylase after thermal treatment, which is obtained by the use of a strain capable of producing the decarbamylase improved in thermostability according to the present invention.

In general, it is known that the thermostability and stability of an enzyme are correlated with each other. It is also known that various enzymes produced by thermophiles are those which have high thermostability and also have high stability with almost no exception, and that enzymes having thermostability given by the substitution of amino acids according to a gene recombination technique also have excellent stability (Kagawa et al., Saibo Kogaku, vol. 7, 509–571 (1988)).

As the method for making an enzyme thermostable, there can be employed a method in which an amino acid sequence of the enzyme protein is changed or a method in which the enzyme is modified by chemical treatment, enzyme reaction or the like. As the method for improving the thermostability by a change in the amino acid sequence of the enzyme protein, there can be employed a method in which bacterial cells are allowed to cause some mutation with a chemically mutagenic agent such as nitrosoguanidine (NTG) or by ultraviolet rays, followed by screening, or a method in which a gene of interest is obtained by a gene recombination technique and then allowed to cause some chemical or enzyme mutation, followed by returning it into the bacterial cell and then screening. When a gene is obtained and allowed to cause some mutation, it is more effective to subject a DNA fragment coding for a decarbamylase protein to mutagenesis in the form of a single strand. To make the fragment into a single-stranded form, there can be employed, for example, a method for incorporating the fragment into phage particles. As the single-stranded DNA, there can be used either a DNA strand containing the codons corresponding to the amino acid sequence of a decarbamylase protein or the complementary strand thereof. Moreover, as to the mutation sites, there can be employed a method for introducing random mutations or a method for introducing site-specific mutations.

As the agent for allowing a gene to cause some random mutation and thereby introducing some mutation into the amino acid sequence of an enzyme protein, there can be used hydroxylamine hydrochloride, sodium nitrite, formic acid, hydrazine or the like.

For example, in the mutagenesis using hydroxylamine hydrochloride, a decarbamylase gene is first ligated with the double-stranded DNA of an M13 phage such as M13mp19, with which E. coli JM109 or the like is infected, and this bacterial culture is incubated to prepare phage particles for use in the mutagenesis. The mutation can be effected by the reaction using hydroxylamine hydrochloride in a concentration of 0.1 to 2 M, desirably 0.25 M, at a pH of 6.0 to 8.0, preferably 6.0, at a temperature of 37° C. for a period of 1 to 24 hours. The phage particles undergoing such a mutagenic reaction are used for the infection of E. coli and recovered as a double-stranded recombinant DNA, followed by the transfer of such a mutant decarbamylase gene to a plasmid.

In the mutagenesis using sodium nitrite, formic acid, hydrazine or the like, there can be basically used a method as described by R. M. Myers, et al. (Science, 229, 242–247 (1985)). This method can be conducted by the preparation of a single-stranded DNA from the recombinant M13 phage having a decarbamylase gene incorporated thereinto and the subsequent mutagenesis. The mutation with sodium nitrite can be effected by the reaction using sodium nitrite in a concentration of 0.5 to 2 M, preferably 1 M, at a pH on the acidic side, preferably pH 4.3, at a temperature of 4° C. to 37° C., preferably 25° C., for a period of 1 minute to 5 hours, preferably 30 minutes. The mutation with formic acid can be effected by the reaction using 12 M formic acid at 4° C. to 37° C., preferably 15° C., for a period of 2 to 10 minutes. The mutation with hydrazine can be effected by the treatment using hydrazine in a concentration of 20% to 60% at 25° C. for 3 to 10 minutes. These mutant single-stranded DNAs are made into double-stranded forms using E. coli DNA polymerase Klenow fragment, Sequenase® and the like, followed by incorporation into a plasmid, which makes it possible to produce a mutant decarbamylase gene.

As the method for causing some random mutation using enzyme reaction, there can be employed a method using PCR (polymerase chain reaction) (D. W. Leung et al., A Journal of Methods in Cell and Molecular Biology, 1, 11–15 (1989)) or the like. This is a method in which TaqDNA polymerase is used for the synthesis of a gene from a synthetic DNA (DNA primer) having the sequences at both ends of the gene, at which time a mutant decarbamylase gene can be prepared by causing an error in the gene synthesis using TaqDNA polymerase under the reaction conditions such as higher concentrations of $MgCl_2$ and substrates (dNTPs) as compared with ordinary reaction or an extremely lowered concentration of only one substrate in four kinds of substrates.

As the method for introducing a mutation into a gene, which is specific to the site of a enzyme protein, there can be employed an in vitro method for introducing a site-specific mutation using an oligonucleotide, a method for replacing a cassette at the mutation site, a method using PCR or the like. The in vitro method for introducing a site-specific mutation using an oligonucleotide can be conducted by preparing a single-stranded DNA from a recombinant M13 phage having a decarbamylase gene incorporated thereinto, and making the DNA into a double-stranded form using a synthetic DNA primer containing a sequence, after the mutation, of a gene part to be allowed to cause some mutation and using an enzyme such as a DNA polymerase Klenow fragment, followed by introduction into E. coli. These reactions can readily be effected using a commercially available kit, for example, "Mutan™-K" or "Mutan™-G" available from Takara Shuzo, or "Oligonucleotide-directed in vitro mutagenesis System, version 2.0" from Amersham Japan. The method for replacing a cassette at the mutation site can be conducted by replacing the whole restriction enzyme fragment containing the site to be allowed to cause a mutation, with a synthetic DNA containing such a mutation. The method using a PCR reaction can be conducted according to the method of W. Ito, et al., Gene, 102, 67–70 (1991) or the like. In this method, PCR reaction is effected using a synthetic DNA primer containing the mutation and a synthetic DNA corresponding to the end of the gene, after which the resulting DNA fragment is allowed to hybridize with the full-length DNA of the gene, followed by another PCR reaction for the enzyme elongation of the fragment to its full length.

In the present invention, the mutant decarbamylase gene prepared in the above-described manner is ligated to a plasmid vector such as pUC19 or pKK-233-2, and the resulting recombinant vector is incorporated into *E. coli*, such as JM109, followed by colony formation on a plate containing an antibiotic and the like. Then, this colony is replicated onto a sterilized filter paper, and the plate is stored. The filter paper, after drying, is immersed in a solution containing lysozyme and Triton X-100 or repeatedly put in and out of an acetone-dry ice bath (freeze and thaw), thereby causing lysis. Then, this filter paper is immersed in a water bath thermostated at a temperature such as 65° C. or 70° C. for a constant period of time, for example, 5 minutes, and then dried, after which this filter paper is immersed in a reaction solution capable of making color development by decarbamylase activity. As the reaction solution, there can be used, for example, those which contains a carbamyl-D-amino acid as the substrate and also contains phenol, 4-aminoantipyrine, D-amino acid oxidase and peroxidase. The colony exhibiting color development can be separated as a thermostability-acquiring strain.

First, as an index indicating the thermostability of an enzyme, thermostable temperature is defined. The thermostable temperature is defined as the treatment temperature at which the activity of an enzyme is 50% inactivated by the thermal treatment for 10 minutes. As the source of a decarbamylase gene, microorganisms which are known to have a decarbamylase (e.g., microorganisms disclosed in the International Publication No. WO92/10579) can usually be used. The thermostable temperature is different with the respective decarbamylases of these microorganisms. To attain excellent stability tolerable to repeated use by an improvement in the thermostability, various properties other than thermostability should, of course, be taken into consideration, and it is desirable to use a decarbamylase exhibiting high thermostable temperature, for example, in the range of 60° to 63° C., from the first. From this point of view, a decarbamylase produced by Agrobacterium radiobacter KNK712 (FERM BP-1900) is preferred because of its relatively higher thermostable temperature of about 62° C. The decarbamylase from KNK712 and the DNA fragment coding for this enzyme have the amino acid sequence and the DNA sequence, respectively, shown in Sequence Listing, SEQ ID NOs: 2 & 1, respectively. The decarbamylase improved in thermostability obtained by the mutagenesis of this decarbamylase gene was found to contain a replacement of 57-histidine, 203-proline or 236-valine with a different amino acid, as shown in Sequence Listing, SEQ ID NOs: 3–32 respectively. Therefore, amino acids at at least three positions are related to the thermostability. High thermostability can be obtained not only by the replacement of one amino acid but also by the combined replacement of two or three amino acids. In the present invention, the thermostable temperature could be increased by at least 2° C., mostly about 5° C. or higher, and in some cases, by 10° C. or higher.

For example, it is possible to obtain a decarbamylase improved in thermostability by the substitution of leucine or tyrosine for 57-histidine; of leucine, asparagine, glutamic acid, threonine or serine for 203-proline; or of alanine, threonine or serine for 236-valine, as the different amino acid (Sequence Listing, SEQ ID NOs: 3–60 respectively). As the DNA sequences coding for these decarbamylases improved in thermostability, there were obtained those which contains a substitution of TAT, CTT or CTA for CAT, i.e., 401- to 403-nucleotides corresponding to 57-histidine; of TCT, CTT, GAA, AAC or ACC for CCT, i.e., 839- to 841-nucleotides corresponding to 203-proline; of GCG, GCT, ACC, ACG, TCA, TCG or AGT for GTG, i.e., 938- to 940-nucleotides corresponding to 236-valine (Sequence Listing, SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57 and 59, respectively). Once the thermostability-related amino acids are identified, the use of site-specific mutagenesis makes it possible to substitute many amino acids for these amino acids by the substitution of various bases. Thus, the DNA fragment coding for the decarbamylase improved in thermostability can be subjected to mutagenesis for a further improvement in the thermostability.

In case of Agrobacterium radiobacter KNK712 (FERM BP-1900), the derivative having two or three amino acid mutations in three amino acids which have been found to have a relation to the thermostability, i.e., 57-histidine, 203-proline and 236-valine (multiple mutant) is produced, for example, as follows.

In the gene structures of pAD108 (coding for a naturally occurring decarbamylase) and pAD402 (coding for a decarbamylase having Tyr substituted for 57-His), respectively, as shown in FIGS. 4 and 5, SphI and SalI are close to each other in the vicinity of the decarbamylase gene; therefore, an NdeI restriction site is formed at the initiation codon of the decarbamylase gene by the PCR method. Thus, 57-amino acid is present on the NdeI-SacI DNA fragment of about 190 bp; 203-amino acid on the SalI-ClaI DNA fragment of about 170 bp; and 236-amino acid on the ClaI-SphI DNA fragment of about 75 bp.

The multiple mutant is prepared by the replacement of these mutation-free DNA fragments with DNA fragments having some mutation in the thermostability-related amino acids. The DNA fragment having some amino acid mutation is prepared from the transformant or expression vector as obtained in Example 3 or 8.

On the other hand, an NdeI-EcoRI DNA fragment of about 1.6 kb containing a decarbamylase gene (which is naturally occurring or contains one amino acid mutation) is obtained by cleaving pAD108, pAD402 or the like, which has been conferred an NdeI restriction site, and then incorporated into an appropriate vector having NdeI and EcoRI restriction sites, such as pKK NE (prepared from pKK233-2 shown in FIG. 3) described in Example 9 and shown in FIG. 3, thereby obtaining a plasmid (e.g., pAD 1086 shown in FIG. 4 from pAD108; and pAD4021 shown in FIG. 5 from pAD402). The DNA fragments of this plasmid, which have no mutation site for the above-mentioned three amino acids, are replaced with DNA fragments containing such amino acid mutation sites, thereby obtaining an expression vector for multiple mutants.

In general, the multiple mutants thus prepared have improved thermostability in an additive manner depending upon the degree of thermostability improvement obtained by a single mutation. For the decarbamylase having two or more amino acid mutations in three kinds of amino acids, it is possible to select any combination of the substituted amino acids as described above.

The above-described method is not limited to the case of Agrobacterium sp. KNK712 (FERM BP-1900), and it can be used, in general, for a further improvement in the thermostability of a decarbamylase enzyme. That is, according to the method for making an enzyme thermostable as described above, several kinds of decarbamylases improved in thermostability can be obtained by the replacement of an amino acid, from which the thermostability-related amino acids are identified, and still another replacement of this amino acid makes it possible to find other amino acids giving an improvement in the thermostability. Under the circumstances that DNA fragments corresponding to the respective thermostable decarbamylases have already been obtained, simultaneous mutations can be introduced into plural amino acid sites related to the thermostability improvement by the operations in the following steps 1) to 5) (multiple mutant), which afforded a decarbamylase additively improved in thermostability.

1) Restriction enzymes are found out, each of which can yield a DNA fragment comprising a DNA portion coding for one of the thermostability-related amino acids by cleavage for the DNA fragment.

2) A DNA fragment comprising a DNA portion coding for one amino acid mutation site is obtained from the DNA fragments each coding for a thermostable decarbamylase having at least one amino acid mutation or from the vectors comprising the fragments with the corresponding restriction enzyme in step 1).

3) The corresponding DNA fragment but having no amino acid mutation is removed by cleaving a DNA fragment coding for a decarbamylase or a vector comprising the fragment with the same restriction enzyme as described above.

4) The mutation-containing DNA fragment obtained in step 2) is incorporated into the remaining DNA fragment after the cleavage for removing the corresponding DNA fragment in step 3) or into the vector comprising the remaining fragment.

5) The operations in steps 2) to 4) are repeated, if necessary.

According to this series of operations, it is possible to increase, by one or more, the number of mutations in the thermostability-related amino acids.

In case of Agrobacterium sp. KNK712 (FERM BP-1900), as the vector in step 2), any vector can be used so long as it has been prepared by giving an NdeI restriction site in an expression vector which is pUC19 having incorporated thereinto one of the DNA fragments shown in Sequence Listing, SEQ ID NOs: 3, 5, 7, 9, 11, 13, 15, 17, 19, 21, 23, 25, 27, 29, 31, 33, 35, 37, 39, 41, 43, 45, 47, 49, 51, 53, 55, 57 and 59, respectively. As the vector containing a decarbamylase gene in step 3), various vectors, including pAD4021 and pAD1086, can be used which are obtained using pKK NE in the same operations as for pAD4021 from the vector prepared by giving an NdeI restriction site in any vector selected from various examples of the expression vector as recited below, except for the vectors each containing a DNA fragment coding for a decarbamylase having already received an amino acid substitution for an improvement in the thermostability at every one of three thermostability-related sites (i.e., triple mutation-containing pAD426, pAD427, pAD454, pAD455 and pAD456). The DNA fragments obtained with restriction enzymes are NdeI-SacI, SalI-ClaI and ClaI-SphI in any case of step 2) or step 3).

The preparation of DNA fragments each coding for a decarbamylase, expression vectors obtainable by incorporating each of the DNA fragments into a vector, and transformants obtainable by incorporating each of the expression vectors into a host cell can be conducted using a gene manipulation technique as described in, for example, International Publication No. WO92/10579.

From the expression vector obtained by the incorporation of a DNA fragment shown in Sequence Listing, NOs: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65 and 67, respectively into pUC19 or pKK NE, for example, the incorporation into pUC19 gives pAD402, pAD404, pAD406, pAD416, pAD428, pAD429, pAD431, pAD434, pAD435, pAD439, pAD441, pAD445, pAD447, pAD448, pAD450, pAD451, pAD452, pAD453, pAD454 or pAD456; the incorporation into pKK NE gives pAD421, pAD422, pAD423, pAD424, pAD425, pAD426, pAD427, pAD461 and pAD455; and the incorporation into pUC NT (FIG. 10, upper part) gives pNT4553 (FIG. 10, lower part). The replacement of amino acids at the thermostability-related sites makes no change in the above-described restriction sites for restriction enzymes; therefore, the expression vector obtained by incorporation into pUC19 has the same restriction map as that of pAD429 (FIG. 6, upper part) and the expression vector obtained by incorporation into pKK NE has the same restriction map as that of pAD455 (FIG. 6, lower part). These expression vectors were used for the transformation of Escherichia coli JM109 or HB101, which afforded the following transformants capable of producing a decarbamylase improved in thermostability.

E. coli JM109 pAD402 (FERM BP-3912),
E. coli JM109 pAD404 (FERM BP-3913),
E. coli JM109 pAD406 (FERM BP-3914),
E. coli JM109 pAD416 (FERM BP-3915),
E. coli JM109 pAD428,
E. coli JM109 pAD429 (FERM BP-4035),
E. coli JM109 pAD431,
E. coli JM109 pAD434,
E. coli JM109 pAD435,
E. coli JM109 pAD439,
E. coli JM109 pAD441,
E. coli JM109 pAD445,
E. coli JM109 pAD447,
E. coli JM109 pAD448,
E. coli JM109 pAD450,
E. coli JM109 pAD421,
E. coli JM109 pAD422,
E. coli JM109 pAD423,
E. coli JM109 pAD424 (FERM BP-4034),
E. coli JM109 pAD425,
E. coli JM109 pAD426,
E. coli JM109 pAD427,
E. coli JM109 pAD451,
E. coli JM109 pAD452,
E. coli JM109 pAD453,
E. coli JM109 pAD461,
E. coli JM109 pAD454,
E. coli JM109 pAD455 (FERM BP-4036),
E. coli JM109 pAD456,
E. coli JM109 pAD468,
E. coli JM109 pAD469,
E. coli JM109 pAD470 or
E. coli HB101 pNT4553 (FERM BP-4368).

For these decarbamylases of the improved type, the amount of such an enzyme of interest produced by a transformant can be increased by incorporating the corresponding gene downstream the strong promotor of a vector.

The transformant can be cultured on a conventional nutrient medium to express a transformant DNA which has been introduced thereinto. In case where the transformant DNA has been conferred with certain properties originating in the genetic or vector DNA, the medium may be supplemented with various agents depending upon the properties.

The transformant thus produced can be obtained as an enzyme source only by culture preparation on a conventional medium; if necessary, various treatments may be employed for enzyme induction, such as the addition of hydantoin compounds, D-N-carbamoyl-α-amino acids, isopropyl-1-thio-β-D-galactoside (IPTG) or the like, and a temperature increase.

The medium to be used for the culture preparation of a transformant may usually be a conventional medium containing carbon sources, nitrogen sources and inorganic ions. If organic micronutrients such as vitamins and amino acids are added thereto, preferred results are often obtained. As the carbon sources, carbohydrates such as glucose and sucrose, organic acids such as acetic acid, alcohols and the like are suitably used. As the nitrogen sources, ammonia gas, ammonia water, ammonium salts and the like are used. As the inorganic salts, phosphate ion, magnesium ion, potassium ion, ferric ion and the like may be used.

The culture preparation may be conducted under aerobic conditions for 1 to 10 days while making an appropriate adjustment to the pH range of 4 to 8 and the temperature range of 25° to 45° C., which makes it possible to obtain desirable results. The enzyme produced by a transformant can be applied as a culture solution of the transformant, bacterial cells, treated bacterial cells, enzyme extracts from bacterial cells, immobilized bacterial cells or the like.

As the bacterial cells, there can be used any one of the forms such as an untreated culture solution after completion of the culture preparation, bacterial cells separated from the culture solution and washed bacterial cells. As the treated bacterial cells, there can be used lyophilized bacterial cells, acetone-dried bacterial cells, toluene- or surfactant-contacted bacterial cells, lysozyme-treated bacterial cells, ultrasonicated bacterial cells, mechanically-disrupted bacterial cells, enzyme extracts having an enzyme activity to convert D-N-carbamoyl-α-amino acids into the corresponding D-α-amino acids by removal of the carbamoyl groups, which have been obtained from these treated bacterial cells; immobilization products of these bacterial cells; insolubilization products of the treated bacterial cells; immobilization products of the treated bacterial cells on a support for the immobilization of an enzyme protein (e.g., anion exchange resin), or the like. For the method for immobilization, reference is made to the specification of the Japanese Patent Laid-open Publication No. 63-185382.

As the support to be used for immobilization, various anion exchange resins having various amine-, ammonium salt- or diethanolamine-type functional groups are suitable, such as phenol-formaldehyde anion exchange resins, for example, Duolite A568 and DS17186 (Rohm & Haas; registered trade names), and polystyrene resins, for example, Amberlite IRA935, IRA945, IRA901 (Rohm & Haas; registered trade names), Lewatatit OC1037 (Bayer; registered trade name) and Diaion EX-05 (Mitsubishi Chemical Inductries; registered trade name). In addition to these, any other support such as DEAE-cellulose can also be used.

Further, to ensure firm and stable adsorption of an enzyme, a crosslinking agent is usually used, and a preferred example thereof is glutaraldehyde. As the enzyme to be used, there can be applied, in addition to purified enzymes, those which have been purified to various degrees, such as partially-purified enzymes, solutions containing disrupted bacterial cells and cell-free extracts.

For the preparation of an immobilized enzyme, conventional methods can be used, which comprises, for example, allowing an enzyme to be adsorbed from an enzyme solution on a support and then subjecting the support to crosslinking treatment.

D-N-carbamoyl-α-amino acids used as the substrate of an enzyme reaction in the present invention can be expressed by the formula: R—CH(NHCONH$_2$)—COOH, and their forms to be subjected to the reaction in actual cases are as follows: in case where the enzyme to be used has strict stereoselectivity on the D-N-carbamoyl-α-amino acids, they can be used as the D-form or a mixture of the D- and L-forms; and in case where the enzyme has loose stereoselectivity because of its action even on L-carbamoylamino acids, or in case where it is used as an enzyme mixture capable of acting even on the L-amino acids, it is preferred that they are used only in the D-form for the production of a-amino acids in the D-form.

The substituent R can be selected within a wide range as described in the specifications of the Japanese Patent Publication Nos. 57-18793, 63-20520 and 1-48758. In particular, to provide useful compounds from an industrial point of view, such as intermediates for medicaments, it is preferred that R is phenyl, hydroxy-substituted phenyl, alkyl, substituted alkyl, aralkyl or thienyl. When R is hydroxy-substituted phenyl, it may be substituted with one or more hydroxy groups at the o-, m- and/or p-positions, and the typical example thereof is p-hydroxyphenyl. The term alkyl refers to a group of 1 to 4 carbon atoms, the corresponding amino acid of which is D-alanine, D-valine, D-leucine, D-isoleucine or the like. The term substituted alkyl refers to an alkyl group of 1 to 4 carbon atoms, which is substituted with hydroxy, alkylthio, carboxyl, amino, phenyl, hydroxy-substituted phenyl, amide or the like, the corresponding amino acid of which is D-serine, D-threonine, D-methionine, D-cysteine, D-asparagine, D-glutamine, D-tyrosine, D-tryptophan, D-aspartic acid, D-glutamic acid, D-histidine, D-lysine, D-arginine, D-citrulline or the like. The term aralkyl refers to a group of 7 to 8 carbon atoms, such as benzyl or phenetyl, the corresponding amino acid of which is D-phenylalanine or the like.

As the aqueous medium, there can be used water, buffer or those which contains an organic solvent such as ethanol. If necessary, various additives such as nutrients needed for the growth of microorganisms, antioxidants, surfactants, coenzymes, hydroxylamine and metals can also be added to the aqueous medium.

In case where the bacterial cells of the above-described microorganism are cultured in an aqueous medium, during which the bacterial cells are brought into contact with D-N-carbamoyl-α-amino acids for the reaction, D-N-carbamoyl-α-amino acids and nutrients needed for the growth of the microorganism, such as carbon sources, nitrogen sources and inorganic ions, are contained in the aqueous medium used. If organic micronutrients such as vitamins and amino acids are added thereto, preferred results are often obtained. As the nitrogen sources, carbohydrates such as glucose and sucrose, organic acids such as acetic acid, alcohols and the like are suitably used. As the nitrogen sources, ammonia gas, ammonia water, ammonium salts and the like are used. As the inorganic salts, phosphate ion, magnesium ion, potassium ion, ferric ion and the like may be used.

The culture preparation may be conducted under aerobic conditions for 1 to 10 days while making an appropriate adjustment to the pH range of 4 to 8 and the temperature range of 25° C. to 45° C., which makes it possible that D-N-carbamoyl-α-amino acids are converted only into D-α-amino acids with high efficiency.

In contrast, when the reaction of an untreated culture solution of the above-described microorganism, cultured bacterial cells, treated bacterial cells, enzyme extracts, immobilization products of bacterial cells, insolubilization products of bacterial cells or immobilization products of enzyme proteins is effected in an aqueous medium containing D-N-carbamoyl-α-amino acids dissolved or suspended therein, the reaction system may be allowed to stand or stirred for a time, while the temperature is adjusted to an appropriate range of 10° C. to 80° C. and the pH is kept in the range of 4 to 9.5. In this manner, after the lapse of 5 to 100 hours, D-α-amino acids are produced in great amounts and accumulated in the aqueous medium. The D-N-carbamoyl-α-amino acids may be added in separated portions according as the reaction proceeds. The D-α-amino acids produced can be separated and purified by a conventional separation method.

The D-α-amino acids obtained herein can be expressed by the formula:

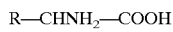

R—CHNH$_2$—COOH (wherein R is as defined above).

The following will describe the typical embodiments of the present invention. The detection and quantitative analysis of D-α-amino acids produced were conducted by high performance liquid chromatography (HPLC) or thin layer chromatography (TLC).

EXAMPLE 1
Mutagenesis of Agrabacterium sp. KNK712 Decarbamylase Gene with Hydroxylamine Plasmid pAD108 having a KNK712 decarbamylase gene was digested with restriction enzymes HindIII and EcoRI, which was mixed and ligated with the digest of an M13mp18 double-stranded DNA with HIndIII and EcoRI. This was transformed into E. coli JM109, which was mixed with 2 ml of H top agar medium (10 g/l bactotrypton, 8 g/l NaCl, 8 g/l bactoagar) containing 100 mM isopropyl-β-D-thiogalactopyranoside (IPTG) and 0.2% 5-bromo-4-chloro-3-indolyl-β-D-galactoside (X-Gal) added both in an amount of 40 μl, and then plated on an H agar plate (10 g/l bactotrypton, 8 g/l NaCl, 12 g/l bactoagar), followed by incubation at 37° C. and separation of a white plaque. This recombinant phage was cultured on 100 ml of 2YT medium (16 g/l bactotrypton, 10 g/l bactoyeast extract, 5 g/l NaCl), and a PEG-NaCl (20% polyethylene glycol 6000, 2.5 M NaCl) solution was added to the supernatant at a 1/5 volume, so that phage particles were precipitated and collected by centrifugation. These recombinant phage particles were treated in NH$_2$OH having a final concentration of 0.25 M (pH 6.0) at 37° C. for 1 to 8 hours. The phage particles were precipitated with a PEG-NaCl solution, and then dissolved in sterilized water, with which E. coli JM109 was infected. The microorganism was cultured on 800 ml of 2YT medium, and a double-stranded DNA having some mutation was prepared by the alkaline-SDS method and CsCl ultracentrifugation method. This was digested with HindIII and EcoRI, and then incorporated into pUC19, which was transformed into E. coli JM109, and then plated on a 2YT agar plate containing 50 μg/ml ampicillin. Thus, about 15,000 E. coli transformants each having a mutant decarbamylase gene were obtained.

EXAMPLE 2
Mutagenesis of Agrabacterium sp. KNK712 Decarbamylase Gene with Nitrous Acid The recombinant phage particles obtained by incorporating a KNK712 decarbamylase gene into M13mp18 as prepared in Example 1 were cultured on 800 ml of 2YT medium for preparation, and then subjected to phenol extraction and ethanol precipitation, which afforded a single-stranded phage DNA. This single-stranded DNA was treated with NaNO$_2$ having a final concentration of 0.9 M (pH 4.3) at 25° C. for 30 minutes, allowing a gene to cause some mutation. This was made into a double-stranded form by the use of Sequenase® ver. 2.0 (United States Biochemical) and AMV reverse transcriptase (Life Science). This was digested with restriction enzymes HindIII and EcoRI, and incorporated into pUC19, which was transformed into E. coli JM109 and then plated on a 2YT plate (containing ampicillin). Thus, about 7600 E. coli transformants each having a mutant decarbamylase gene were obtained.

EXAMPLE 3
Screening of Decarbamylase-producing Strain Improved in Thermostability The colony of the E. coli transformants each having a mutant decarbamylase gene on the plate were replicated onto a filter paper (Toyo Roshi, 5C, φ83 mm), which was soaked with 1.5 ml of lytic solution (20 mM Tris.HCl (pH 7.5), 10 mM EDTA, 2 mg/ml lysozyme, 1% Triton X-100), followed by a reaction at 37° C. for 30 minutes, washing with water and drying. This filter paper was immersed in hot water at 65° C. for thermal treatment, and after drying, it was soaked with 1 ml of color development reaction solution (30 mM K-phosphate buffer (pH 7.4), 0.3% carbamyl-D-phenylglycine, 0.25% phenol, 10 mg/ml D-amino acid oxidase (Sigma), 2.36 μg/ml peroxidase (derived from horseradish, CALZYME Lab.), 0.1 mg/ml 4-aminoantipyrine), followed by a reaction at 37° C. for 30 minutes. Colonies corresponding to the red-color developed spots were separated, as the strain improved in thermostability, from the original plate.

From 27,000 mutants as prepared by mutagenesis with hydroxylamine in Example 1 and 7600 mutans as prepared by mutagenesis with nitrous acid in Example 2, twelve and seven mutants improved in thermostability were obtained, respectively.

EXAMPLE 4
Thermostability Evaluation of Decarbamylase Improved in Thermostability A shaken culture containing one of four decarbamylaseproducing strains improved in thermostability as obtained in Example 3 (three mutants obtained by mutagenesis with hydroxylamine and one mutant obtained by mutagenesis with nitrous acid), together with recombinant E. coli JM109 pAD108 (FERM BP-3184) having a KNK712 decarbamylase gene, was prepared in 10 ml of 2YT liquid medium (containing 50 μg/ml ampicillin and 1 mM IPTG) and incubated overnight. After harvested, the bacterial cells were washed with 0.1 M K-phosphate buffer (pH 7.0), and suspended in 1 ml of the same buffer, after which the suspension was disrupted with an ultrasonic disrupting apparatus (Tomy Seiko, model UR-20P) and the residue was removed by centrifugation. One part of this crude enzyme solution was subjected to thermal treatment at a temperature such as 55° C., 60° C., 65° C., 70° C. and 75° C. for 10 minutes, and some denatured insolubilized protein was removed by centrifugation. Then, the decarbamylase activity before and after the thermal treatment were measured. In the measurement, using 1% carbamyl-D-hydroxyphenylglycine as the substrate, the reaction was effected in 0.1 M K-phosphate buffer (pH 7.0) at 40° C. for 20 minutes, followed by protein denaturation with 5% TCA and removal thereof, after which the amount of D- hydroxyphenylgliycine produced was determined by high performance liquid chromatography. The results are shown in FIG. 1.

EXAMPLE 5

Gene Analysis of Decarbamylase Improved in Thermostability

The gene analysis was conducted for the mutant decarbamylase improved in thermostability, to presume the mutation sites of the decarbamylase protein. The plasmid having a gene for the decarbamylase improved in thermostability was reacted in a programmable incubator (ASTEC, model PC-700) using Taq Dye Deoxy™ Terminator Cycle Sequencing Kit (Applied Biosystems), followed by removal of excess Dye Deoxy using Bio Spin 30 (BIO-RAD). This sample was subjected to electrophoresis and data analysis with DNA sequencer model 373A (Applied Biosystems). As the result, the mutation sites were found as shown in Table 1. In every cases, the thermostability was improved by one amino acid mutation.

TABLE 1

| Mutant | Thermostable temperature (° C.) | DNA mutation | Amino acid mutation |
| --- | --- | --- | --- |
| (712) Escherichia coli | 61.8 | none | none |
| JM109 pAD402 | 67.3 | 401 C → T | 57 His → Tyr |
| JM109 pAD404 | 68.0 | 840 C → T | 203 Pro → Leu |
| JM109 pAD406 | 66.5 | 839 C → T | 203 Pro → Ser |
| JM109 pAD416 | 71.4 | 939 T → C | 236 Val → Ala |

EXAMPLE 6

Immobilization of Decarbamylase Improved in Thermostability on Resin

A shaken culture containing one of four decarbamylase-producing strains improved in thermostability, together with recombinant E. coli JM109 pAD108 (FERM BP-3184) having a KNK712 decarbamylase gene, was prepared in 1 liter of 2YT medium (containing 50 μg/ml ampicillin and 1 mM IPTG) and incubated overnight. After harvested, the bacterial cells were washed with 0.1 M K-phosphate buffer (pH 7.0), and suspended in 100 ml of the same buffer, after which the suspension was disrupted with an ultrasonic disrupting apparatus (BRANSON, Sonifier model 250) and the residue was removed by centrifugation to yield a crude enzyme solution. To this, Duolite A-568 (Rohm & Haas) equilibrated with 0.1 M K-phosphate buffer (pH 7.0) was added at a ratio of 1 g resin to 40 mg protein, and the mixture was stirred under a nitrogen seal at 4° C. for 20 hours to ensure the adsorption. This enzyme-adsorbing resin was washed with 0.1 M K-phosphate buffer (pH 7.0) and 10 mM dithiothreitol (DTT), and reacted in 0.2% glutaraldehyde and 0.1 M K-phosphate buffer (pH 7.0) at 4° C. for 10 minutes for the protein crosslinking, which afforded an immobilized enzyme-containing resin. The activities of the resins thus obtained are shown in Table 2.

TABLE 2

| Mutant | E. coli JM109 pAD402 | E. coli JM109 pAD404 | E. coli JM109 pAD406 | E. coli JM109 pAD416 | 712 |
| --- | --- | --- | --- | --- | --- |
| Activity (u/g resin) | 12.4 | 9.4 | 10.0 | 14.6 | 9.6 |

EXAMPLE 7

Repeated Continuous Reaction Using Immobilized Decarbamylase

Figure 2:
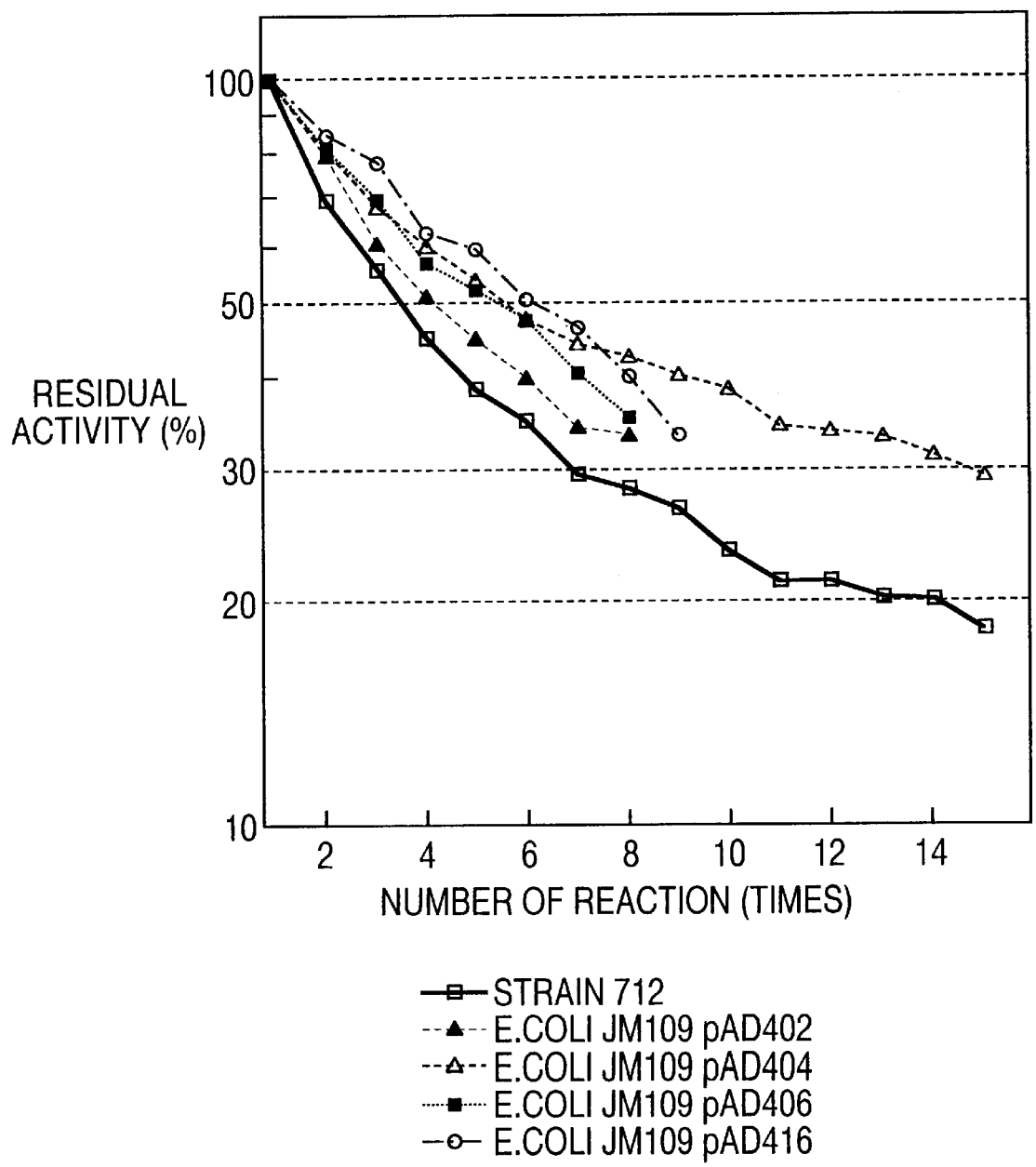
FIG. 2 is a graph showing the results of stability obtained by a repeated continuous test on the thermostability using a resin having immobilized thereon a decarbamylase improved in thermostability according to the present invention.

The mutant decarbamylase improved in thermostability was evaluated by the repeated continuous reaction using the immobilized enzyme-containing resin as obtained in Example 6. The reaction was effected (100 ml of reaction mixture) using 50 units of the immobilized decarbamylase and 3% carbamyl-D-HPG as the substrate at 40° C. with stirring under a stream of nitrogen gas while the pH was adjusted to 7.0. The sample was taken for the activity measurement after 10 and 60 minutes, and the reaction was continued for 23.5 hours in total. The reaction mixture was removed by suction, after which another fresh reaction mixture was charged and allowed to react in the same manner as described above; such an operation was repeated 15 times, and the change in the activity of the immobilized decarbamylase was examined. The results are shown in FIG. 2. All the decarbamylases improved in thermostability were found to have improved stabilities when used in the reaction as the immobilized enzyme-containing resin, as compared with those before the mutagenesis.

EXAMPLE 8

Amino Acid Replacement at Thermostability-related Sites

Various amino acids were substituted for three sites found to be related to thermostability, i.e., histidine which is 57-amino acid, proline which is 203-amino acid, and valine which is 236-amino acid, to prepare various derivatives. The preparation of these derivatives was conducted by the use of a method utilizing polymerase chain reaction (PCR) (W. Ito, et al., Gene, 102, 67–70 (1991)). For each of the thermostability-related sites, various synthetic primers were prepared with a mixed solution of A, T, G and C by the DNA synthesizer model 391 (Applied Biosystems), said primers having about 10-base sequence portions which were the same as the complimentary gene sequences on both sides of the gene portion corresponding to the amino acid at each site and also having any combination of A, T, G and C in the 3-base portion corresponding to the amino acid to be replaced, so that any kind of amino acid was incorporated into this 3-base portion after the replacement. With the use of pAD108 as the template, and using this primer and M13RV primer (Takara Shuzo), the PCR was effected by the programmable incubator model PC-700 (ASTEC). A DNA fragment containing the full-length decarbamylase gene fragment (1785 bases) and short-length sequences on both sides and having a mutation at every HindIII restriction sites so as not to be cleaved was prepared by the PCR reaction using pAD108 and MUTF3 and M13m4 primers (both, Takara Shuzo). These two kinds of PCR products were mixed together, and heated at 94° C. for 10 minutes, after which the mixture was gradually cooled for annealing, which afforded a combined form of these two kinds of DNAs. Using Taq DNA polymerase, single-stranded DNA portions were made into double-stranded forms. Using this DNA and M13M4 and M13RV primers, the PCR reaction was effected, and the DNA produced was simultaneously digested with HindIII and EcoRI. The digest was ligated with pUC19 which had been digested in the same manner as described above, and transformed into E. coli. According to the method as described in Example 3, only the strains improved in thermostability were screened, and it was found that derivatives having a substitution of leucine for 57-histidine, derivatives having a substitution of asparagine, glutamic acid, threonine, alanine, isoleucine or histidine for 203-proline, and derivatives having a substitution of threonine or serine for 236-valine had improved thermostability, as shown in Tables 3 and 4.

TABLE 3

| Mutant | Thermostable temperature (° C.) | DNA mutation | Amino acid mutation |
|---|---|---|---|
| (712) Escherichia coli | 61.8 | none | none |
| JM109 pAD434 | 67.5 | 402 A → T<br>403 T → A | 57 His → Leu |
| JM109 pAD435 | 67.0 | 402 A → T | 57 His → Leu |
| JM109 pAD431 | 67.0 | 839 C → A<br>840 C → A<br>841 T → C | 203 Pro → Asn |
| JM109 pAD429 | 70.0 | 839 C → G<br>840 C → A<br>841 T → A | 203 Pro → Glu |
| JM109 pAD445 | 67.5 | 839 C → A<br>841 T → C | 203 Pro → Thr |
| JM109 pAD468 | 67.7 | 839 C → G | 203 Pro → Ala |
| JM109 pAD469 | 67.2 | 839 C → A<br>840 C → T | 203 Pro → Ile |
| JM109 pAD470 | 65.2 | 840 C → A | 205 Pro → His |

TABLE 4

| Mutant | Thermostable temperature (° C.) | DNA mutation | Amino acid mutation |
|---|---|---|---|
| (712) Escherichia coli | 61.8 | none | none |
| JM109 pAD428 | 70.0 | 939 T → C<br>940 G → C | 236 Val → Ala |
| JM109 pAD439 | 71.5 | 939 T → C<br>940 G → T | 236 Val → Ala |
| JM109 pAD441 | 71.5 | 938 G → A<br>939 T → G<br>940 G → T | 236 Val → Ser |
| JM109 pAD447 | 72.0 | 938 G → T<br>939 T → C<br>940 G → A | 236 Val → Ser |
| JM109 pAD448 | 72.0 | 938 G → T<br>939 T → C | 236 Val → Ser |
| JM109 pAD450 | 69.5 | 938 G → A<br>939 C → C | 236 Val → Thr |

EXAMPLE 9
Multiple Mutation at Thermostability-related Site

Derivatives (multiple mutants) having a combination of two or three amino acid mutations which had been found to improve the thermostability, at three sites which had been found to be related to the thermostability, i.e., histidine which is 57-amino acid, proline which is 203-amino acid, and valine which is 236-amino acid, were prepared as follows.

The multiple mutants were prepared by replacing the mutation-free DNA fragments of a native gene with the restriction enzyme-digested DNA fragments each containing some mutation site of a mutant decarbamylase gene which had been improved in thermostability by a single amino acid substitution, as obtained in Example 3 or 8. First, because pAD108, pAD402 and other plasmids, which had the same restriction sites, each have two SalI and two SphI restriction sites for use in the replacement of the above-described DNA fragments, it is necessary to make these sites into a single restriction site. Therefore, as a new vector for gene incorporation, pKK NE was prepared, into which a decarbamylase gene fragment was incorporated, thereby constructing an expression vector to be used for the DNA fragment replacement.

Plasmid pKK NE was prepared as follows. Plasmid pKK233-2 (Pharmacia) shown in FIG. 3 was digested with EcoRI and NdeI, and subjected to agarose gel electrophoresis to separate a 2.7-kb DNA fragment, after which the cohesive end of the DNA fragment was changed to the blunt end with a DNA blunting kit (Takara Shuzo), followed by ligation and transformation into E. coli JM109.

The NcoI restriction site of the vector thus prepared was changed to the NdeI restriction site using the PCR method. The resulting plasmid was digested with HindIII, and the cohesive end thereof was changed to the blunt end, followed by ligation with pEcoRI linker (Takara Shuzo), which afforded pKK NE as shown in FIG. 3. Next,.into the initiation codon portion of the decarbamylase gene in plasmid pAD108 or pAD402, the NdeI restriction site was generated by the PCR method. The resulting NdeI-EcoRI DNA fragment of 1.6 kb was then incorporated into pKK NE, which afforded expression vectors pAD1086 (derived from pAD108; shown in FIG. 4) and pAD4021 (derived from pAD402; shown in FIG. 5).

The 57-amino acid mutation is positioned on the NdeI-SacI DNA fragment of about 190 bp; the 203-amino acid mutation on the SalI-ClaI DNA fragment of about 170 bp (this DNA fragment is hereinafter referred to as fragment A); and the 236-amino acid mutation on the ClaI-SphI DNA fragment of about 75 bp (hereinafter referred to as fragment B). Therefore, fragment A of pAD4021 was removed, into which site the same fragment of pAD404 or pAD406 was incorporated, resulting in pAD421 or pAD422, respectively. Also, fragment B of pAD1086, pAD4021, pAD421 or pAD422 was replaced with the same fragment of pAD416, resulting in pAD4161, pAD423, pAD426 or pAD427, respectively. Further, fragment A of pAD4161 was replaced with the same fragment of pAD404, pAD406 or pAD429, resulting in pAD424, pAD425 or pAD461, respectively; fragment A of pAD402 or pAD423 was replaced with the same fragment of pAD429, resulting in pAD451 or pAD455 (shown in FIG. 6), respectively; fragment B of pAD402, pAD429 (shown in FIG. 6), pAD451 or pAD421 was replaced with the same fragment of pAD447, resulting in pAD452, pAD453, pAD454 or pAD456, respectively.

The expression vectors prepared in the above-described manner were separately transformed into E. coli JM109, from which the extracts of disrupted bacterial cells were prepared and examined for the thermostability.

As shown in Tables 5 and 6, for the multiple mutants, it was found that the thermostability was additively improved according to the degree of an improvement in the thermostability attained by a single mutation. For the decarbamylase produced by E. coli JM109 pAD455 (FERM PB-4036) having highest thermostability, it was found that the thermostability was improved even by about 19° C., as compared with the decarbamylase before the mutagenesis.

TABLE 5

| Mutant | Amino acid mutation | Thermostable temperature (° C.) |
|---|---|---|
| (712) Escherichia coli | none | 61.8 |
| JM109 pAD421 | 57 His → Tyr<br>203 Pro → Leu | 71.5 |
| JM109 pAD422 | 57 His → Tyr | 70.0 |

TABLE 5-continued

| Mutant | Amino acid mutation | Thermostable temperature (° C.) |
|---|---|---|
| JM109 pAD423 | 203 Pro → Ser<br>57 His → Tyr<br>236 Val → Ala | 75.4 |
| JM109 pAD424 | 203 Pro → Leu<br>236 Val → Ala | 77.5 |
| JM109 pAD425 | 203 Pro → Ser<br>236 Val → Ala | 75.9 |
| JM109 pAD426 | 57 His → Tyr<br>203 Pro → Leu<br>236 Val → Ala | 78.8 |
| JM109 pAD427 | 57 His → Tyr<br>203 Pro → Ser<br>236 Val → Ala | 77.8 |

TABLE 6

| Mutant | Amino acid mutation | Thermostable temperature (° C.) |
|---|---|---|
| (712) Escherichia coli | none | 61.8 |
| JM109 pAD451 | 57 His → Tyr<br>203 Pro → Glu | 74.0 |
| JM109 pAD452 | 57 His → Tyr<br>236 Val → Ser | 75.3 |
| JM109 pAD453 | 203 Pro → Glu<br>236 Val → Ser | 76.0 |
| JM109 pAD461 | 203 Pro → Glu<br>236 Val → Ala | 79.0 |
| JM109 pAD454 | 57 His → Tyr<br>203 Pro → Glu<br>236 Val → Ser | 80.4 |
| JM109 pAD455 | 57 His → Tyr<br>203 Pro → Glu<br>236 Val → Ala | 80.8 |
| JM109 pAD456 | 57 His → Tyr<br>203 Pro → Leu<br>236 Val → Ser | 78.5 |

EXAMPLE 10

Figure 7:
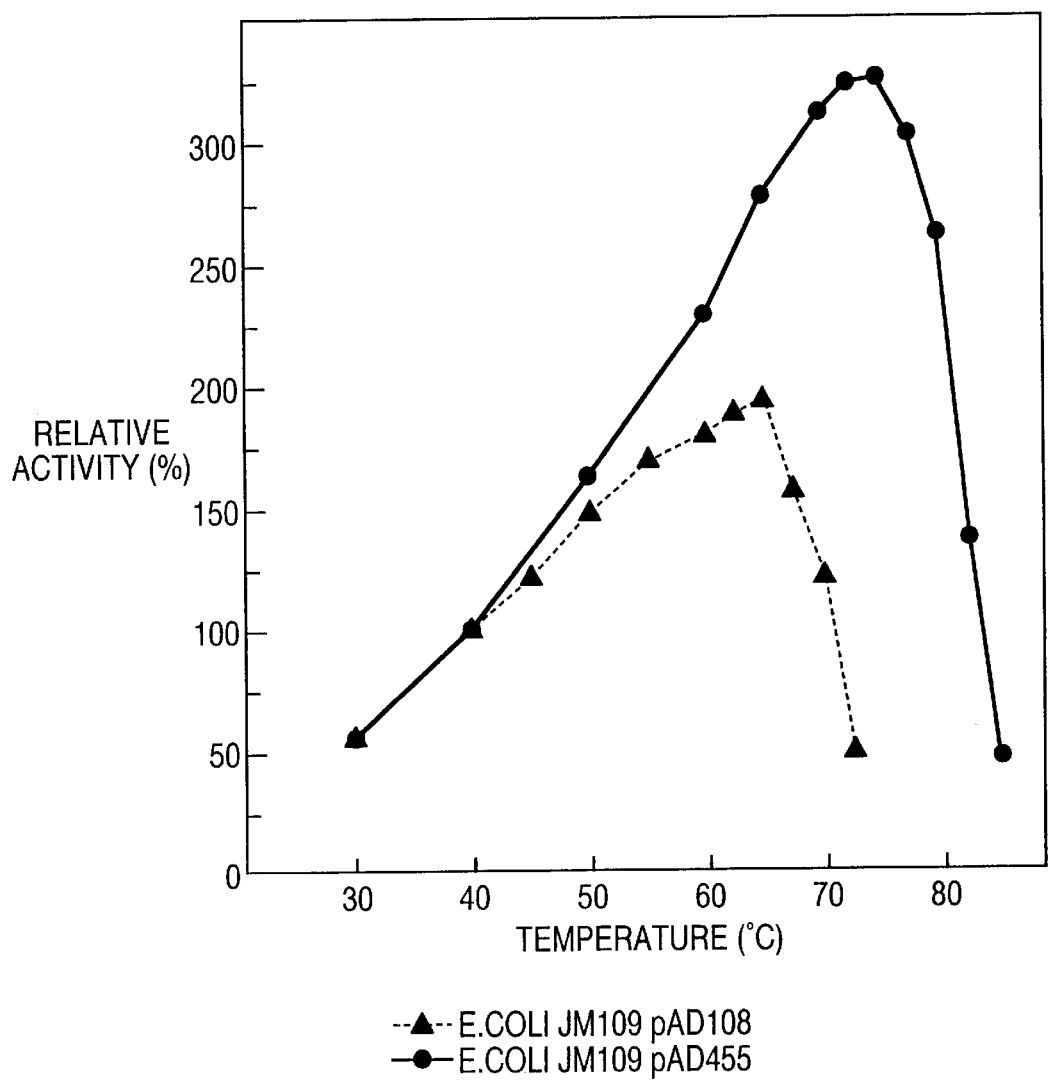
FIG. 7 is a graph showing the relationship between the reaction temperature of a decarbamylase produced by E. coli JM109 pAD108 or E. coli JM109 pAD455 and its activity.

Reaction Temperature Characteristics of Decarbamylase Improved in Thermostability A shaken culture containing a thermostability-improved decarbamylase-producing strain, E coli JM109 pAD108 (FERM BP-3184) or E. coli JM109 pAD455 (FERM BP-4036), was prepared in 10 ml of 2YT medium and incubated overnight. After harvested, the bacterial cells were washed with 0.1 M K-phosphate buffer (pH 7.0), and then suspended in 1 ml of the same buffer, after which the suspension was disrupted with an ultrasonic disrupting apparatus (Tomy Seiko, model UR-20P) and the residue was removed by centrifugation to yield a clude enzyme solution. This crude enzyme solution was 10-fold diluted with a solution obtained by the addition of 5 mM dithiothreitol to the same buffer. Several 1 ml substrate solutions (1% carbamyl-D-p-hydroxyphenylglycine, 0.1% K-phosphate buffer (pH 6.5)) were kept at various temperatures of 30° C. to 85° C. for 3 minutes, respectively, to which 100 µl of the diluted crude enzyme solution (or when the temperature was in the range of 50° C. to 80° C. for higher thermostability (the temperature was in the range of 50° C. to 65° C. for the crude enzyme solution of E. coli JM109 pAD108), 100 µl of the enzyme solution which had been further 2- to 3-fold diluted) was added, followed by a reaction at the respective temperatures for 20 minutes. Then, the reaction was allowed to stop by adding 250 µl of 20% trichloroacetic acid solution, followed by centrifugation, after which the supernatant was analyzed by high performance liquid chromatography (Nakalai tesque, Cosmosil 5C18-AR column). Taking the activity at 40° C. as 100%, the relative activity at each temperature is shown in FIG. 7. As can be seen from FIG. 7, the enzyme produced by E. coli JM109 pAD455 exhibits the highest activity at a temperature around 75° C. and has extremely improved stability, indicating that it was improved into an enzyme capable of acting at higher temperatures, as compared with the enzyme produced by E. coli JM109 pAD108.

EXAMPLE 11 pH Stability of Decarbamylase Improved in Thermostability

Figure 8:
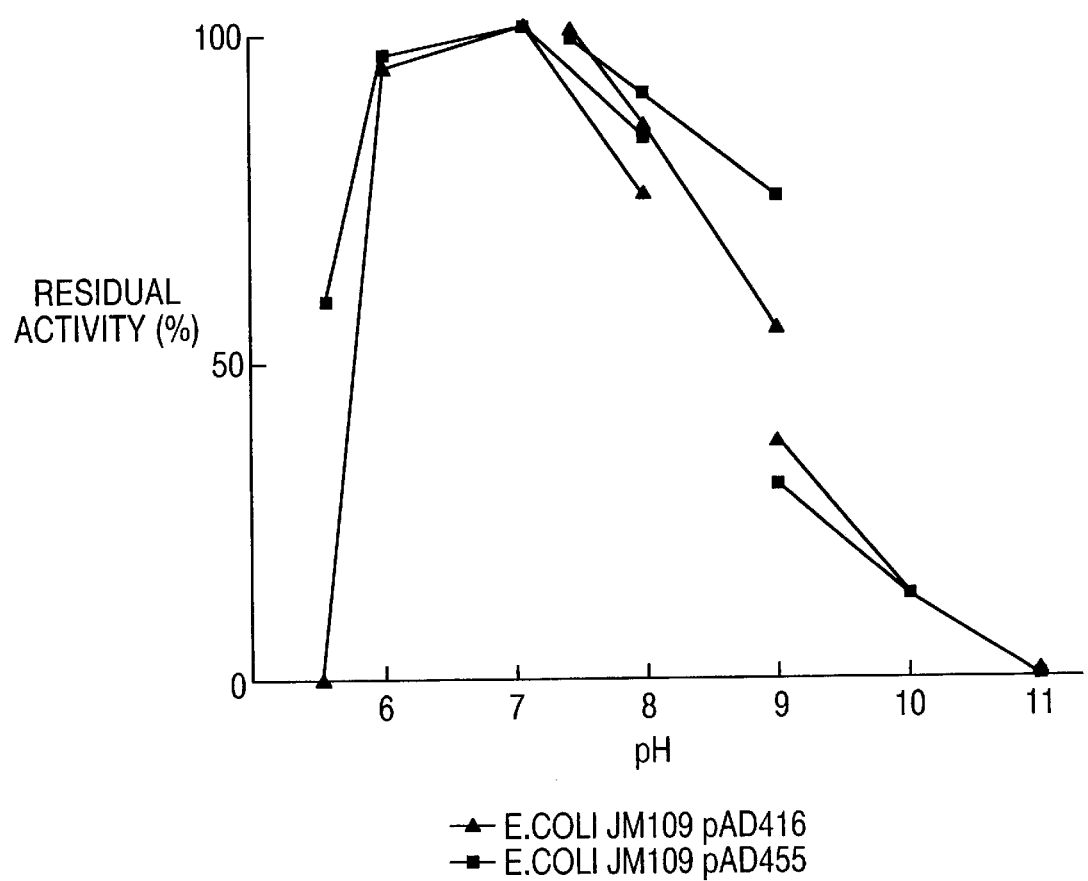
FIG. 8 is a graph showing the stability against pH, of a decarbamylase produced by E. coli JM109 pAD416 or E. coli JM109 pAD455.

A shaken culture containing a thermostability-improved decarbamylase-producing strain, E. coli JM109 pAD416 (FERM BP-3915) or E. coli JM109 pAD455 (FERM BP-4036), was prepared in 10 ml of 2YT medium and incubated overnight. After harvested, the bacterial cells were washed with 10 mM K-phosphate buffer (pH 7.0; containing 0.5 mM dithiothreitol), and suspended in 1 ml of the same buffer, after which the suspension was disrupted with a small-sized ultrasonic disrupting apparatus and the residue was removed by centrifugation to yield a clude enzyme solution. Various buffers for the respective pHs were prepared from 0.1 M K-phosphate buffer (pH 5.5, 6, 7, 8), Tris-HCl buffer (pH 7.5, 8, 9) and sodium carbonate buffer (pH 9, 10, 11). To 800 µl of each of these buffers, 200 ll of the crude enzyme solution was added, and the mixture was incubated at 40° C. for 12.5 hours. Then, 100 µl of the mixture was added to 1 ml of substrate solution (1% carbamyl-D-p-hydroxyphenylglycine, 0.1% K-phosphate buffer (pH 7.0)), followed by a reaction at 40° C., after which the reaction mixture was analyzed in the same manner as described in Example 10. Taking the activity at pH 7.0 as 100%, the relative activity of the treated sample at each pH is shown in FIG. 8.

EXAMPLE 12

Figure 9:
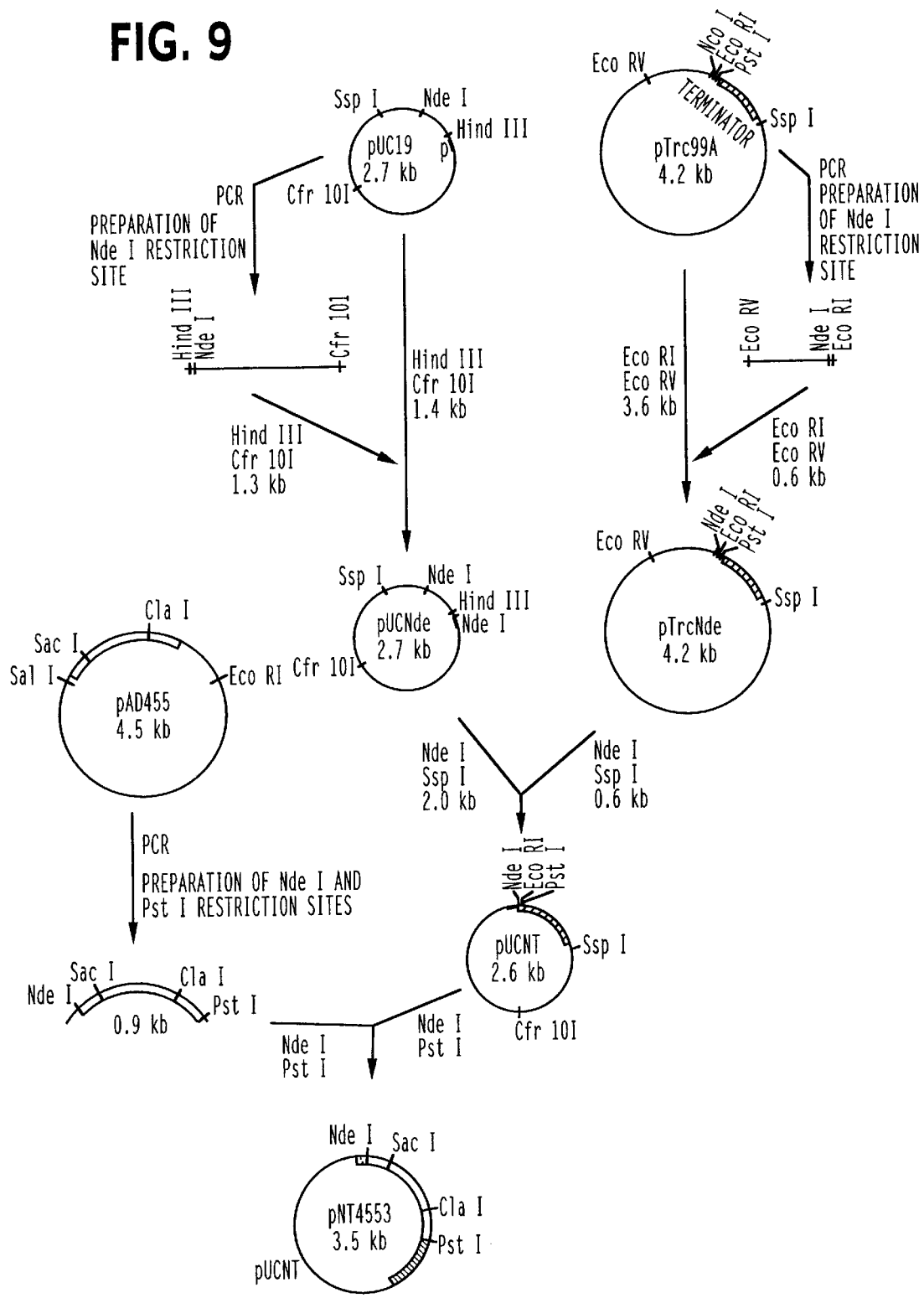
FIG. 9 shows a process for preparing vector pUC NT for the introduction of a foreign gene and vector pNT4553 for the expression of a decarbamylase improved in thermostability.

Preparation and Expression of Expression Vector for Decarbamylase Improved in Thermostability (1) Preparation ot Vector for Expression of Foreign Gene First, a vector was prepared for the incorporation of a thermostability-improved decarbamylase gene and expression thereof (FIG. 9). From pUC19, HindIII-Cfr10I fragment of 1.3 kb was prepared by the PCR method, at which time as the PCR primer, a primer having a sequence designed so that an NdeI restriction site was formed at the initiation codon site of a lacZ gene inside the HindIII restriction site and the sequence could be further digested with HindIII and Cfr10I, was used for the reaction. This DNA fragment obtained by the PCR was digested with HindIII and Cfr10I, followed by ligation with 1.4-kb fragment obtained by removal of the corresponding 1.3-kb fragment from pUC19, resulting in plasmid pUC·Nde which corresponds pUC19 having an NdeI restriction site added thereto. Next, from pTrc99A (commercially available from Pharmacia), an EcoRI-EcoRV fragment of 0.6 kb was prepared by the PCR method, at which time as the PCR primer, a primer having a sequence designed so that an NdeI restriction site was substituted for the NcoI restriction site inside the EcoRI restriction site and the sequence could be further digested with EcoRI and EcoRV, was used for the reaction. This DNA fragment obtained by the PCR was digested with EcoRI and EcoRV, followed by ligation with 3.6-kb fragment obtained by removal of the corresponding 0.6-kb fragment from pTrc99A, resulting in plasmid pTrcNde which corresponds pTrc99A having an NdeI restriction site added thereto. Then, a 2.0-kb fragment obtained by the digestion of pUC Nde with NdeI and SspI was ligated with a 0.6-kb fragment obtained by the digestion of pTrc Nde with NdeI and SspI, which afforded expression vector plasmid PUCNT for the expression of foreign genes (FIG. 10).

(2) Incorporation of Thermostability-Improved Decarbamylase Gene Into Vector

From pAD455 having a gene for one kind of decarbamylases improved in thermostability, only the gene portion coding for the decarbamylase was prepared by the PCR method, at which time as the PCR primer, a primer having a sequence designed so that an NdeI restriction site was formed in the initiation codon portion of the gene and a PstI restriction site was made just after the termination codon of the gene, was used for the reaction. A 0.9-kb DNA fragment obtained by this PCR was digested with NdeI and PstI, followed by ligation with pUCNT which was also digested with NdeI and PstI, which afforded expression vector plasmid pNT4553 (FIG. 10) for the decarbamylase improved in thermostability.

(3) Expression of Thermostability-Improved Decarbamylase Expression Vector the pNT4553 as prepared above was transformed into *Escherichia coli* HB101 by the calcium chloride method. A shaken culture of this transformant *E. coli* HB101 pNT4553 (FERM BP-4368) was prepared on a 2YT medium and incubated at 37° C. for 16 hours. After the bacterial cells were harvested, a crude enzyme solution was prepared by the method as shown in (Example 10), and the decarmylase activity was measured to be 5.6 unites/ml per culture solution.

According to the present invention, DNA fragments each coding for a decarbamylase protein improved in thermostability can be obtained, from which a decarbamylase having high reactivity to D-N-carbamoyl-α-amino acids and excellent stability can be produced, and with the use of this enzyme, D-α-amino acids can be produced with high efficiency.

We claim:

1. A method for producing a decarbamylase, which has an amino acid sequence as shown in SEQ. ID No. 2 except that at least one amino acid selected from 57-histidine, 203-proline and 236-valine of SEQ. ID No. 2 is replaced by a different amino acid to provide the decarbamylase with a thermostable temperature of which is in a range of 65° C. to about 80° C., comprising:

1) obtaining a DNA fragment coding for a decarbamylase which has the amino acid sequence shown in SEQ. ID No. 2 and whose thermostable temperature is below 63° C., from a microorganism capable of producing said decarbamylase, 2) introducing said DNA fragment of step 1) into an appropriate vector, 3) subjecting said DNA fragment contained in the vector to mutagenesis, 4) introducing said mutated DNA fragment of step 3) into a second vector, 5) transforming a host cell with the resultant second vector, 6) selecting a transformant which can produce the decarbamylase, the thermostable temperature of which is in a range of 65° C. to about 80° C., 7) optionally subjecting the DNA fragment coding for a decarbamylase obtained from said selected transformant to the operations of steps 1) to 6) to obtain a second transformant which can produce a decarbamylase having a higher thermostable temperature than that of the decarbamylase of the transformant of step 6), 8) obtaining the DNA fragment encoding a decarbamylase derived from said transformant obtained in step 6) and/or 7), 9) locating amino acids corresponding to mutation sites coded in said DNA fragment of step 8) by subjecting the DNA fragment to gene analysis, 10) replacing a DNA codon coding said amino acid corresponding to said mutation site with a DNA codon coding another amino acid, 11) introducing the DNA fragment containing said DNA codon of step 10) into a third vector, 12) transforming a host cell with the third vector of step 11) to obtain a transformant, and 13) cultivating said transformant of step 12).

2. A preparation process according to claim 1, wherein said mutagenesis is performed while said DNA fragment is single stranded.

3. A preparation process according to claim 2, wherein the DNA fragment coding for a microorganism-derived decarbamylase is incorporated into a phage and subjected to mutagenesis in the form of a single strand.

4. A preparation process according to claim 2 wherein the single-stranded DNA fragment is a DNA strand containing the codons corresponding to the amino acid sequence of the decarbamylase.

5. A preparation process according to claim 2, wherein the single-stranded DNA fragment is the complementary strand of the DNA strand containing the codons corresponding to the amino acid sequence of the decarbamylase.

6. A preparation process according to claim 1, wherein the mutagenesis causes mutations at random sites.

7. A preparation process according to claim 6, wherein the mutagenesis is chemical mutagenesis.

8. A preparation process according to claim 7, wherein the mutagenesis is effected with hydroxylamine.

9. A preparation process according to claim 7, wherein the mutagenesis is effected with nitrous acid.

10. A preparation process according to claim 1, wherein the mutagenesis is site-specific mutagenesis at mutation sites.

11. A preparation process according to claim 10, wherein polymerase chain reaction (PCR) is used in the site-specific mutagenesis.

12. A production process according to claim 1, wherein said DNA fragment coding for a decarbamylase having the amino acid sequence shown in SEQ. ID No. 2 is obtained from Agrobacterium sp. KNK712 (FERM BP-1900).

13. A production process according to claim 1, wherein another amino acid is tyrosine or leucine for 57-histidine, leucine, serine, asparagine, glutamic acid, alanine, isoleucine, histidine or threonine for 203-proline, and alanine, threonine or serine for 236-valine.

14. A production process according to claim 1, wherein the transformant microorganism is *Escherichia coli* (*E. coli*) JM109 pAD402 (FERM BP-3912), *E. coli* JM 109 pAD404 (FERM BP-3913), *E. coli* JM109 pAD406 (FERM BP-3914), *E. coli* JM109 pAD416 (FERM BP 3915), *E. coli* JM109 pAD428, *E. coli*, JM109 pAD429 (FERM BP-4035), *E. coli* JM109 pAD431, *E. Coli* JM109 pAD434, *E. coli* JM109 pAD435, *E. coli* JM109 pAD439, *E. coli* JM109 pAD441, *E. coli* JM109 pAD445, *E. coli* JM109 pAD447, *E. coli* JM109 pAD448, *E. coli* JM109 pAD450, *E. coli* JM109 pAD421, *E. coli* JM109 pAD422, *E. coli* JM109 pAD423, *E. coli* JM109 pAD424 (FERM BP-4034), *E. coli* JM109 pAD425, *E. coli* JM109 pAD426, *E. coli* JM109 pAD427, *E. coli* JM109 pAD451, *E. coli* JM109 pAD452, *E. coli* JM109 pAD453, *E. coli* JM109 pAD461, *E. coli* JM109 pAD454, *E. coli* JM109 pAD455 (FERM BP-4036), *E. coli* JM109 pAD456, *E. coli* JM109 pAD468, *E. coli* JM109 pAD469, *E. coli* MJ109 pAD470 or *E. coli* HB101 pNT4553 (FERM BP-4368).

15. A preparation process according to claim 1, wherein the thermostable temperature is in a range of 65° C. to 80.8° C.

16. A decarbamylase characterized in that said decarbamylase has an amino acid sequence as shown in SEQ. ID No. 2 except that at least one amino acid is replaced by a different amino acid and that at least one replacement must occur at position 57-histidine, 203-proline or 236-valine to provide the decarbamylase with a thermostable temperature in a range of 65° C. to about 80° C., said decarbamylase being an enzyme converting an N-carbamyl-D-α-amino acid, by removing its carbamyl group, into the corresponding D-amino acid.

17. The decarbamylase according to claim 16, wherein said decarbamylase having an amino acid sequence as shown in SEQ. ID. No. 2 is produced by Agrobacterium sp. KNK712 (FERM BP- 1900).

18. A decarbamylase according to claim 16, wherein at least 57-histidine is replaced with another amino acid.

19. A decarbamylase according to claim 18, wherein another amino acid is tyrosine or leucine.

20. A decarbamylase according to claim 16, wherein at least 203-proline is replaced with another amino acid.

21. A decarbamylase according to claim 20, wherein another amino acid is leucine, glutamic acid, serine, asparagine, threonine, alanine, isoleucine or histidine.

22. A decarbamylase according to claim 16, wherein at least 236-valine is replaced with another amino acid.

23. A decarbamylase according to claim 22, wherein another amino acid is alanine, threonine or serine.

24. A decarbamylase according to claim 16, wherein the thermostable temperature is in a range of 65° C. to 80.8° C.

25. A DNA fragment encoding the decarbamylase of claim 16, wherein at least one of the bases encoding histidine at position 57, proline at position 203 or valine at position 236 of a DNA fragment encoding SEQ. ID No. 1 is altered to encode another amino acid.

26. The DNA fragment according to claim 25, wherein said DNA fragment encoding SEQ. ID No. 1 is obtained from Agrobacterium sp. KNK712 (FERM BP-1900).

27. A DNA fragment according to claim 25, in which at least one of cytosine, adenine and thymine (CAT) of a base sequence coding for histidine at position 57 is altered to encode tyrosine or leucine.

28. A DNA fragment according to claim 27, wherein the base sequence CAT of claim 27 is replaced with TAT, CTT or CTA.

29. A DNA fragment according to claim 25, in which at least one of cytosine, cytosine and thymine (CCT) of a base sequence coding for proline at position 203 is altered to encode serine, leucine, asparagine, glutamic acid, threonine, alanine, isoleucine or histidine.

30. A DNA fragment according to claim 29, wherein the base sequence CCT of claim 29 is replaced with TCT, CTT, AAC, GAA, ACC, GCT, ATT, or CAT.

31. A DNA fragment according to claim 25, in which at least one of guanine, thymine and guanine (GTG) of a base sequence coding for valine at position 236 is altered to encode alanine, serine or threonine.

32. A DNA fragment according to claim 31, wherein the base sequence GTG of claim 31 is replaced with GCG, GCT, ACC, ACG, TCA, TCG or AGT.

33. The DNA fragment according to claim 25, wherein the DNA fragment comprises a base sequence composed of base nos. 233 to 1141 of a DNA fragment as shown in Sequence Listing, SEQ. ID Nos. 3, 5, 7, 9, 11, 13, 15, 17, 19, 21, 23, 25, 27, 29, 31, 47, 49, 51, 55 and 65, and a base sequence composed of base nos. 7 to 915 of a DNA fragment as shown in Sequence Listing, SEQ. ID Nos. 33, 35, 37, 39, 41, 43, 45, 53, 57 and 67.

34. An expression vector comprising the DNA fragment of claim 25 and a plasmid vector.

35. A microorganism transformed with the expression vector of claim 34.

36. A DNA fragment according to claim 25, wherein the thermostable temperature is in a range of 65° C. to 80.8° C.

37. A process for producing a D-α-amino acid, characterized in that an N-carbamyl-D-α-amino acid is converted into the corresponding D-α-amino acid in an aqueous medium by the action of the decarbamylase of claim 16.

38. A production process according to claim 37, wherein the decarbamylase is allowed to act in an immobilized form.

39. A production process according to claim 38, wherein the immobilized decarbamylase is repeatedly used.

40. A production process according to claim 37, wherein said decarbamylase having an amino acid sequence as shown in SEQ. ID No. 2 is produced by Agrobacterium sp. KNK712 (FERM BP-1900).

41. A production process according to claim 37, wherein another amino acid is tyrosine or leucine for 57-histidine, leucine, serine, asparagine, glutamic acid, alanine, isoleucine, histidine or threonine for 203-proline, and alanine, threonine or serine for 236-valine.

42. A production process according to claim 37, wherein said decarbamylase whose thermostable temperature is in a range of 65° to about 80° C., is a decarbamylase which is produced by a transformant microorganism, *E. coli* JM109 pAD402 (FERM BP-3912), *E. coli* JM109 pAD404 (FERM BP-3913), *E. coli* JM109 pAD406 (FERM BP-3914), *E. coli* 314109 pAD416 (FERM BP-3915), *E. coli* JM109 pAD428, *E. coli* JM109 pAD429 (FERM BP-4035), *E. coli* JM109 pAD431, *E. coli* JM109 pAD434, *E. coli* JM109 pAD435, *E. coli* JM109 pAD439, *E. coli* JM109 pAD441 E, coli JM109 pAD445, *E. coli* JM109 pAD447, *E. coli* JM109 pAD448, *E. coli* JM109 pAD450, *E. coli* JM109 pAD421, *E. coli* JM109 pAD422, *E. coli* JM109 pAD423, *E. coli* JM109 pAD424, (FERM BP-4034), *E. coli* JM109 pAD425, *E. coli* JM109 pAD426, *E. coli* JM109 pAD427, *E. coli* JM109 pAD451, *E. coli* JM109 pAD452, *E. coli* JM109 pAD453, *E. coli* JM109 pAD461, *E. coli* JM109 pAD454, *E. coli* JM109 pAD455, (FERM BP-4036), *E. coli* JM109 pAD456, *E. coli* JM109 pAD468, *E. coli* JM109 pAD469, *E. coli* JM109 pAD470 or *E. coli* HB101 pNT4553 (FERM BP-4368).

43. A process according to claim 37, wherein the thermostable temperature is in a range of 65° C. to 80.8° C.

44. An expression vector which is pAD402, pAD404, pAD406, pAD416, pAD428, pAD429, pAD431, pAD434, pAD435, pAD439, pAD441, pAD445, pAD447, pAD448, pAD450, pAD421, pAD422, pAD423, pAD424, pAD425, pAD426, pAD427, pAD451, pAD452, pAD453, pAD461, pAD454, pAD455, pAD456, pAD468, pAD469, pAD470 or PNT4553.

45. A transformant microorganism which is *E. coli* JM109 pAD402 (FERM BP-3912), *E. coli* JM109 pAD404 (FERM BP-3913), *E. coli* JM109 pAD406 (FERM BP-3914), *E. coli* JM109 pAD416 (FERM BP-3915), *E. coli* JM109 pAD428, *E. coli* JM109 pAD429, (FERM BP-4035), *E. coli* JM109 pAD431, *E. coli* JM109 pAD434, *E. coli* JM109 pAD435, *E. coli* JM109 pAD439, *E. coli* JM109 pAD441, *E. coli* JM109 pAD445, *E. coli* JM109 pAD447, *E. coli* JM109 pAD448, *E. coli* JM109 pAD450, *E. coli* JM109 pAD421, *E. coli* JM109 pAD422, *E. coli* JM109 pAD423, *E. coli* JM109 pAD424 (FERM BP-4034), *E. coli* JM109 pAD425, *E. coli* JM109 pAD426, *E. coli* JM109 pAD427, *E. coli* JM109, pAD451, *E. coli* JM109 pAD452, *E. coli* JM109 pAD453, *E. coli* JM109 pAD461, *E. coli* JM109 pAD454, *E. coli* JM109 pAD455 (FERM BP-4036), *E. coli* JM109 pAD456, *E. coli* JM109 pAD468, *E. coli* JM109 pAD469, *E. coli* JM109 pAD470 or *E. coli* HB101 pNT4553 (FERM BP-4368).

46. A vector plasmid pUC NT for the expression of a foreign gene.

\* \* \* \* \*